(12) United States Patent
Kakinuma et al.

(10) Patent No.: US 8,466,113 B2
(45) Date of Patent: Jun. 18, 2013

(54) 4-ISOPROPYLPHENYL GLUCITOL COMPOUNDS AS SGLT1 INHIBITORS

(75) Inventors: Hiroyuki Kakinuma, Toshima-ku (JP);
Yohei Kobashi, Toshima-ku (JP);
Tomomichi Chonan, Toshima-ku (JP);
Takahiro Oi, Toshima-ku (JP);
Fumiyasu Shiozawa, Toshima-ku (JP);
Yuki Iwata, Toshima-ku (JP); Kenichi Kawabe, Toshima-ku (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/202,523

(22) PCT Filed: Feb. 23, 2010

(86) PCT No.: PCT/JP2010/053187
§ 371 (c)(1),
(2), (4) Date: Aug. 19, 2011

(87) PCT Pub. No.: WO2010/095768
PCT Pub. Date: Aug. 26, 2010

(65) Prior Publication Data
US 2011/0306759 A1    Dec. 15, 2011

(30) Foreign Application Priority Data
Feb. 23, 2009    (JP) .................................. 2009-38776

(51) Int. Cl.
*C07H 5/04*    (2006.01)
*C07H 5/06*    (2006.01)
*A01N 43/04*    (2006.01)
*A61K 31/70*    (2006.01)

(52) U.S. Cl.
USPC .................................. 514/23; 536/53; 536/55

(58) Field of Classification Search
None
See application file for complete search history.

(56) References Cited

U.S. PATENT DOCUMENTS

| | | | |
|---|---|---|---|
| 7,973,012 B2 * | 7/2011 | Kakinuma et al. ............ | 514/23 |
| 2004/0176308 A1 | 9/2004 | Shiohara et al. | |
| 2005/0272669 A1 | 12/2005 | Fushimi et al. | |
| 2006/0035844 A1 | 2/2006 | Ito et al. | |
| 2007/0197623 A1 | 8/2007 | Brummerhop et al. | |
| 2010/0022460 A1 | 1/2010 | Kakinuma et al. | |

FOREIGN PATENT DOCUMENTS

| | | |
|---|---|---|
| EP | 1 548 024 A1 | 6/2005 |
| EP | 1544208 A1 | 6/2005 |
| WO | WO 02/98893 A1 | 12/2002 |
| WO | WO 2004/014932 A1 | 2/2004 |
| WO | WO 2004/018491 A1 | 3/2004 |
| WO | WO 2004/019958 A1 | 3/2004 |
| WO | WO 2004/050122 A1 | 6/2004 |
| WO | WO 2005/121161 A1 | 12/2005 |
| WO | 2007/136116 A2 | 11/2007 |

OTHER PUBLICATIONS

Adachi et al., Metabolism, vol. 49, No. 8, Aug. 2000, pp. 990-995.*
International Search Report of PCT/JP2010/053187 dated Apr. 24, 2010.

* cited by examiner

*Primary Examiner* — Traviss C McIntosh, III
(74) *Attorney, Agent, or Firm* — Sughrue Mion, PLLC

(57) ABSTRACT

The present invention provides 4-isopropylphenyl glucitol compounds which have no tendency to accumulate in the body and which inhibit SGLT1 activity to suppress postprandial hyperglycemia (or impaired glucose tolerance) through suppression of glucose absorption in the small intestine, whereby the compounds, for example, can suppress the onset of diabetes and metabolic syndrome or can treat these diseases.

A 4-isopropylphenyl glucitol compound represented by the following formula (I) or a pharmaceutically acceptable salt thereof:

[Chem. 1]

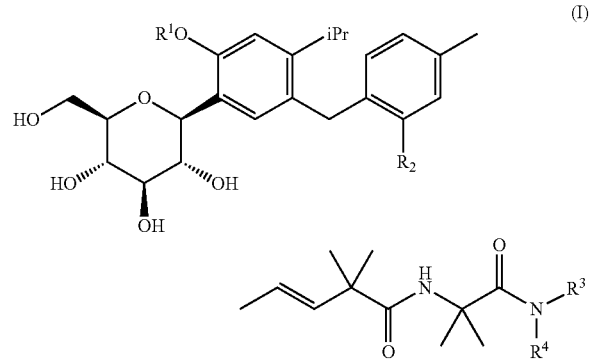

(I)

wherein $R^1$ represents a hydrogen atom, etc., $R^2$ represents a methyl group, etc., $R^3$ represents a $C_{1-4}$ alkyl group substituted with an amino group(s), etc., and $R^4$ represents a hydrogen atom, etc.

7 Claims, No Drawings

4-ISOPROPYLPHENYL GLUCITOL COMPOUNDS AS SGLT1 INHIBITORS

CROSS REFERENCE TO RELATED APPLICATIONS

This application is a National Stage of International Application No. PCT/JP2010/053187 filed Feb. 23, 2010, claiming priority based on Japanese Patent Application No. 2009-38776 filed Feb. 23, 2009, the contents of all of which are incorporated herein by reference in their entirety.

TECHNICAL FIELD

The present invention relates to 4-isopropylphenyl glucitol compounds which have inhibitory activity specific to sodium-dependent glucose transporter 1 (hereinafter abbreviated as "SGLT1" for convenience) involved in absorption of glucose and galactose in the small intestine.

BACKGROUND ART

Blood glucose levels are used as a biomarker for metabolic syndrome, and people are diagnosed as having diabetes if their fasting blood glucose levels exceed 126 mg/dL. Moreover, even if fasting blood glucose levels fall within a normal range, some people have 2-hour postprandial blood glucose levels as high as 140 to 200 mg/dL and are diagnosed as having impaired glucose tolerance (or postprandial hyperglycemia). Recent epidemiological studies have reported that impaired glucose tolerance increases the risk of cardiovascular disorders (see NPL 1 and NPL 2). Further, it has been reported that exercise therapy and/or medication not only suppresses the development of type II diabetes from impaired glucose tolerance, but also significantly suppresses the onset of hypertension (see NPL 3).

In view of the foregoing, suppression of postprandial hyperglycemia is of importance in suppressing the onset of diabetes and/or metabolic syndrome, and there has accordingly been an increasing demand for drugs used to control postprandial hyperglycemia.

As agents for improving postprandial hyperglycemia, α-glucosidase inhibitors have been conventionally used widely, which inhibit sugar hydrolases and thereby delay sugar absorption from the small intestine. In addition to these agents, there have been developed other agents with a new mechanism of action for improving postprandial hyperglycemia.

On the mammalian small intestinal epithelium, sodium-dependent glucose transporter 1 (SGLT1) is expressed at a high frequency. It is known that SGLT1 serves depending upon sodium and plays a role in active transport of glucose or galactose in the small intestine. Based on these findings, pyrazole derivatives have been reported, which inhibit SGLT1 activity to thereby suppress glucose absorption from a meal and can be used for prevention or treatment of postprandial hyperglycemia (see PTL 1 to PTL 6). On the other hand, sodium-dependent glucose transporter 2 (SGLT2) is expressed at a high frequency in the kidney, and glucose once filtered by the glomeruli is reabsorbed via SGLT2 (see NPL 4). Moreover, it has been reported that upon inhibition of SGLT2 activity, sugar excretion into urine is facilitated to induce a hypoglycemic action (see NPL 5). SGLT2 inhibitors are characterized in that they have an excellent hypoglycemic action to lower casual blood glucose levels, but their action to control postprandial hyperglycemia is low, unlike SGLT1 inhibitors. Further, there is a report of C-phenyl glucitol derivatives which inhibit not only SGLT1 activity but also SGLT2 activity at the same time (see PTL 7).

On the other hand, in the case of drugs required to be administered continuously, including agents for improving postprandial hyperglycemia, it is important to have a wide margin of safety between the therapeutic dose and the toxic or side effect dose. Particularly in the case of drugs prone to remain in the body, it is difficult to control their dosage required for treatment, so that an excessive drug effect will be developed as a result of summing residual drugs remaining in the body, thus leading to unexpected toxicity and side effects. For example, it is known that cationic drugs whose molecule has a hydrophilic group (e.g., a tertiary amine) and a hydrophobic group (e.g., an aromatic ring) bind to phospholipids through hydrophobic bonding and are taken up by lysosomes and hence accumulated in all organs in the body. As typical examples, chloroquine is shown to cause retinopathy, while perhexiline gives rise to a problem of neuropathy because it induces changes in the lung and cerebellum (see NPL 6).

Thus, drugs are desired to be rapidly excreted from the body after developing their efficacy. In particular, agents for improving postprandial hyperglycemia that must be administered continuously are desired to be free from the problem of accumulation in the body.

CITATION LIST

Patent Literature

[PTL 1] International Publication No. WO2002/098893
[PTL 2] International Publication No. WO2004/014932
[PTL 3] International Publication No. WO2004/018491
[PTL 4] International Publication No. WO2004/019958
[PTL 5] International Publication No. WO2005/121161
[PTL 6] International Publication No. WO2004/050122
[PTL 7] International Publication No. WO2007/136116

Non Patent Literature

[NPL 1] Pan X R, et al. Diabets Care, vol. 20, p. 537, 1997
[NPL 2] M Tominaga, et al. Diabets Care, vol. 22, p. 920, 1999
[NPL 3] J.-L. Chiasson, et al. Lancent, vol. 359, p. 2072, 2002
[NPL 4] E. M. Wright, Am. J. Physiol. Renal. Physiol., vol. 280, p. F10, 2001
[NPL 5] G. Toggenburger, et al. Biochem. Biophys. Acta., vol. 688, p. 557, 1982
[NPL 6] Folia Pharmacol. Jpn. vol. 113, p. 19, 1999

SUMMARY OF INVENTION

Technical Problem

The object of the present invention is to provide compounds or salts thereof with an inhibitory effect against SGLT1, which have a wide margin of safety between the therapeutic dose and the toxic or side effect dose, as well as pharmaceutical preparations comprising the same.

Solution to Problem

The C-phenyl glucitol derivatives disclosed in PTL 7 were found to have a tendency to remain in the kidney without being excreted. Based on this fact, the inventors of the present invention have made extensive and intensive efforts to investigate compounds free from the problem of accumulation in the body. As a result, the inventors have found that 4-isopropylphenyl glucitol compounds represented by the following formula (I), which are obtained, in particular, by introducing an isopropyl group into the benzene ring directly attached to the sugar moiety and introducing a butenoyl group with an amino group into the other benzene ring, unexpectedly have no tendency to remain in the kidney. This finding led to the completion of the present invention.

Embodiments will be given below for the 4-isopropylphenyl glucitol compounds of the present invention (hereinafter referred to as "the compounds of the present invention").

(1) A 4-isopropylphenyl glucitol compound represented by the following formula (I) or a pharmaceutically acceptable salt thereof:

[Chem. 1]

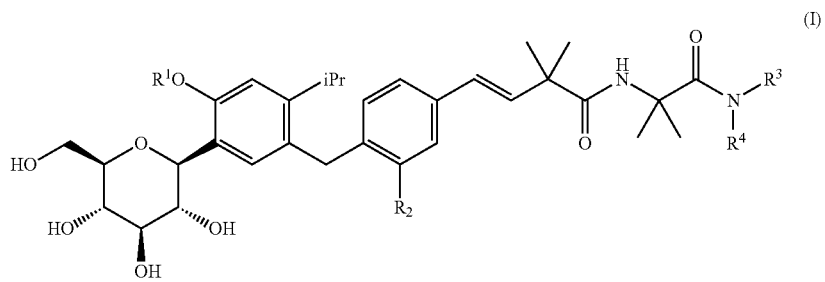

(I)

wherein
$R^1$ represents a hydrogen atom or a $C_{1-4}$ alkyl group,
$R^2$ represents a hydrogen atom or a methyl group,
$R^3$ represents a "$C_{1-4}$ alkyl group substituted with an amino group(s) or a di-$C_{1-4}$ alkylamino group(s)" or a piperidyl group, and
$R^4$ represents a hydrogen atom, or alternatively, $R^3$ and $R^4$ together with their adjacent nitrogen atom form a piperidino group or a piperazinyl group, which may be substituted with a $C_{1-4}$ alkyl group(s) or a dimethylamino group(s).

(2) A 4-isopropylphenyl glucitol compound selected from the following group or a pharmaceutically acceptable salt thereof.

[Chem. 2]

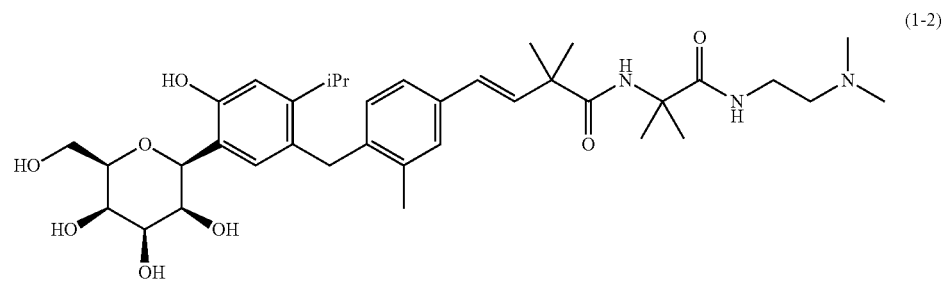

(1-2)

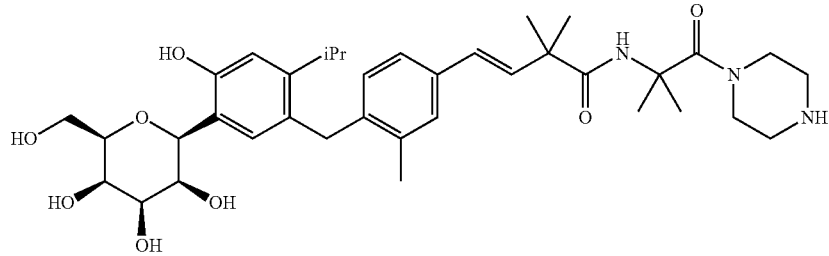

(2-2)

-continued
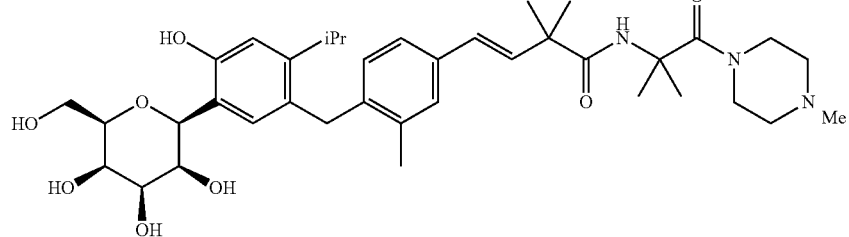
(3-2)
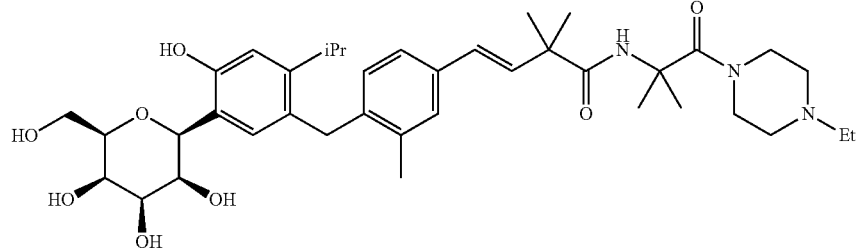
(4-2)
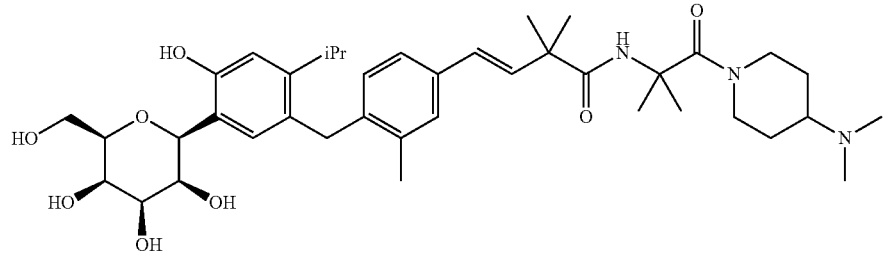
(5-2)
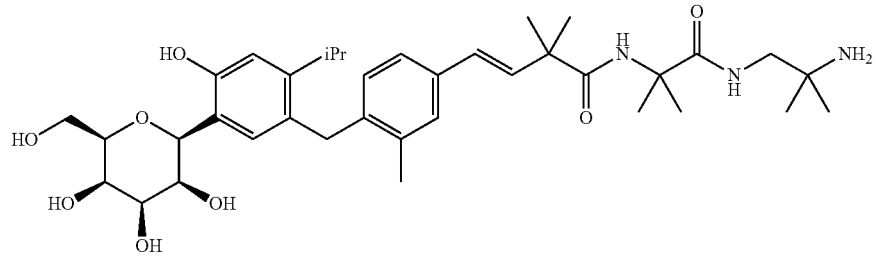
(6-2)
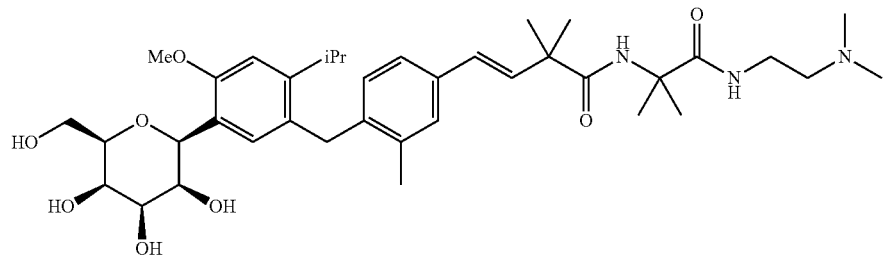
(7-2)
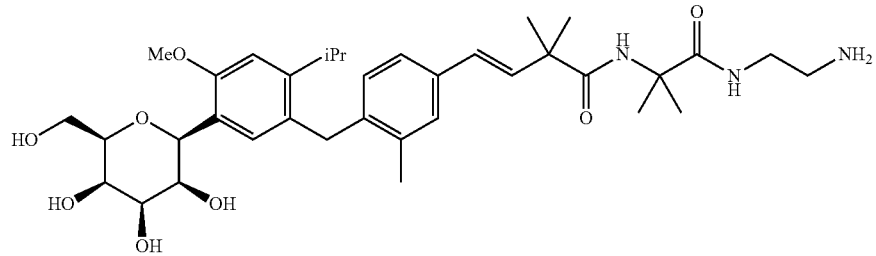
(8-3)

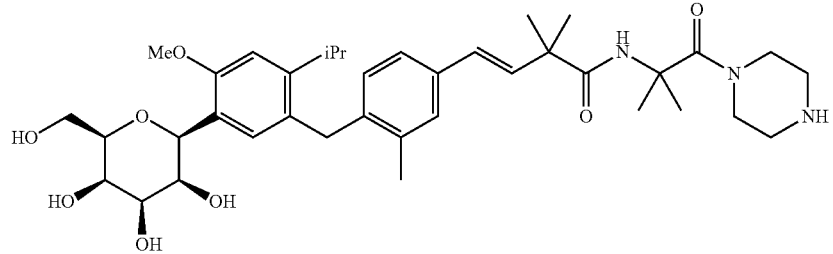
(9-2)
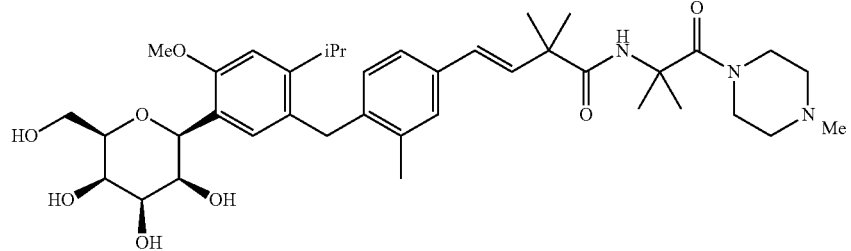
(10-2)
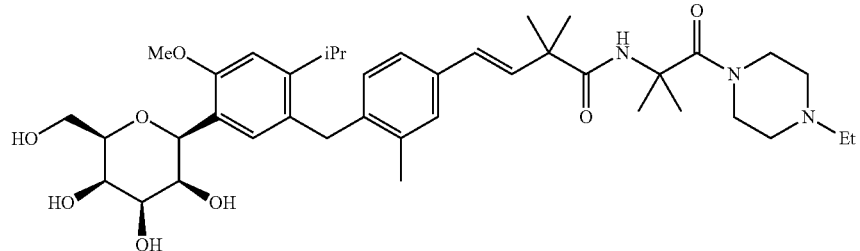
(11-2)
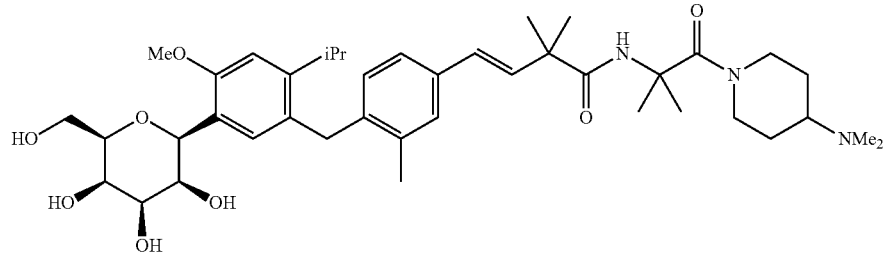
(12-2)
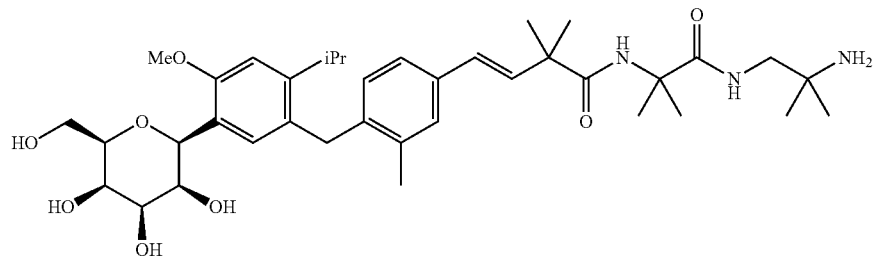
(13-2)
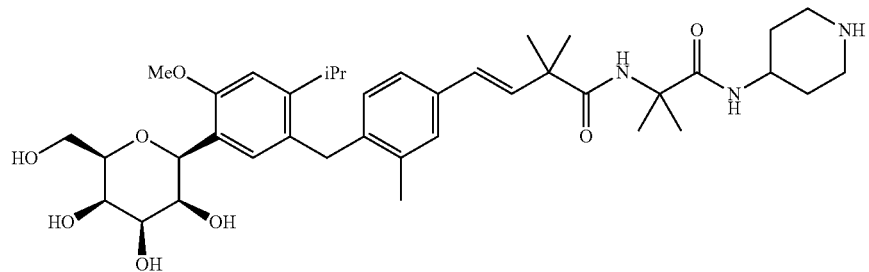
(14-2)

(15-2)
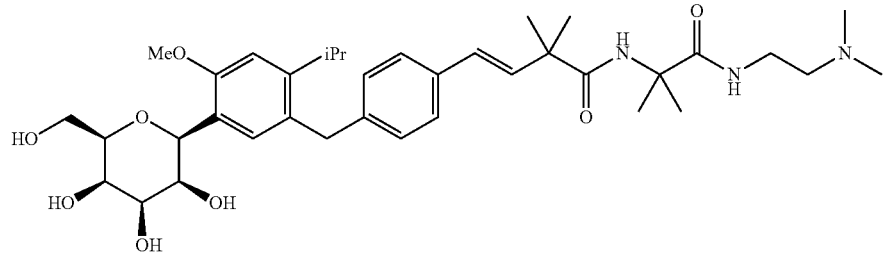
(16-2)
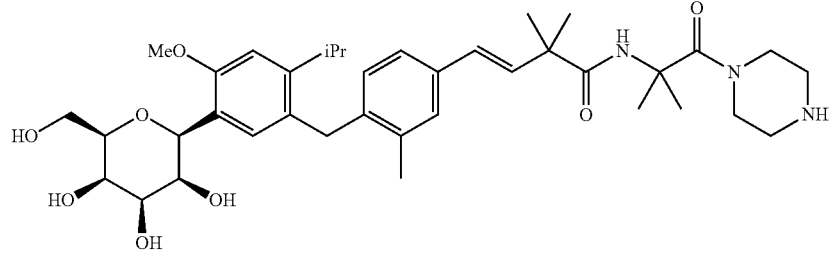
(17-2)
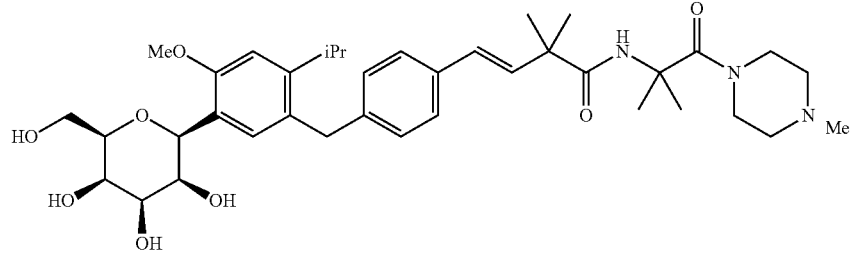
(3) A 4-isopropylphenyl glucitol compound selected from the following group or a pharmaceutically acceptable salt thereof.
[Chem. 3]
(1-2)
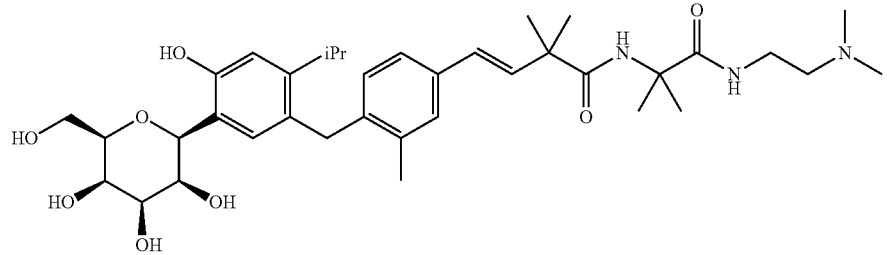
(5-2)
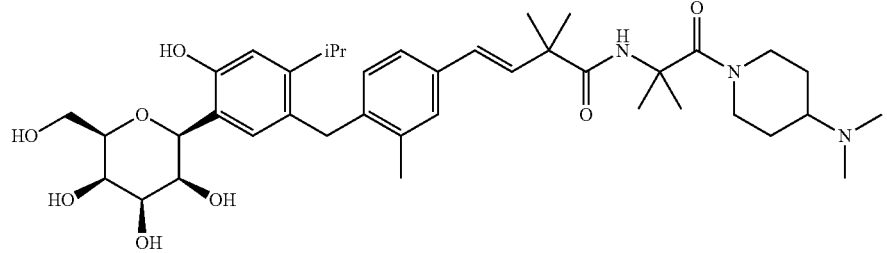

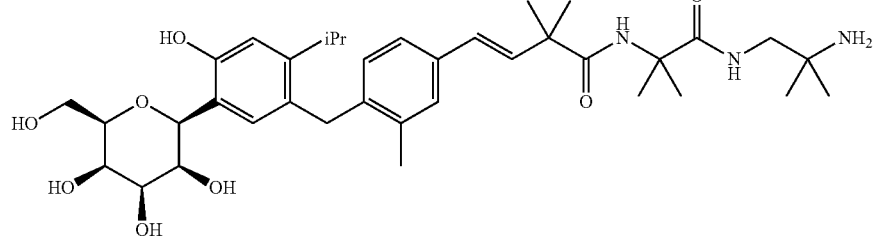

(6-2)

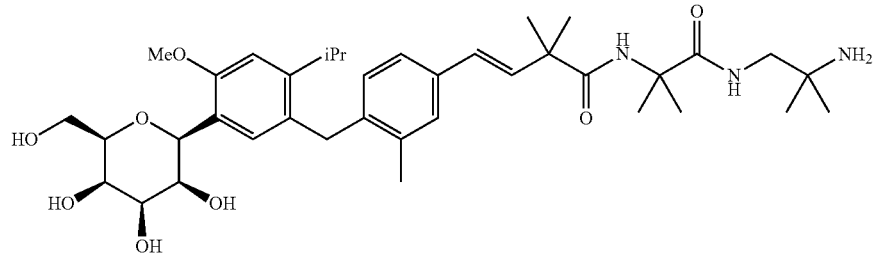

(13-2)

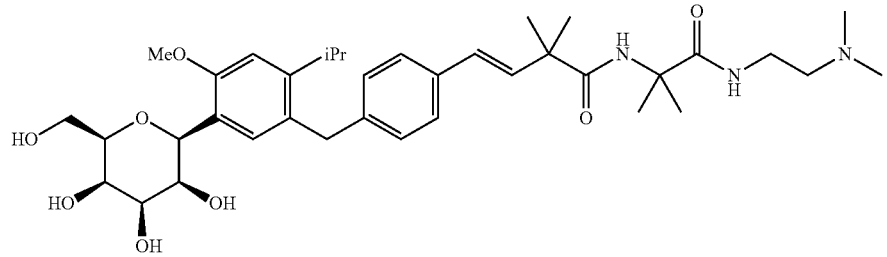

(15-2)

(4) A pharmaceutical preparation, which comprises the 4-isopropylphenyl glucitol compound according to any one of (1) to (3) above or a pharmaceutically acceptable salt thereof as an active ingredient.
(5) An inhibitor of sodium-dependent glucose transporter 1 (SGLT1) activity, which comprises the 4-isopropylphenyl glucitol compound according to any one of (1) to (3) above or a pharmaceutically acceptable salt thereof as an active ingredient.
(6) An agent for improving postprandial hyperglycemia, which comprises the 4-isopropylphenyl glucitol compound according to any one of (1) to (3) above or a pharmaceutically acceptable salt thereof as an active ingredient.
(7) A prophylactic or therapeutic agent for diabetes, which comprises the 4-isopropylphenyl glucitol compound according to any one of (1) to (3) above or a pharmaceutically acceptable salt thereof as an active ingredient.
(8) Use of the 4-isopropylphenyl glucitol compound according to any one of (1) to (3) above or a pharmaceutically acceptable salt thereof in the manufacture of prophylactic or therapeutic agents for diabetes.
(9) A method for preventing or treating diabetes, which comprises administering to a mammal a therapeutically effective amount of the 4-isopropylphenyl glucitol compound according to any one of (1) to (3) above or a pharmaceutically acceptable salt thereof.

Advantageous Effects of Invention

The present invention enables the provision of 4-isopropylphenyl glucitol compounds which have no tendency to accumulate in the body and which inhibit SGLT1 activity.

DESCRIPTION OF EMBODIMENTS

The terms and phrases used herein are defined as follows.
The term "$C_{1-4}$ alkyl group" is intended to mean a linear or branched alkyl group containing 1 to 4 carbon atoms. Examples include a methyl group, an ethyl group, a n-propyl group, an isopropyl group, a n-butyl group, an isobutyl group, and a tert-butyl group.
The term "di-$C_{1-4}$ alkylamino group" is intended to mean an amino group substituted with two $C_{1-4}$ alkyl groups. Examples include a dimethylamino group and a diethylamino group.
In addition, the term "pharmaceutically acceptable salt" is intended to mean, for example, a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, a formate salt, an acetate salt, a propionate salt, a butyrate salt, a hexanoate salt, an octanoate salt, a trifluoroacetate salt, a maleate salt, a tartrate salt, a citrate salt, a stearate salt, a succinate salt, an ethylsuccinate salt, a lactobionate salt, a gluconate salt, a glucuronate salt, a glucoheptate salt, a glutarate salt, a pimelate salt, a suberate salt, an azelate salt, a sebacate salt, a 1,9-nonanedicarboxylate salt, a dodecanedioate salt, a tridecanedioate salt, a tetradecanedioate salt, a pentadecanedioate salt, a hexadecanedioate salt, a heptadecanedioate salt, a benzoate salt, a 2-hydroxybenzoate salt, a methanesulfonate salt, an ethanesulfonate salt, an ethanedisulfonate salt, a 2-hydroxyethanesulfonate salt, a benzenesulfonate salt, a p-toluenesulfonate salt, a 1,5-naphthalenedisulfonate salt, a lauryl sulfate salt, a lactate salt, a hippurate salt, a fumarate salt, a malonate salt, a trans-cinnamate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, a undecanoate salt, a salt with an acrylate polymer, and a salt with a carboxyvinyl polymer.

The phrase "agent for improving postprandial hyperglycemia" is intended to mean a drug which suppresses postprandial hyperglycemia to thereby suppress the onset of postprandial hyperglycemia-related diseases (e.g., diabetes, metabolic syndrome) or treat such diseases. As used herein, the term "postprandial hyperglycemia" is intended to mean a state where blood glucose levels are abnormally elevated after a meal, more specifically a state where 2-hour postprandial blood glucose levels exceed 140 mg/dl.

The usefulness of the compounds of the present invention will be described below (for details, see the test examples described later).

The compounds of the present invention have strong SGLT1 inhibitory activity and also have some, although weak, SGLT2 inhibitory activity. Moreover, the compounds of the present invention have a hypoglycemic effect as strong as that of the compounds disclosed in WO2007/136116. Furthermore, the compounds disclosed in WO2007/136116 tend to remain in the kidney without being excreted even at day 7 after oral administration at 1 mg/kg, whereas the compounds of the present invention exhibited a characteristic feature in that even when they were administered for 3 consecutive days at a dose of 3 mg/kg, they unexpectedly did not remain in the kidney at subsequent day 2.

Thus, the compounds of the present invention have no tendency to remain in the body and are less likely to cause side effects and toxicity due to continuous administration, and hence appear to have practically excellent properties as pharmaceutical preparations.

When the compounds of the present invention are provided in the form of pharmaceutical preparations, various types of dosage forms such as solids and solutions may be selected as appropriate. In this case, a pharmaceutically acceptable carrier(s) may also be incorporated. Examples of such a carrier include commonly used excipients, extenders, binders, disintegrating agents, coating agents, sugar-coating agents, pH adjustors, solubilizers, or aqueous or non-aqueous solvents. The compounds of the present invention and these carriers may be formulated into tablets, pills, capsules, granules, powders, solutions, emulsions, suspensions or other dosage forms.

For example, the compounds of the present invention can be provided in the form of oral tablets by being mixed and tabletted with excipients and so on which are commonly used for manufacture of solid preparations.

Also, the compounds of the present invention may be included within, e.g., α-, β- or γ-cyclodextrin or methylated cyclodextrin to improve their solubility.

The dosage of the compounds of the present invention will vary depending on the disease or symptom to be treated, body weight, age, sex, the route of administration, etc. The daily dosage for adults is 0.1 to 1000 mg/kg body weight, preferably 0.1 to 200 mg/kg body weight, and more preferably 0.1 to 10 mg/kg body weight, given as a single dose or in divided doses.

As preferred embodiments of the present invention, the following compounds can be presented, which are prepared in the Example section.

[Chem. 4]

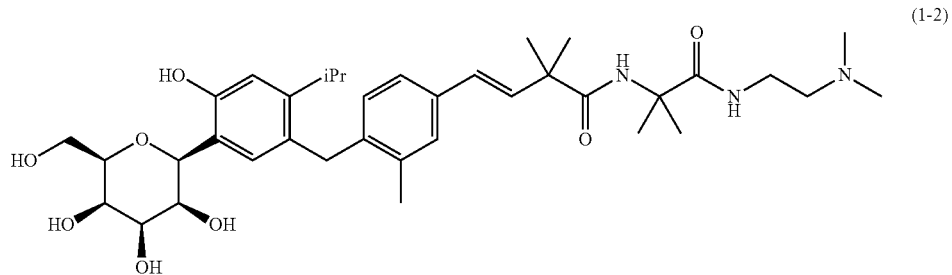

(1-2)

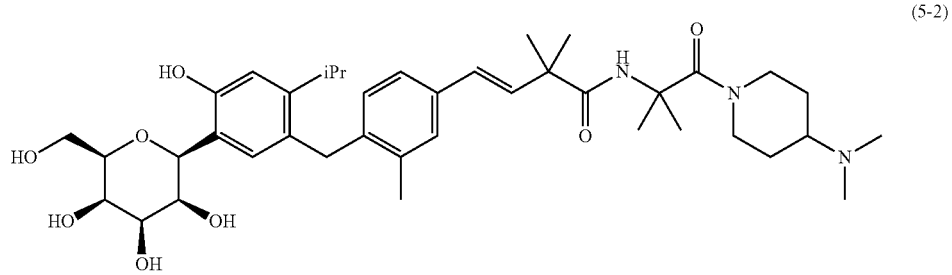

(5-2)

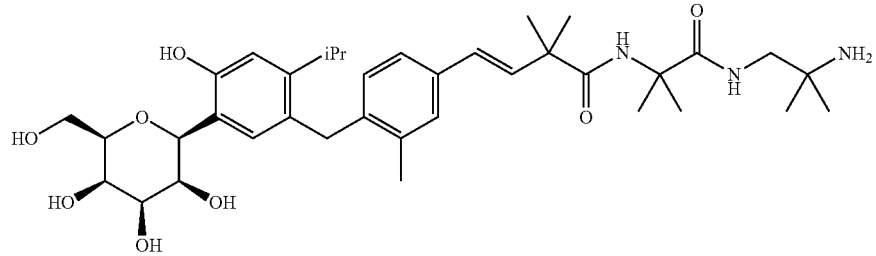

(6-2)

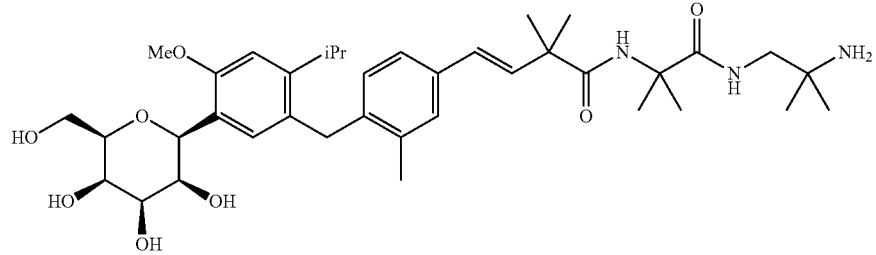

(13-2)

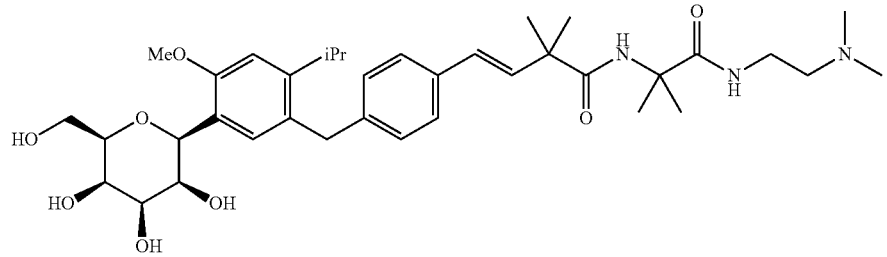

(15-2)

How to prepare the compound (I) of the present invention will be explained in more detail below by way of some examples, but is not limited to the particular cases illustrated below.

Preparation Procedure 1

The compound (I) of the present invention can be synthesized in the following manner In the scheme shown below, X represents an acetyl group or a $C_{1-4}$ alkyl group, $R^5$ represents $R^3$ or $R^3$ in which the amino group is protected with tert-butylcarbonate (Boc), and the other symbols are as defined above.

[Chem. 5]

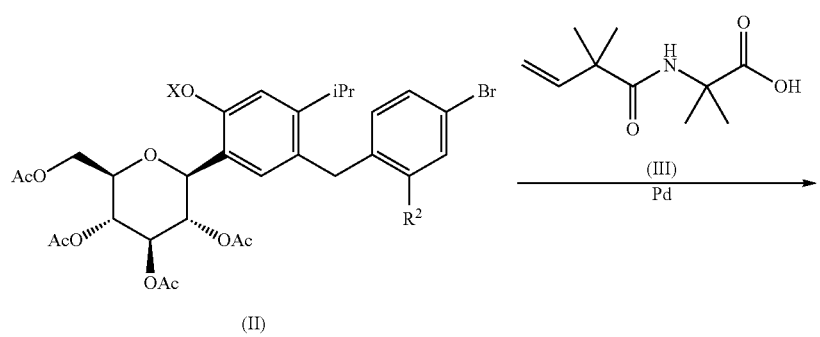

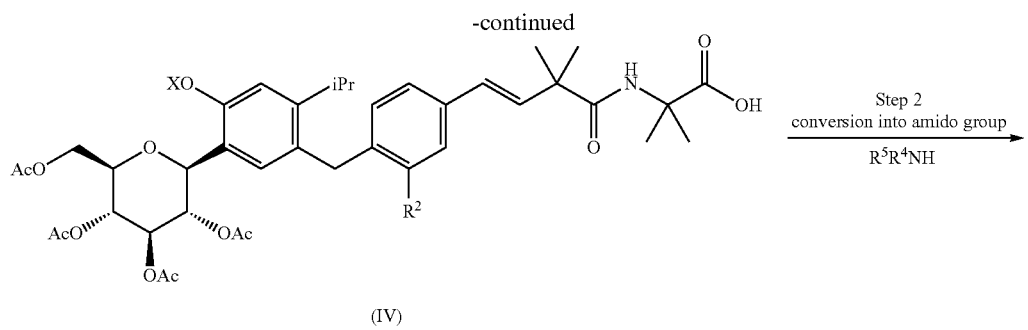

(IV)

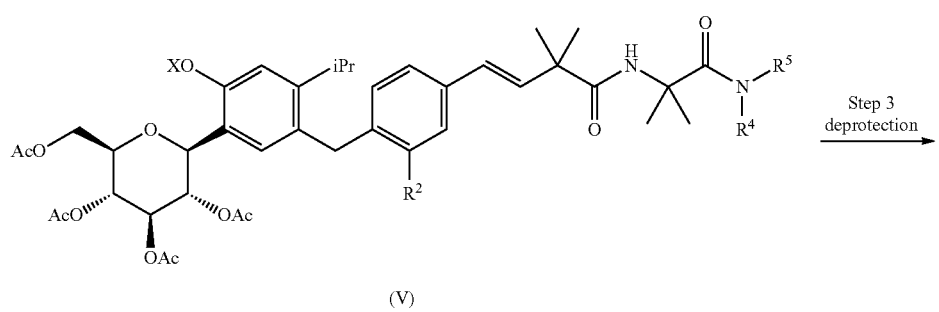

(V)

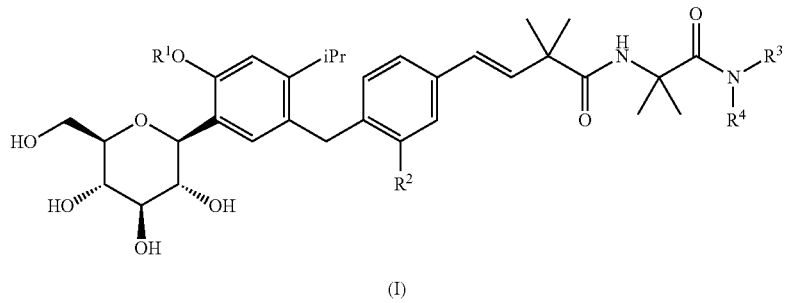

(I)

(1) Step 1 (Heck Reaction)

Compound (II) and olefin carboxylic acid (III) may be subjected to Heck reaction in the presence of a palladium catalyst, a phosphine ligand and an appropriate base to give compound (IV). Examples of a palladium catalyst used for this purpose include palladium acetate, tetrakis(triphenylphosphine)palladium, dibenzylideneacetonepalladium, bis(triphenylphosphine)palladium chloride, bis(tricyclohexylphosphine)palladium chloride, and palladium on activated carbon. Examples of a phosphine ligand include triphenylphosphine and tri-O-tolylphosphine. Likewise, examples of a base available for use include triethylamine, N-ethyl-N, N-diisopropylamine, potassium carbonate, calcium carbonate, cesium carbonate, and potassium t-butoxide. Examples of a solvent available for use in the reaction include acetonitrile, toluene, and tetrahydrofuran. The reaction temperature ranges from 0° C. to reflux temperature, or microwave may be used instead.

(2) Step 2 (Conversion into Amido Group)

Compound (IV) may be condensed through dehydration with an amine ($R^5R^4NH$) to give compound (V). Examples of a solvent preferred for use in this reaction include chloroform, dichloromethane, and N,N-dimethylformamide. Examples of a dehydration condensing agent preferred for this purpose include N,N'-dicyclohexylcarbodiimide (DCC), N-ethyl-N'-3-dimethylaminopropylcarbodiimide hydrochloride (EDC.HCl), 1,1'-carbonyldiimidazole (CDI), and EDC.HCl/1-hydroxybenzotriazole monohydrate (HOBt.H$_2$O). The reaction temperature in this case ranges from 0° C. to 60° C.

(3) Step 3 (Deprotection)

The Boc group in compound (V) may be removed under acidic conditions and the acetyl (Ac) groups may be removed under basic conditions to give compound (I). The Boc group is treated with hydrochloric acid or trifluoroacetic acid with or without a solvent (e.g., dichloromethane, chloroform, dioxane). For the acetyl groups, it is possible to use a base such as sodium methoxide, sodium hydroxide, lithium hydroxide, potassium carbonate, cesium carbonate, or triethylamine Examples of a solvent preferred for this purpose include methanol, ethanol, and aqueous methanol. The reaction temperature in this case ranges from 0° C. to 60° C.

Preparation Procedure 2

The compound (I) of the present invention can also be synthesized through another route shown below. In the scheme shown below, the symbols are as defined above.

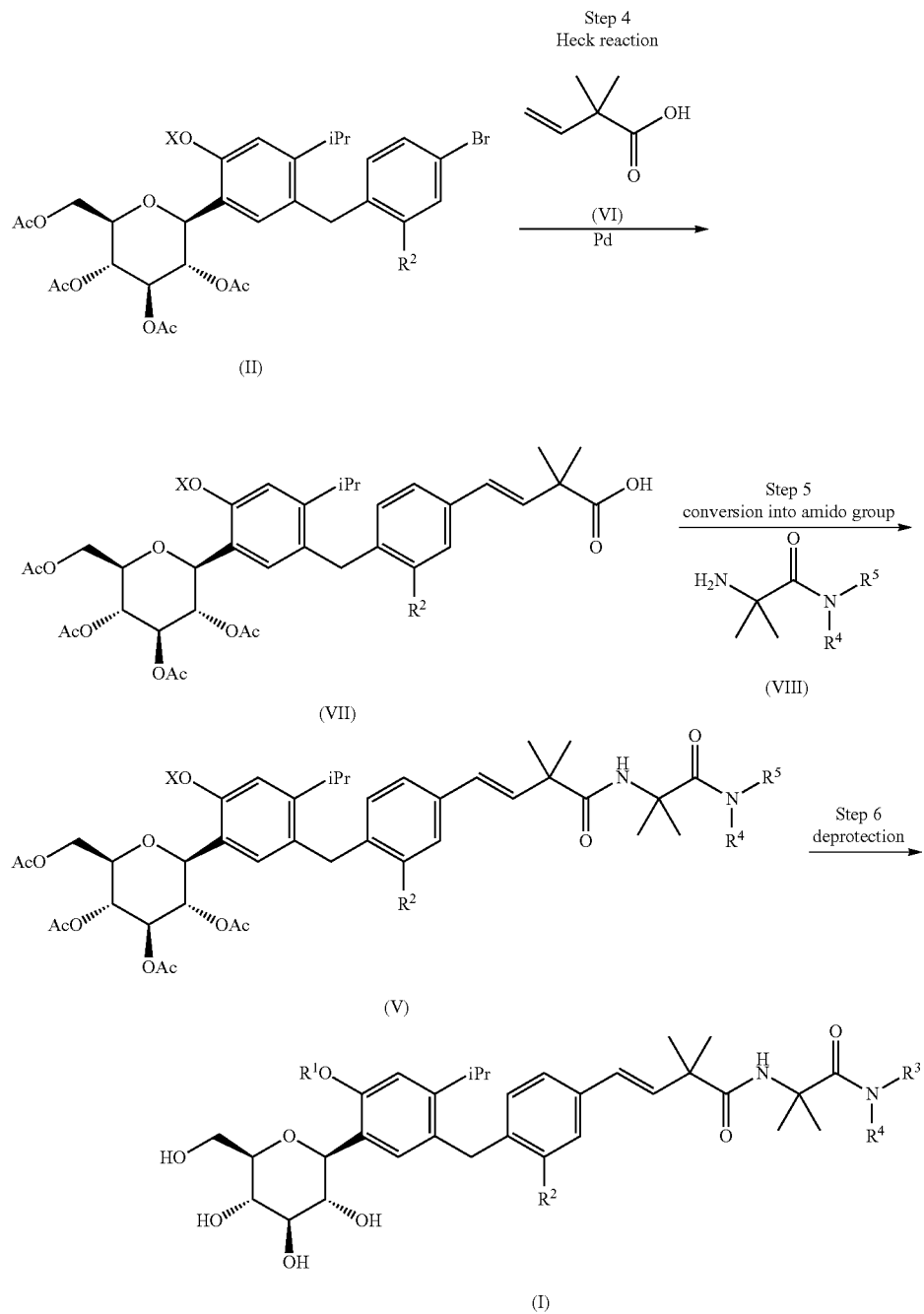

(4) Step 4 (Heck Reaction)

Compound (II) and olefin carboxylic acid (VI) may be used and subjected to Heck reaction as shown in Step 1 of Preparation Procedure 1 to give compound (VII).

(5) Step 5 (Conversion into Amido Group)

Compound (VII) and amine (VIII) may be used and condensed through dehydration as shown in Step 2 of Preparation Procedure 1 to give compound (V).

(6) Step 6 (Deprotection)

Compound (V) obtained above may be converted into compound (I) by deprotection reaction as shown in Step 3 of Preparation Procedure 1.

Preparation Procedure 3

Preparation Procedure for Intermediate (II)

How to prepare intermediate (II), which is required for preparation of the compound (I) of the present invention, will be illustrated below.

In the scheme shown below, $X^1$ represents a benzyl group or a $C_{1-4}$ alkyl group, $X^2$ represents a trimethylsilyl group or a $C_{1-4}$ alkyl group, and the other symbols are as defined above.

[Chem. 7]

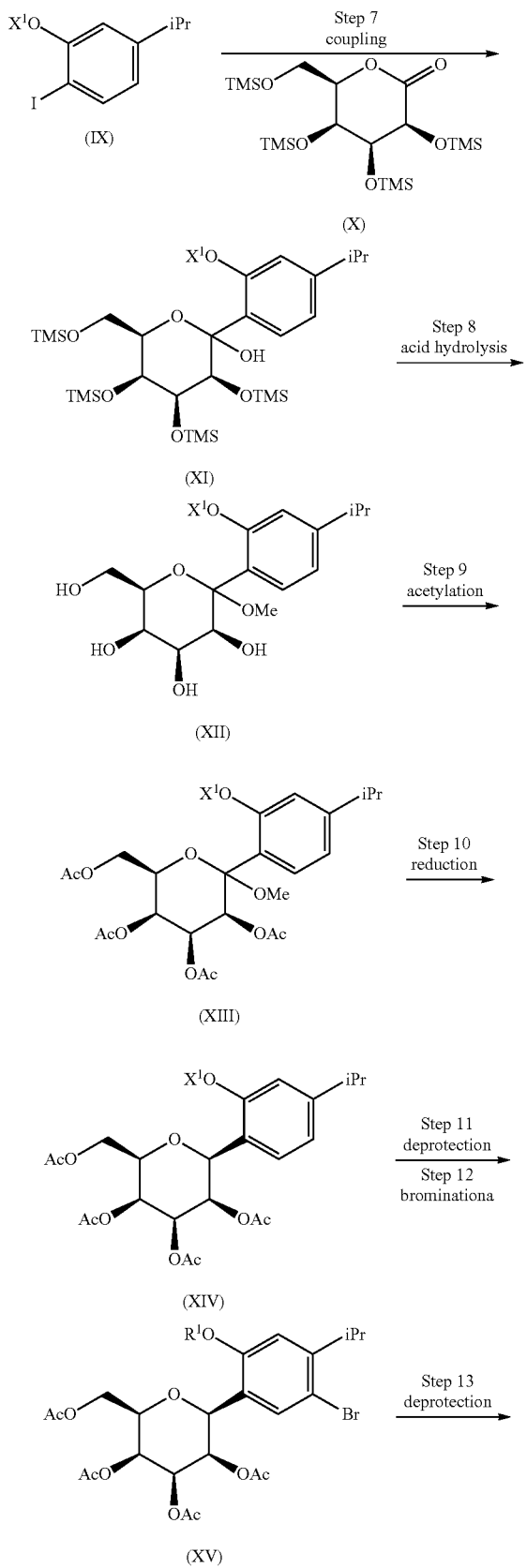
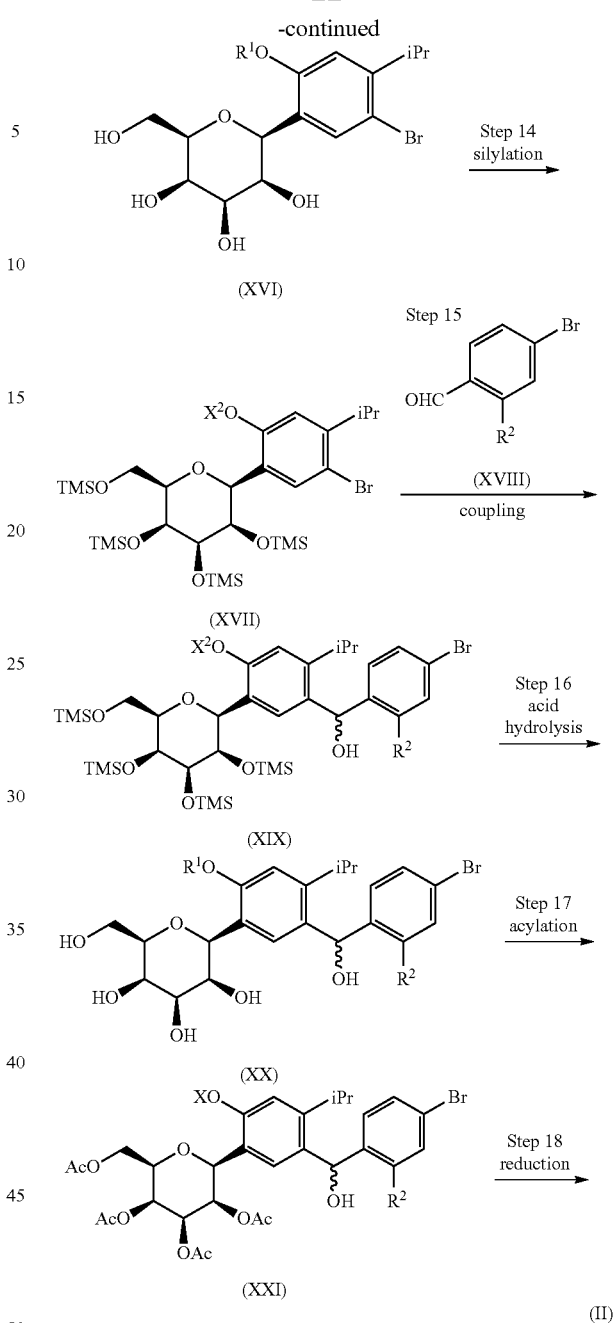

(7) Step 7 (Coupling)

Compound (IX) may be treated with an organometallic reagent (e.g., n-butyllithium, sec-butyllithium, tert-butyllithium) to prepare an aryl lithium reagent. To this reagent, gluconolactone (X) may be added to give compound (XI). Examples of a solvent available for use in this reaction include tetrahydrofuran, diethyl ether, and toluene. The reaction temperature ranges from −80° C. to room temperature, preferably from −78° C. to −25° C.

(8) Step 8 (Acid Hydrolysis)

Along with removing the silyl groups in compound (XI) in methanol under acidic conditions, the 1-position of the sugar moiety may be converted into methyl ether to give compound (XII). Examples of an acid used for this purpose include hydrochloric acid, sulfuric acid, methanesulfonic acid, p-toluenesulfonic acid monohydrate, pyridinium p-toluenesulfonate, hydrogen fluoride pyridine, and n-Bu$_4$NF. Although the reaction temperature will vary depending on the type of acid to be used, it ranges from 0° C. to 100° C., preferably from 25° C. to 80° C.

(9) Step 9 (Acetylation)

The hydroxyl groups in compound (XII) may be protected with acetyl groups to give compound (XIII). Compound (XII) may be reacted with, for example, acetic anhydride or acetyl chloride in a solvent in the presence of an appropriate base to give compound (XIII). Examples of a solvent available for use in the reaction include chloroform, dichloromethane, dioxane, ethyl acetate, tetrahydrofuran, and N,N-dimethylformamide. Examples of a base preferred for this purpose include triethylamine, collidine, and pyridine. As a reaction catalyst, 4-dimethylaminopyridine may be used. The reaction temperature preferably ranges from 0° C. to room temperature.

(10) Step 10 (Reduction)

Compound (XIII) may be reacted with Et$_3$SiH, i-Pr$_3$SiH, t-BuMe$_2$SiH or Ph$_2$SiHCl in the presence of a Lewis acid to give compound (XIV). Examples of a Lewis acid available for use in this reaction include BF$_3$.Et$_2$O, CF$_3$COOH, InCl$_3$, TiCl$_4$, TMSOTf, p-toluenesulfonic acid, and methanesulfonic acid. Examples of a solvent include chloroform, dichloromethane, toluene, tetrahydrofuran, acetonitrile or mixed solvents thereof, and preferred are mixed solvents with acetonitrile, such as acetonitrile/chloroform, acetonitrile/dichloromethane, acetonitrile/tetrahydrofuran, acetonitrile/tetrahydrofuran/toluene, etc. The reaction temperature in this case ranges from −60° C. to 25° C., preferably from −30° C. to 25° C.

(11) Step 11 (Deprotection)

In a case where $X^1$ in compound (XIV) is a benzyl group, debenzylation may be accomplished by catalytic hydrogenation under a hydrogen atmosphere using a catalyst such as palladium on activated carbon, palladium hydroxide, or platinum-palladium on activated carbon. Among them, palladium on activated carbon or palladium hydroxide is preferred as a catalyst. Examples of a solvent available for use in this reaction include methanol, ethanol, isopropanol, ethyl acetate, acetic acid, and mixed solvents thereof. The reaction temperature ranges from room temperature to reflux temperature, with room temperature being preferred.

(12) Step 12 (Bromination)

Compound (XIV) or the compound obtained in Step 11 above may be reacted with bromine, N-bromosuccinimide, hydrogen bromide or the like in a solvent to give compound (XV). Examples of a solvent available for use in the reaction include chloroform, dichloromethane, acetic acid, methanol, and N,N-dimethylformamide. The reaction temperature in this case ranges from 0° C. to room temperature.

(13) Step 13 (Deprotection)

The acetyl groups in compound (XV) may be removed under basic conditions to give compound (XVI). Examples of a base available for use include sodium methoxide, sodium hydroxide, lithium hydroxide, potassium carbonate, cesium carbonate, and triethylamine. Examples of a solvent preferred for this purpose include methanol, ethanol, and aqueous methanol. The reaction temperature in this case ranges from 0° C. to 60° C.

(14) Step 14 (Silylation)

The hydroxyl groups in compound (XVI) may be protected with silyl groups (e.g., trimethylsilyl groups) to give compound (XVII). Compound (XVI) may be reacted with trimethylsilyl chloride, triethylsilyl chloride, tert-butyldimethylsilyl chloride or the like in a solvent in the presence of an appropriate base to give compound (XVII). Examples of a solvent available for use in the reaction include chloroform, dichloromethane, dioxane, ethyl acetate, tetrahydrofuran, and N,N-dimethylformamide. Examples of a base preferred for this purpose include triethylamine, collidine, and pyridine. The reaction temperature preferably ranges from 0° C. to room temperature.

(15) Step 15 (Coupling)

Compound (XVII) may be treated with an organometallic reagent (e.g., n-butyllithium, sec-butyllithium, tert-butyllithium) to prepare an aryl lithium reagent. To this reagent, aldehyde (XVIII) may be added to give compound (XIX). Examples of a solvent available for use in this reaction include tetrahydrofuran, diethyl ether, and toluene. The reaction temperature ranges from −80° C. to room temperature, preferably from −78° C. to −25° C.

(16) Step 16 (Acid Hydrolysis)

Compound (XIX) obtained above may be converted into compound (XX) by acid hydrolysis reaction as shown in Step 8 of Preparation Procedure 3.

(17) Step 17 (Acetylation)

Compound (XX) obtained above may be converted into compound (XXI) by acetylation reaction as shown in Step 9 of Preparation Procedure 3.

(18) Step 18 (Reduction)

Compound (XXI) obtained above may be converted into intermediate (II) by reduction reaction as shown in Step 10 of Preparation Procedure 3.

Preparation Procedure 4

Preparation Procedure for Intermediate (II)

Intermediate (II) can also be synthesized through another route shown below. In this route, Steps 19 to 21 may be performed in one pot to thereby reduce the number of steps.

In the scheme shown below, the symbols are as defined above.

[Chem. 8]

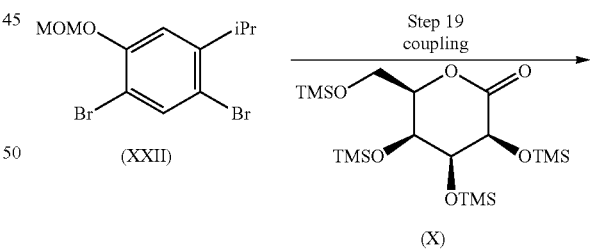

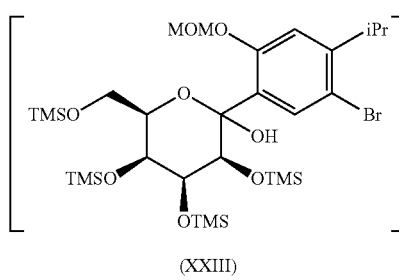

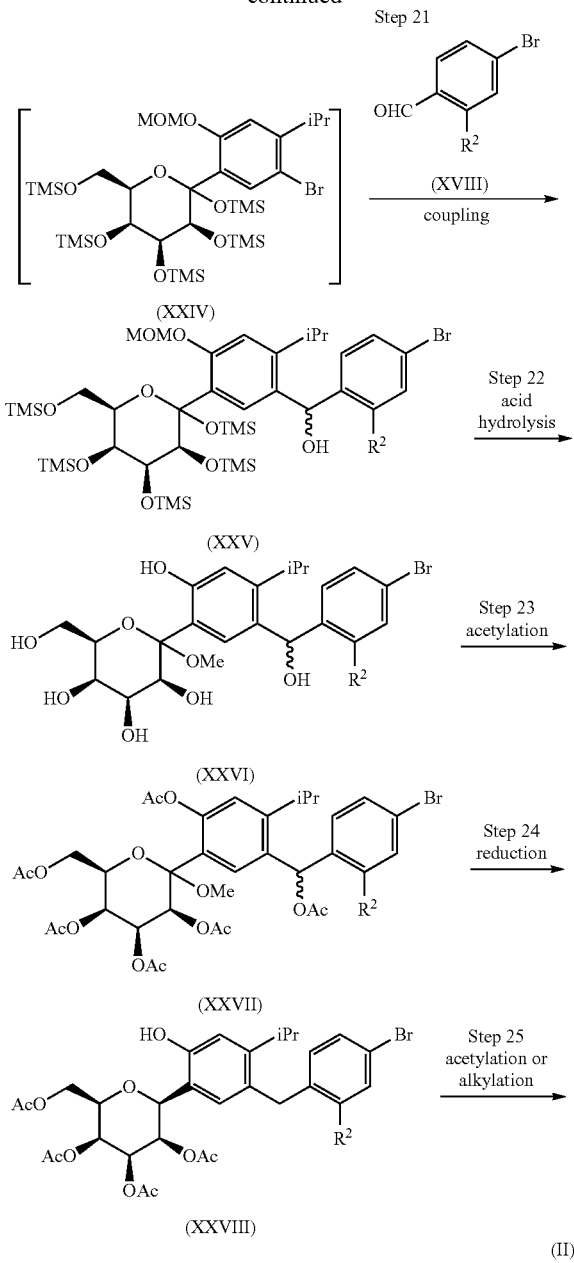

(19) Step 19 (Coupling)

Compound (XXII) may be treated with an organometallic reagent (e.g., n-butyllithium, sec-butyllithium, tert-butyllithium) to prepare an aryl lithium reagent. To this reagent, gluconolactone (X) may be added to give compound (XXIII). Examples of a solvent available for use in this reaction include tetrahydrofuran, diethyl ether, and toluene. The reaction temperature ranges from −80° C. to room temperature, preferably from −78° C. to −25° C.

(20) Step 20 (Silylation)

Subsequently to Step 19 above, the hydroxyl group at the 1-position of compound (XXIII) may be protected with a silyl group (e.g., a trimethylsilyl group). The reaction solution from Step 19 may be reacted with trimethylsilyl chloride to give compound (XXIV). A solvent available for use in the reaction and a preferred reaction temperature are the same as those in Step 19.

(21) Step 21 (Coupling)

Subsequently to Step 20 above, compound (XXIV) thus generated may be treated with an organometallic reagent (e.g., n-butyllithium, sec-butyllithium, tert-butyllithium) to prepare an aryl lithium reagent. To this reagent, aldehyde (XVIII) may be added to give compound (XXV). A solvent available for use in this reaction and a preferred reaction temperature are the same as those in Step 19.

(22) Step 22 (Acid Hydrolysis)

Compound (XXV) obtained above may be converted into compound (XXVI) by acid hydrolysis reaction as shown in Step 8 of Preparation Procedure 3.

(23) Step 23 (Acetylation)

Compound (XXVI) obtained above may be converted into compound (XXVII) by acetylation reaction as shown in Step 9 of Preparation Procedure 3.

(24) Step 24 (Reduction)

Compound (XXVII) obtained above may be converted into compound (XXVIII) by reduction reaction as shown in Step 10 of Preparation Procedure 3.

(25) Step 25 (Acetylation or Alkylation)

The hydroxyl group in compound (XXVIII) may be protected with an acetyl group or may be alkylated (e.g., methylated) to prepare intermediate (II). Compound (XXVIII) may be reacted with, for example, acetic anhydride or acetyl chloride in a solvent in the presence of an appropriate base to give intermediate (II). Examples of a solvent available for use in the reaction include chloroform, dichloromethane, dioxane, ethyl acetate, tetrahydrofuran, and N,N-dimethylformamide. Examples of a base preferred for this purpose include triethylamine, collidine, and pyridine. As a catalyst, 4-dimethylaminopyridine or the like may be used. The reaction temperature preferably ranges from 0° C. to room temperature. Alternatively, compound (XXVIII) may be reacted with methyl iodide, ethyl iodide, 2-iodopropane or the like in a solvent in the presence of an appropriate base to give intermediate (II). Examples of a solvent available for use in the reaction include chloroform, dichloromethane, tetrahydrofuran, N,N-dimethylformamide, and acetone. Examples of a base preferred for this purpose include potassium carbonate, and cesium carbonate.

EXAMPLES

The present invention will be further described in more detail by way of the following reference examples, examples and test examples, but the present invention should not be construed as being limited thereby.

Reference Example 1

Preparation of Intermediate (A)

[Chem. 9]

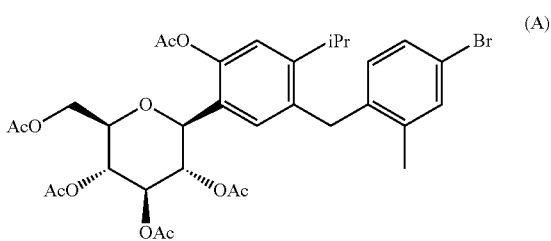

(1) Reference Example 1-1

Compound (A1)

[Chem. 10]

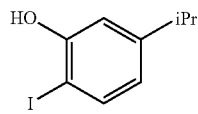

To a solution of 3-isopropylphenol (25.0 g, 0.184 mol) in acetic acid (200 mL), a suspension of potassium iodate (7.88 g, 0.0368 mol) in water (75 mL) and iodine (18.7 g, 0.0736 mol) were added. This reaction mixture was stirred at room temperature for 20 hours. After addition of diethyl ether (400 mL) and water (300 mL), the organic layer was separated. The organic layer was washed with water, saturated aqueous sodium bicarbonate and brine, and then dried over anhydrous magnesium sulfate. After filtering off the desiccant, the solvent was distilled off under reduced pressure and the resulting residue was purified by silica gel column chromatography (hexane:ethyl acetate=95:5) to give compound (A1) (27.6 g, 57%) as a colorless oil.

$^1$H NMR (200 MHz, CHLOROFORM-d) δ ppm 1.16-1.25 (m, 6H) 2.64-2.98 (m, 1H) 5.21 (s, 1H) 6.57 (dd, J=8.13, 2.20 Hz, 1H) 6.88 (d, J=2.20 Hz, 1H) 7.54 (d, J=8.13 Hz, 1H).

(2) Reference Example 1-2

Compound (A2)

[Chem. 11]

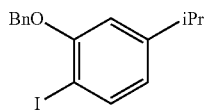

To an acetonitrile suspension of compound (A1) (26.5 g, 0.101 mol) and potassium carbonate (20.9 g, 0.152 mol), benzyl bromide (14.4 mL, 0.121 mol) was added and stirred at room temperature for 2 hours, followed by addition of methanol (1.0 mL) and stirring for an additional 30 minutes. Insoluble materials were filtered off, and the filtrate was concentrated. The resulting residue was purified by silica gel column chromatography (hexane:ethyl acetate=95:5) to give compound (A2) (30.2 g, 85%) as a colorless oil.

$^1$H NMR (200 MHz, CHLOROFORM-d) δ ppm 1.21 (d, J=7.03 Hz, 6H) 2.84 (sept, J=7.03 Hz, 1H) 5.14 (s, 2H) 6.62 (dd, J=8.35, 2.20 Hz, 1H) 6.74 (d, J=2.20 Hz, 1H) 7.23-7.58 (m, 5H) 7.68 (d, J=8.35 Hz, 1H).

(3) Reference Example 1-3

Compound (A3)

[Chem. 12]

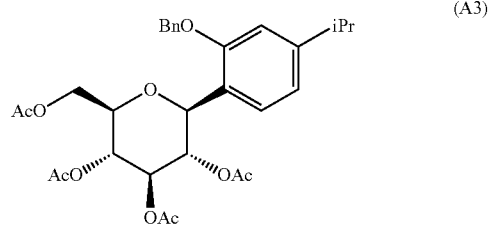

To a solution of compound (A2) (30.2 g, 85.7 mmol) in THF (450 mL), 2.6 M n-butyllithium in hexane (33 mL, 85.7 mmol) was added dropwise at −78° C. under a nitrogen atmosphere and stirred at the same temperature for 15 minutes. Then, a solution of 2,3,4,6-tetra-O-trimethylsilyl-D-glucono-1,5-lactone (40.0 g, 85.7 mmol) in THF (230 mL) was added dropwise over 15 minutes and stirred at the same temperature for 20 minutes. To the reaction mixture, saturated aqueous ammonium chloride (150 mL) and water (100 mL) were added. This mixture was warmed to room temperature and then extracted twice with ethyl acetate. The combined organic layers were washed with brine and dried over anhydrous magnesium sulfate. After filtering off the desiccant, the solvent was distilled off under reduced pressure.

The resulting residue was dissolved in a solution containing methanesulfonic acid (2.9 g) in methanol (840 mL), and stirred at room temperature for 14.5 hours. After neutralization with triethylamine (2.5 mL), the reaction mixture was concentrated.

The resulting residue (46.4 g) was dissolved in pyridine (125 mL) and cooled to 4° C. To this solution, acetic anhydride (75 mL) and 4-dimethylaminopyridine (102 mg, 0.835 mmol) were added and stirred at room temperature for 19 hours. After addition of ice-cold water (500 mL), the mixture was extracted twice with ethyl acetate (500 mL). The combined organic layers were washed with saturated aqueous sodium bicarbonate and brine, and then dried over anhydrous magnesium sulfate. After filtering off the desiccant, the solvent was distilled off under reduced pressure to give a crude compound (53 g).

To a solution of this crude compound in chloroform (250 mL) and acetonitrile (250 mL), Et$_3$SiH (13.7 mL, 85.7 mmol) and BF$_3$.Et$_2$O (10.9 mL, 85.7 mmol) were added at 4° C. under a nitrogen atmosphere, and stirred at the same temperature for 1.5 hours. The reaction mixture was diluted with saturated aqueous sodium bicarbonate and extracted with chloroform. The organic layer was washed with brine and dried over anhydrous magnesium sulfate. After filtering off the desiccant, the solvent was distilled off under reduced pressure and the resulting residue was purified by silica gel column chromatography (hexane:ethyl acetate=5:1→2:1) to give compound (A3) (19.1 g, 40%; 4 steps) as a light-yellow amorphous substance.

$^1$H NMR (300 MHz, CHLOROFORM-d) δ ppm 1.21 (d, J=6.99 Hz, 6H) 1.78 (s, 3H) 2.01 (s, 6H) 2.05 (s, 3H) 2.86 (sept, J=6.99 Hz, 1H) 3.80 (ddd, J=9.95, 4.59, 2.25 Hz, 1H) 4.06-4.13 (m, 1H) 4.19-4.27 (m, 1H) 4.96 (d, J=9.95 Hz, 1H) 5.10 (s, 2H) 5.16-5.25 (m, 1H) 5.33 (t, J=9.17 Hz, 1H) 5.40-5.49 (m, 1H) 6.79 (d, J=1.40 Hz, 1H) 6.85 (dd, J=7.93, 1.40 Hz, 1H) 7.26-7.52 (m, 6H)

MS ESI/APCI Dual posi: 579[M+Na]$^+$..

(4) Reference Example 1-4

Compound (A4)

[Chem. 13]

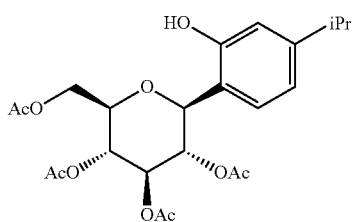

To a solution of compound (A3) (19.1 g, 34.3 mmol) in methanol (200 mL), 10% palladium on activated carbon (1.8 g) was added and stirred under a hydrogen atmosphere at room temperature for 2 hours. After the reaction mixture was filtered through celite, the solvent was distilled off under reduced pressure and the resulting residue was purified by silica gel column chromatography (hexane:ethyl acetate=2:1→1:1) to give compound (A4) (12.3 g, 77%) as a colorless amorphous substance.

$^1$H NMR (300 MHz, CHLOROFORM-d) δ ppm 1.20 (d, J=6.89 Hz, 6H) 1.83 (s, 3H) 2.01 (s, 3H) 2.06 (s, 3H) 2.12 (s, 3H) 2.82 (sept, J=6.89 Hz, 1H) 3.87 (ddd, J=9.60, 3.85, 2.25 Hz, 1H) 4.14-4.21 (m, 1H) 4.27-4.36 (m, 1H) 4.59 (d, J=9.33 Hz, 1H) 5.23-5.39 (m, 3H) 6.70 (dd, J=7.93, 1.71 Hz, 1H) 6.77 (d, J=1.71 Hz, 1H) 6.80 (s, 1H) 6.91 (d, J=7.93 Hz, 1H).

MS ESI/APCI Dual posi: 489[M+Na]$^+$.
MS ESI/APCI Dual nega: 501[M+Cl]$^-$.

(5) Reference Example 1-5

Compound (A5)

[Chem. 14]

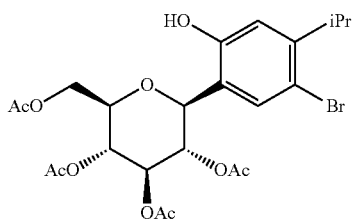

To a solution of compound (A4) (12.3 g, 26.3 mmol) in acetic acid (120 mL), bromine (4.2 g, 26.3 mmol) was added dropwise at room temperature. The reaction mixture was stirred for 1.5 hours, and ice-cold water (150 mL) was added thereto. This mixture was extracted twice with ethyl acetate, and the combined organic layers were washed with saturated aqueous sodium bicarbonate, 10% aqueous sodium thiosulfate and brine, and then dried over anhydrous magnesium sulfate. After filtering off the desiccant, the solvent was distilled off under reduced pressure. The resulting residue was dissolved in 2-propanol (20 mL), to which hexane (50 mL) was then added dropwise. The mixture was stirred at 4° C. for 1 hour, and the resulting precipitate was filtered to give compound (A5) (9.8 g, 68%) as a colorless powder.

$^1$H NMR (300 MHz, CHLOROFORM-d) δ ppm 1.12-1.26 (m, 6H) 1.89 (s, 3H) 2.01 (s, 3H) 2.07 (s, 3H) 2.13 (s, 3H) 3.22 (sept, J=6.74 Hz, 1H) 3.87 (ddd, J=9.48, 3.73, 2.18 Hz, 1H) 4.14-4.22 (m, 1H) 4.28-4.36 (m, 1H) 4.53 (d, J=9.33 Hz, 1H) 5.16-5.39 (m, 3H) 6.82 (s, 1H) 7.14 (s, 1H).

MS ESI/APCI Dual posi: 567[M+Na]$^+$, 569[M+2+Na]$^+$.
MS ESI/APCI Dual nega: 579[M+Cl]$^-$, 581[M+2+Cl]$^-$.

(6) Reference Example 1-6

Compound (A6)

[Chem. 15]

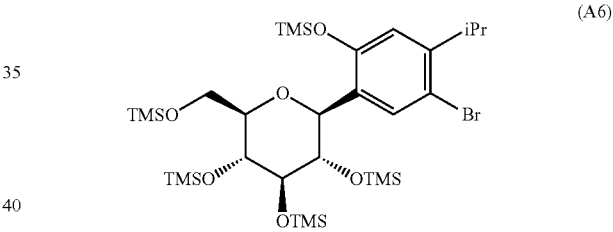

To a solution of compound (A5) (12.2 g, 22.3 mmol) in methanol (120 mL), triethylamine (24 mL) and water (24 mL) were added. The reaction mixture was stirred at room temperature for 15 hours and further stirred at 50° C. for 10 hours, followed by distilling off the solvent under reduced pressure.

The resulting residue was dissolved in N,N-dimethylformamide (106 mL), to which triethylamine (18.6 mL, 134 mmol) and chlorotrimethylsilane (14.3 mL, 112 mmol) were then added at 4° C. under a nitrogen atmosphere. The reaction mixture was stirred at 4° C. for 1 hour, followed by addition of ice-cold water (150 mL) This mixture was extracted three times with toluene, and the combined organic layers were washed with water, saturated aqueous sodium bicarbonate and brine, and then dried over anhydrous magnesium sulfate. After filtering off the desiccant, the solvent was distilled off under reduced pressure to give compound (A6) (17.4 g) as an oil. This compound was used for the next reaction without purification.

$^1$H NMR (300 MHz, CHLOROFORM-d) δ ppm −0.28 (s, 9H) 0.08 (s, 9H) 0.19 (s, 9H) 0.20 (s, 9H) 0.29 (s, 9H) 1.16 (d, J=6.84 Hz, 3H) 1.21 (d, J=6.84 Hz, 3H) 3.17-3.37 (m, 1H) 3.41-3.56 (m, 3H) 3.62-3.72 (m, 1H) 3.76-3.86 (m, 1H) 4.46 (d, J=8.24 Hz, 1H) 6.64 (s, 1H) 7.47 (s, 1H).

(7) Reference Example 1-7

Compound (A7)

[Chem. 16]

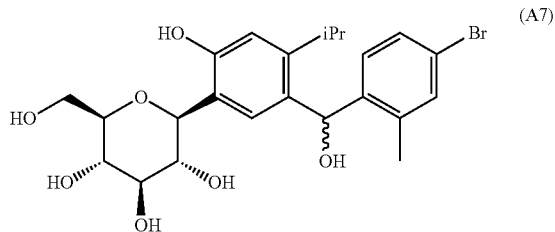

To a solution of compound (A6) (13.4 g, 15.9 mmol) in THF (140 mL), 2.6 M n-butyllithium in hexane (7.7 mL, 20.0 mmol) was added dropwise over 10 minutes at −78° C. under a nitrogen atmosphere and stirred at the same temperature for 5 minutes. Then, a solution of 4-bromo-2-methylbenzaldehyde (3.2 g, 15.9 mmol) in THF (24 mL) was added dropwise over 15 minutes and stirred at the same temperature for 45 minutes. To the reaction mixture, saturated aqueous ammonium chloride (100 mL) and water (100 mL) were added. This mixture was warmed to room temperature and then extracted twice with ethyl acetate. The combined organic layers were washed with brine and dried over anhydrous magnesium sulfate. After filtering off the desiccant, the solvent was distilled off under reduced pressure.

The resulting residue was dissolved in a solution containing methanesulfonic acid (0.9 g) in methanol (200 mL), and stirred at room temperature for 0.5 hours. After neutralization with triethylamine, the reaction mixture was concentrated. The resulting residue was purified by silica gel column chromatography (chloroform:methanol=10:1→8:1) to give compound (A7) (5.75 g, 73%) as a colorless amorphous substance.

$^1$H NMR (600 MHz, METHANOL-$d_4$) δ ppm 1.01 and 1.04 (each d, J=6.88 Hz, 3H) 1.18 and 1.19 (each d, J=6.88 Hz, 3H) 2.24 and 2.26 (each s, 3H) 2.95-3.07 (m, 1H) 3.35-3.69 (m, 5H) 3.78-3.87 (m, 1H) 4.37-4.50 (m, 1H) 5.59 (s, 1H) 6.80 (s, 1H) 6.98-7.10 (m, 2H) 7.24-7.30 (m, 1H) 7.33 (s, 1H).

MS ESI/APCI Dual posi: 479[M-OH]$^+$, 481[M+2-OH]$^+$.

(8) Reference Example 1-8

Intermediate (A)

[Chem. 17]

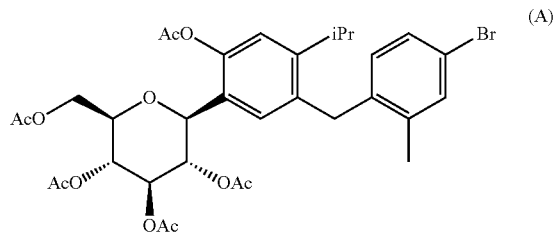

Compound (A7) (5.7 g, 11.5 mmol) was dissolved in pyridine (34 mL). To this solution, acetic anhydride (17 mL) and 4-dimethylaminopyridine (10 mg) were added and stirred at room temperature for 0.5 hours. After addition of ice-cold water (500 mL), the mixture was extracted twice with ethyl acetate (500 mL) The combined organic layers were washed with saturated aqueous sodium bicarbonate and brine, and then dried over anhydrous magnesium sulfate. After filtering off the desiccant, the solvent was distilled off under reduced pressure to give a crude compound (8.5 g).

To a solution of this crude compound (8.5 g) in chloroform (80 mL) and acetonitrile (80 mL), Et$_3$SiH (2.7 mL, 17.0 mmol) and BF$_3$.Et$_2$O (2.2 mL, 17.0 mmol) were added at 4° C. under a nitrogen atmosphere. The reaction mixture was warmed to room temperature and then stirred at the same temperature for 0.5 hours. The reaction mixture was diluted with saturated aqueous sodium bicarbonate and extracted with chloroform. The organic layer was washed with brine and dried over anhydrous magnesium sulfate. After filtering off the desiccant, the solvent was distilled off under reduced pressure. The resulting residue was crystallized from a 4:1 hexane:ethyl acetate mixture, and the resulting precipitate was filtered to give intermediate (A) (5.3 g, 68%) as a colorless powder.

$^1$H NMR (300 MHz, CHLOROFORM-d) δ ppm 1.12 (d, J=6.68 Hz, 3H) 1.14 (d, J=6.68 Hz, 3H) 1.76 (s, 3H) 1.99 (s, 3H) 2.03 (s, 3H) 2.06 (s, 3H) 2.27 (s, 3H) 2.37 (s, 3H) 2.93 (sept, J=6.68 Hz, 1H) 3.76 (ddd, J=9.87, 4.51, 2.25 Hz, 1H) 3.87 (s, 2H) 4.06 (dd, J=12.51, 2.25 Hz, 1H) 4.27 (dd, J=12.51, 4.51 Hz, 1H) 4.49 (d, J=9.64 Hz, 1H) 5.10-5.33 (m, 3H) 6.59 (d, J=8.39 Hz, 1H) 6.97 (s, 1H) 7.00 (s, 1H) 7.20 (dd, J=8.39, 2.49 Hz, 1H) 7.34 (d, J=2.49 Hz, 1H).

MS ESI/APCI Dual posi: 713[M+Na]$^+$, 715[M+2+Na]$^+$.

Alternatively, intermediate (A) can also be synthesized as described in Reference Examples 1-9, 1-10 and 1-11 below.

(9) Reference Example 1-9

Compound (A8)

[Chem. 18]

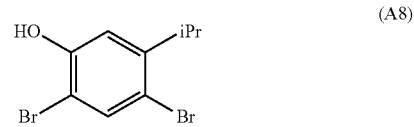

To a solution of 3-isopropylphenol (160 g, 1.18 mol) in acetic acid (1.6 L), a solution of bromine (469 g, 2.94 mol) in acetic acid (320 mL) was added dropwise over 32 minutes under ice cooling such that the internal temperature did not exceed 19° C., followed by stirring at room temperature for 1 hour. After addition of toluene (1.6 L), 10% aqueous sodium sulfite (1.0 L) was added dropwise under ice cooling such that the internal temperature did not exceed 20° C. The organic layer was separated and washed twice with 10% aqueous sodium sulfite (1.0 L) and 10% aqueous sodium chloride (1.0 L), and then dried over anhydrous magnesium sulfate. After filtering off the desiccant, the solvent was distilled off under reduced pressure to give compound (A8) (342 g, 99%) as a light-yellow oil.

$^1$H NMR (300 MHz, CHLOROFORM-d) δ ppm 1.21 (d, J=6.84 Hz, 6H) 3.25 (sept, J=6.84 Hz, 1H) 5.40 (s, 1H) 6.96 (s, 1H) 7.61 (s, 1H).

(10) Reference Example 1-10

Compound (A9)

[Chem. 19]

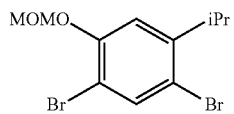

To a solution of compound (A8) (512 g, 1.74 mol) in chloroform (1.74 L), diisopropylethylamine (364 mL, 2.09 mol) was added and cooled on ice. Chloromethyl methyl ether (159 mL, 2.09 mol) was added dropwise over 60 minutes and stirred at room temperature for 1 hour. The reaction mixture was cooled on ice, and 1 M aqueous sodium hydroxide (1.5 L) was added dropwise thereto. The organic layer was separated and washed with 1 M aqueous sodium hydroxide (1.5 L) and water (1.5 L), and then dried over anhydrous magnesium sulfate. After filtering off the desiccant, the solvent was distilled off under reduced pressure. The resulting residue was purified by distillation under reduced pressure (0.93 to 1.5 hpa, 122° C. to 137° C.) to give compound (A9) (548 g, 96%) as a light-yellow oil.

$^1$H NMR (300 MHz, CHLOROFORM-d) δ ppm 1.22 (d, J=6.84 Hz, 6H) 3.28 (sept, J=6.84 Hz, 1H) 3.52 (s, 3H) 5.23 (s, 2H) 7.06 (s, 1H) 7.69 (s, 1H).

MS ESI/APCI Dual posi: 339[M+H]$^+$, 341[M+2+H]$^+$.

(11) Reference Example 1-11

Intermediate (A)

To a solution of compound (A9) (210 g, 0.621 mol) in THF (3.1 L), 2.76 M n-butyllithium in hexane (236 mL, 0.652 mol) was added dropwise over 20 minutes at −86° C. to −74° C. under an argon atmosphere, and stirred at the same temperature for 35 minutes. Then, a solution of 2,3,4,6-tetra-O-trimethylsilyl-D-glucono-1,5-lactone (305 g, 0.652 mol) in THF (890 mL) was added dropwise over 38 minutes and stirred at the same temperature for 50 minutes. Further, trimethylchlorosilane (82.8 mL, 0.652 mmol) was added dropwise over 4 minutes and stirred at the same temperature for 3 hours. Then, 2.76 M n-butyllithium in hexane (326 mL, 0.901 mol) was added dropwise over 23 minutes and stirred at the same temperature for 40 minutes. Finally, a solution of 4-bromo-2-methylbenzaldehyde (136 g, 0.683 mmol) in THF (890 mL) was added dropwise over 43 minutes and stirred at the same temperature for 35 minutes. The reaction mixture was diluted with water (3.1 L) and warmed to room temperature. After addition of toluene (3.1 L), the organic layer was separated and the solvent was distilled off under reduced pressure.

The resulting residue (633 g) was dissolved in methanol (3.1 L), and methanesulfonic acid (4.03 mL, 0.0621 mol) was added thereto, followed by heating under reflux for 1 hour. The reaction mixture was cooled to room temperature, neutralized with triethylamine (17.3 mL, 0.124 mol) and then concentrated. The concentrated product (413 g) was dissolved in toluene (1.1 L) and washed three times with water (1.65 L). The organic layer was diluted with toluene (0.55 L) and extracted with 1 M aqueous sodium hydroxide (0.55 L). The aqueous layer was washed with toluene (1.65 L) and acidified by addition of 2 M aqueous hydrochloric acid (0.43 L). The resulting aqueous layer was extracted with toluene (1.1 L). The organic layer was washed with 10% aqueous sodium chloride (1.1 L), followed by distilling off the solvent under reduced pressure.

The resulting residue (273 g) was dissolved in THF (1.01 L). To this solution, diisopropylethylamine (776 mL, 4.53 mol), acetic anhydride (381 mL, 4.03 mol) and 4-dimethylaminopyridine (615 mg, 5.04 mmol) were added and stirred at room temperature for 21 hours. The reaction mixture was cooled on ice, and water (1.0 L) and toluene (1.0 L) were added thereto. The organic layer was separated and washed with saturated aqueous sodium bicarbonate (1.0 L), followed by distilling off the solvent under reduced pressure.

The resulting residue (390 g) was dissolved in acetonitrile (3.85 L). To this solution, water (9.07 mL, 0.504 mol) and t-BuMe$_2$SiH (334 mL, 2.02 mol) were added and cooled on ice, followed by dropwise addition of TMSOTf (392 mL, 2.17 mol) over 30 minutes. After stirring at the same temperature for 1 hour, acetic anhydride (95.2 mL, 1.01 mol) was added dropwise over 10 minutes and stirred at the same temperature for an additional 15 minutes. To the reaction mixture, toluene (3.85 mL) and 3% aqueous sodium bicarbonate (1.92 L) were added. The organic layer was separated and washed with 3% aqueous sodium bicarbonate (1.92 L) and 10% aqueous sodium chloride (1.92 L), and then dried over anhydrous magnesium sulfate. After filtering off the desiccant, the solvent was distilled off under reduced pressure and the resulting residue was crystallized from 2-propanol (1.42 L). The resulting precipitate was filtered to give intermediate (A) (201 g, 47%; 4 steps) as a colorless powder.

Reference Example 2

Preparation of Intermediate (B)

[Chem. 20]

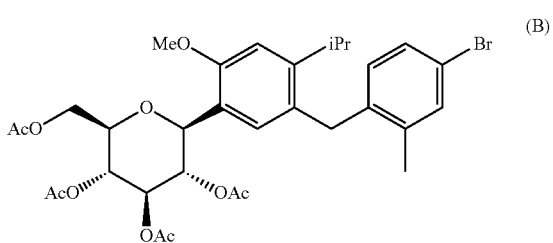

(1) Reference Example 2-1

Compound (B1)

[Chem. 21]

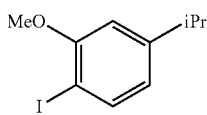

To a suspension of compound (A1) (27.4 g, 0.104 mol) and potassium carbonate (21.7 g, 0.156 mol) in acetonitrile (200 mL), methyl iodide (9.8 mL, 0.156 mol) was added and stirred at 40° C. for 2.5 hours. Additional methyl iodide (3.5 mL, 0.052 mol) was further added and stirred at the same temperature for 1 hour. Insoluble materials were filtered off, and the filtrate was diluted with ethyl acetate. The organic layer was washed with water, 10% aqueous sodium thiosulfate and brine, and then dried over anhydrous magnesium sulfate. After filtering off the desiccant, the solvent was distilled off under reduced pressure. The resulting residue was purified by silica gel column chromatography (hexane→hexane:ethyl acetate=95:5) to give compound (B1) (24.5 g, 85%) as a light-yellow oil.

$^1$H NMR (300 MHz, CHLOROFORM-d) δ ppm 1.24 (d, J=6.84 Hz, 6H) 2.87 (sept, J=6.84 Hz, 1H) 3.88 (s, 3H) 6.58-6.65 (m, 1H) 6.70 (d, J=1.87 Hz, 1H) 7.65 (d, J=8.08 Hz, 1H).

MS ESI/APCI Dual posi: 277[M+H]$^+$.

(2) Reference Example 2-2

Compound (B2)

[Chem. 22]

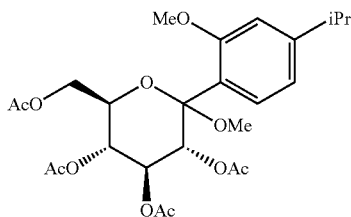

To a solution of compound (B1) (24.5 g, 88.6 mmol) in THF (100 mL), 2.6 M n-butyllithium in hexane (34 mL, 88.6 mmol) was added dropwise at −78° C. under a nitrogen atmosphere and stirred at the same temperature for 5 minutes. Then, a solution of 2,3,4,6-tetra-O-trimethylsilyl-D-glucono-1,5-lactone (37.6 g, 80.5 mmol) in THF (60 mL) was added dropwise over 25 minutes and stirred at the same temperature for 10 minutes. To the reaction mixture, ice and water were added, and the mixture was warmed to room temperature and then extracted with ethyl acetate. The combined organic layers were washed with brine and dried over anhydrous magnesium sulfate. After filtering off the desiccant, the solvent was distilled off under reduced pressure.

The resulting residue was dissolved in a solution containing methanesulfonic acid (1.55 g, 16.1 mmol) in methanol (380 mL) and stirred at room temperature for 2 hours. After neutralization with triethylamine (11.2 mL, 80.5 mmol), the reaction mixture was concentrated.

The resulting residue (30.2 g) was dissolved in pyridine (100 mL). To this solution, acetic anhydride (100 mL) was added and stirred at room temperature for 14 hours. After addition of ice-cold water (400 mL), the mixture was extracted twice with ethyl acetate (200 mL). The combined organic layers were washed with 1 M aqueous hydrochloric acid, saturated aqueous sodium bicarbonate and brine, and then dried over anhydrous magnesium sulfate. After filtering off the desiccant, the solvent was distilled off under reduced pressure and the resulting residue was purified by silica gel column chromatography (hexane→hexane:ethyl acetate=6:4) to give compound (B2) (32.8 g, 80%; 3 steps) as a light-yellow oil.

$^1$H NMR (300 MHz, CHLOROFORM-d) δ ppm 1.23 (d, J=6.92 Hz, 6H) 1.84 (s, 3H) 1.97 (s, 3H) 2.06 (s, 3H) 2.10 (s, 3H) 2.87 (sept, J=6.92 Hz, 1H) 3.32 (s, 3H) 3.87 (s, 3H) 4.04 (ddd, J=10.18, 4.74, 2.41 Hz, 1H) 4.17-4.23 (m, 1H) 4.28-4.36 (m, 1H) 5.25 (dd, J=10.18, 9.40 Hz, 1H) 5.36 (d, J=10.18 Hz, 1H) 5.60 (dd, J=10.18, 9.40 Hz, 1H) 6.74 (d, J=1.55 Hz, 1H) 6.79 (dd, J=8.08, 1.55 Hz, 1H) 7.26-7.33 (m, 1H).

MS ESI/APCI Dual posi: 533[M+Na]$^+$.

(3) Reference Example 2-3

Compound (B3)

[Chem. 23]

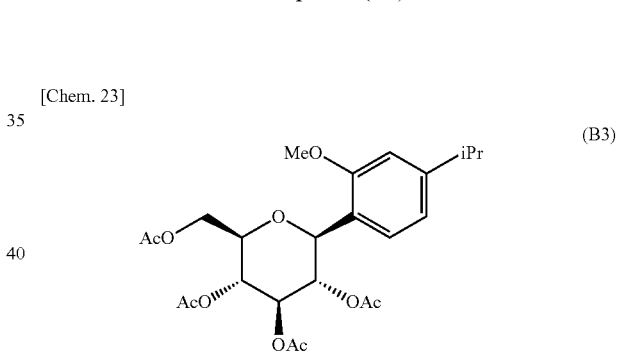

To a solution of compound (B2) (32.8 g, 64.0 mmol) in chloroform (150 mL) and acetonitrile (150 mL), Et$_3$SiH (21 mL, 128 mmol) and BF$_3$.Et$_2$O (49 mL, 385 mmol) were added at 4° C. under a nitrogen atmosphere and stirred at the same temperature for 1 hour. The reaction mixture was diluted with saturated aqueous sodium bicarbonate and extracted with chloroform. The organic layer was washed with brine and dried over anhydrous magnesium sulfate. After filtering off the desiccant, the solvent was distilled off under reduced pressure and the resulting residue was purified by silica gel column chromatography (hexane:ethyl acetate=2:1) to give compound (B3) (22.9 g, 74%) as a light-yellow gum.

$^1$H NMR (300 MHz, CHLOROFORM-d) δ ppm 1.22 (d, J=6.99 Hz, 6H) 1.77 (s, 3H) 2.01 (s, 3H) 2.05 (s, 3H) 2.07 (s, 3H) 2.87 (sept, J=6.96 Hz, 1H) 3.80-3.87 (m, 1H) 3.84 (s, 3H) 4.09-4.16 (m, 1H) 4.22-4.29 (m, 1H) 4.88-4.95 (m, 1H) 5.18-5.27 (m, 1H) 5.32-5.38 (m, 2H) 6.71 (d, J=1.55 Hz, 1H) 6.83 (dd, J=7.93, 1.55 Hz, 1H) 7.23-7.30 (m, 1H).

MS ESI/APCI Dual posi: 503[M+H]$^+$.

MS ESI/APCI Dual nega: 515[M+Cl]$^-$.

(4) Reference Example 2-4

Compound (B4)

[Chem. 24]

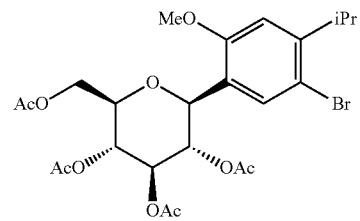

The same procedure as shown in Reference Example 1-5 was repeated to give compound (B4) (25.5 g, 96%) as a light-yellow amorphous substance, except that compound (A4) was replaced by compound (B3).

$^1$H NMR (300 MHz, CHLOROFORM-d) δ ppm 1.20 (d, J=6.84 Hz, 3H) 1.23 (d, J=6.84 Hz, 3H) 1.80 (s, 3H) 2.01 (s, 3H) 2.05 (s, 3H) 2.09 (s, 3H) 3.31 (sept, J=6.84 Hz, 1H) 3.77-3.82 (m, 1H) 3.83 (s, 3H) 4.10-4.17 (m, 1H) 4.22-4.30 (m, 1H) 4.83 (d, J=9.48 Hz, 1H) 5.17-5.38 (m, 3H) 6.75 (s, 1H) 7.49 (s, 1H).

MS ESI/APCI Dual posi: 581[M+Na]$^+$, 583[M+2+Na]$^+$.

(5) Reference Example 2-5

Compound (B5)

[Chem. 25]

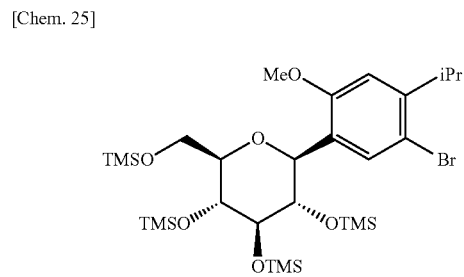

The same procedure as shown in Reference Example 1-6 was repeated to give compound (B5) (30.3 g) as a brown oil, except that compound (A5) was replaced by compound (B4). This compound was used for the next reaction without purification.

$^1$H NMR (300 MHz, CHLOROFORM-d) δ ppm −0.32 (s, 9H) 0.09 (s, 9H) 0.18 (s, 9H) 0.20 (s, 9H) 1.19 (d, J=6.84 Hz, 3H) 1.23 (d, J=6.84 Hz, 3H) 3.26-3.44 (m, 3H) 3.52-3.58 (m, 2H) 3.65-3.75 (m, 3H) 3.76-3.83 (m, 1H) 3.80 (s, 3H) 4.60 (d, J=8.55 Hz, 1H) 6.72 (s, 1H) 7.51 (s, 1H).

MS ESI/APCI Dual posi: 701[M+Na]$^+$, 703[M+2+Na]$^+$.

(6) Reference Example 2-6

Compound (B6)

[Chem. 26]

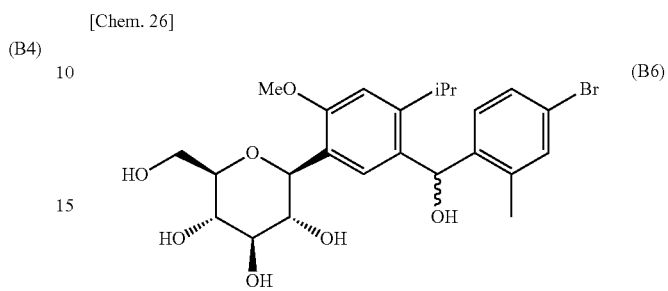

The same procedure as shown in Reference Example 1-7 was repeated to give compound (B6) (14.7 g, 60%) as a brown amorphous substance, except that compound (A6) was replaced by compound (B5).

$^1$H NMR (300 MHz, CHLOROFORM-d) δ ppm 1.23 and 1.25 (each d, J=6.84 Hz, 6H) 1.80 (s, 2H) 2.27 and 2.29 (each s, 3H) 2.30-2.58 (m, 2H) 2.82-3.06 (m, 2H) 3.34 and 3.35 (each s, 3H) 3.38-3.86 (m, 6H) 4.56-4.73 (m, 1H) 5.53 (d, J=3.11 Hz, 1H) 6.75-7.35 (m, 5H).

MS ESI/APCI Dual posi: 493[M−OH]$^+$, 495[M+2−OH]$^+$

(7) Reference Example 2-7

Intermediate (B)

[Chem. 27]

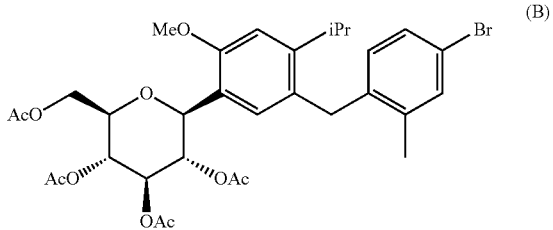

The same procedure as shown in Reference Example 1-8 was repeated to give intermediate (B) (14.2 g, 88%) as a colorless amorphous substance, except that compound (A7) was replaced by compound (B6).

$^1$H NMR (300 MHz, CHLOROFORM-d) δ ppm 1.11 (d, J=6.68 Hz, 3H) 1.14 (d, J=6.68 Hz, 3H) 1.75 (s, 3H) 1.99 (s, 3H) 2.04 (s, 3H) 2.05 (s, 3H) 2.28 (s, 3H) 2.90 (sept, J=6.68 Hz, 1H) 3.71-3.90 (m, 3H) 3.86 (s, 3H) 3.85-3.87 (m, 1H) 4.05-4.15 (m, 1H) 4.19-4.28 (m, 1H) 4.77-4.85 (m, 1H) 5.11-5.23 (m, 1H) 5.26-5.37 (m, 2H) 6.54 (d, J=8.24 Hz, 1H) 6.81 (s, 1H) 6.96 (s, 1H) 7.17 (dd, J=8.24, 2.64 Hz, 1H) 7.32 (d, J=2.64 Hz, 1H).

MS ESI/APCI Dual posi: 685[M+Na]$^+$, 687[M+2+Na]$^+$

Reference Example 3

Preparation of Intermediate (C)

[Chem. 28]

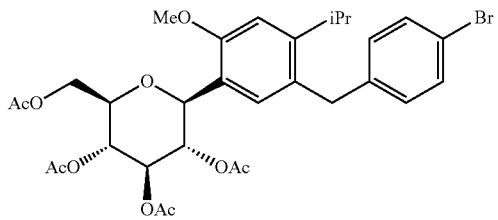
(C)

The same procedures as shown in Reference Examples 1-7 and 1-8 were repeated to give compound (C) (2.26 g) as a light-yellow amorphous substance, except that compound (A6) was replaced by compound (B5), and 4-bromo-2-methylbenzaldehyde was replaced by 4-bromobenzaldehyde.

$^1$H NMR (300 MHz, CHLOROFORM-d) δ ppm 1.04 (d, J=6.84 Hz, 3H) 1.09 (d, J=6.84 Hz, 3H) 1.76 (s, 3H) 2.01 (s, 3H) 2.05 (s, 3H) 2.06 (s, 3H) 2.91-3.06 (m, 1H) 3.80-3.88 (m, 4H) 3.91 (d, J=5.13 Hz, 2H) 4.06-4.18 (m, 1H) 4.20-4.31 (m, 1H) 4.82-4.93 (m, 1H) 5.15-5.43 (m, 3H) 6.77 (s, 1H) 6.92 (d, J=8.55 Hz, 2H) 7.11 (s, 1H) 7.36 (d, J=8.55 Hz, 2H).

Reference Example 4

Preparation of Intermediate (D)

[Chem. 29]

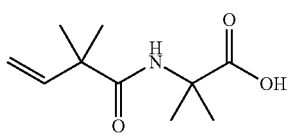
(D)

(1) Reference Example 4-1

Compound (D1)

[Chem. 30]

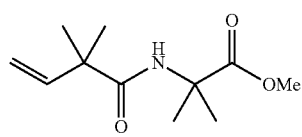
(D1)

To a solution of 2,2-dimethyl-3-butenoic acid (J. Org. Chem., vol. 65, p. 8402, 2000) (5.42 g, 47.5 mmol) in chloroform (250 mL), oxalyl chloride (4.43 mL, 49.9 mmol) and N,N-dimethylformamide (3 drops) were added under a nitrogen atmosphere and stirred at room temperature for 1.5 hours. The reaction mixture was then cooled on ice, and triethylamine (19.9 mL, 143 mmol) and α-aminoisobutyric acid methyl ester hydrochloride (10.9 g, 71.2 mmol) were added thereto, followed by stirring at room temperature for 1 hour. The reaction mixture was diluted with water and extracted with chloroform. The organic layer was washed with 3 M aqueous hydrochloric acid, saturated aqueous sodium bicarbonate and brine, and then dried over anhydrous magnesium sulfate. After filtering off the desiccant, the solvent was distilled off under reduced pressure and the resulting residue was purified by silica gel column chromatography (hexane→hexane:ethyl acetate=4:1) to give compound (D1) (9.38 g, 93%) as a colorless powder.

$^1$H NMR (300 MHz, CHLOROFORM-d) δ ppm 1.27 (s, 6H) 1.51 (s, 6H) 3.73 (s, 3H) 5.17-5.32 (m, 2H) 6.02 (dd, J=17.56, 10.57 Hz, 1H) 6.25 (br. s., 1H).

MS ESI/APCI Dual posi: 214[M+H]$^+$.

(2) Reference Example 4-2

Intermediate (D)

[Chem. 31]

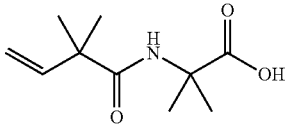
(D)

To a solution of compound (D1) (9.38 g, 43.9 mmol) in methanol (20 mL), 4 M aqueous sodium hydroxide (16.5 mL, 66.0 mmol) was added and stirred at room temperature for 1 hour. Then, the reaction mixture was concentrated. The resulting residue was dissolved in water and neutralized with 3 M aqueous hydrochloric acid. This mixture was extracted with ethyl acetate, and the combined organic layers were washed with brine and dried over anhydrous magnesium sulfate. After filtering off the desiccant, the solvent was distilled off under reduced pressure to give intermediate (D) (8.19 g, 94%) as a colorless powder.

$^1$H NMR (300 MHz, CHLOROFORM-d) δ ppm 1.29 (s, 6H) 1.54 (s, 6H) 5.16-5.36 (m, 2H) 6.01 (dd, J=17.49, 10.65 Hz, 1H) 6.14 (s, 1H).

MS ESI/APCI Dual posi: 200[M+H]$^+$, 222[M+Na]$^+$.

MS ESI/APCI Dual nega: 198[M−H]$^-$.

Reference Example 5

Preparation of Intermediate (E)

[Chem. 32]

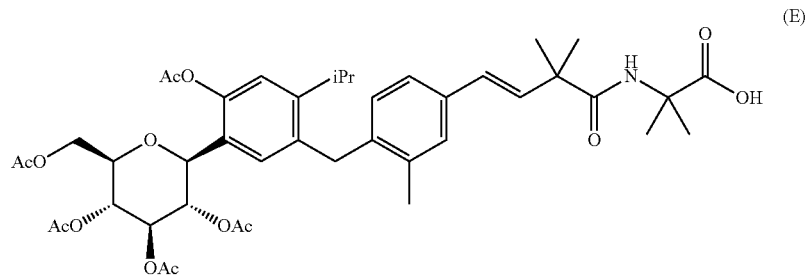

Under an argon atmosphere, a suspension of intermediate (A) (5.0 g, 7.23 mmol), intermediate (D) (2.59 g, 13.0 mmol), palladium(II) acetate (328 mg, 1.45 mmol), tri-O-tolylphosphine (880 mg, 2.89 mmol) and triethylamine (3.0 mL, 9.00 mmol) in acetonitrile (24 mL) was stirred at 120° C. for 20 minutes under microwave irradiation. The reaction mixture was filtered through celite and washed with ethyl acetate. The filtrate was concentrated under reduced pressure and the resulting residue was purified by silica gel column chromatography (hexane:ethyl acetate=1:1→ethyl acetate) to give intermediate (E) (4.59 g, 78%) as a light-yellow powder.

$^1$H NMR (300 MHz, CHLOROFORM-d) δ ppm 1.16, 1.18 (each d, J=6.84 Hz, each 3H) 1.40 (s, 6H) 1.54-1.58 (m, 6H) 1.76 (s, 3H) 1.99 (s, 3H) 2.03 (s, 3H) 2.05 (s, 3H) 2.28 (s, 3H) 2.36 (s, 3H) 2.98-3.10 (m, 1H) 3.71-3.79 (m, 1H) 3.94 (s, 2H) 4.01-4.08 (m, 1H) 4.24 (dd, J=12.43, 4.51 Hz, 1H) 4.47 (d, J=9.17 Hz, 1H) 5.07-5.32 (m, 3H) 6.31 (d, J=16.32 Hz, 1H) 6.35 (s, 1H) 6.55 (d, J=16.32 Hz, 1H) 6.77 (d, J=7.62 Hz, 1H) 6.92 (s, 1H) 6.99 (s, 1H) 7.12-7.18 (m, 1H) 7.26 (s, 1H).

MS ESI/APCI Dual posi: 810[M+H]$^+$, 832[M+Na]$^+$.
MS ESI/APCI Dual nega: 808[M−H]$^−$.

Reference Example 6

Preparation of Intermediate (F)

[Chem. 33]

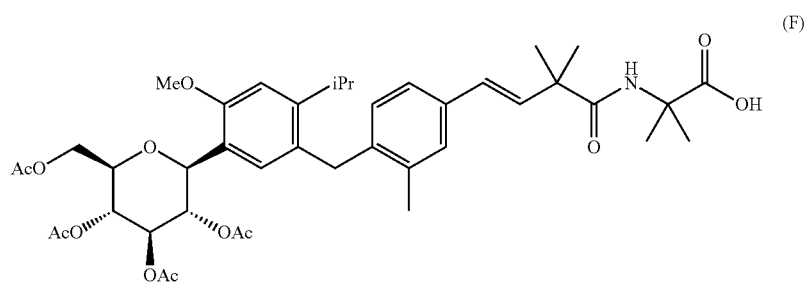

The same procedure as shown in Reference Example 5 was repeated to give intermediate (F) (2.03 g, 87%) as a yellow powder, except that intermediate (A) was replaced by intermediate (B).

$^1$H NMR (300 MHz, CHLOROFORM-d) δ ppm 1.17, 1.14 (each d, J=6.99 Hz, 3H) 1.38 (s, 6H) 1.55 (s, 6H) 1.76 (s, 3H) 1.98 (s, 3H) 2.04 (s, 6H) 2.30 (s, 3H) 2.94-3.03 (m, 1H) 3.76-3.83 (m, 1H) 3.84-3.95 (m, 4H) 4.06-4.15 (m, 1H) 4.16-4.25 (m, 1H) 4.81 (d, J=9.79 Hz, 1H) 5.12-5.20 (m, 1H) 5.23-5.35 (m, 2H) 6.29 (s, 1H) 6.31 (d, J=16.32 Hz, 1H) 6.52 (d, J=16.32 Hz, 1H) 6.67 (d, J=8.08 Hz, 1H) 6.81 (s, 1H) 6.94 (s, 1H) 7.06-7.14 (m, 1H) 7.24 (s, 1H).

MS ESI/APCI Dual posi: 782[M+H]$^+$, 804[M+Na]$^+$.
MS ESI/APCI Dual nega: 780[M−H]$^−$.

Reference Example 7

Preparation of Intermediate (G)

[Chem. 34]

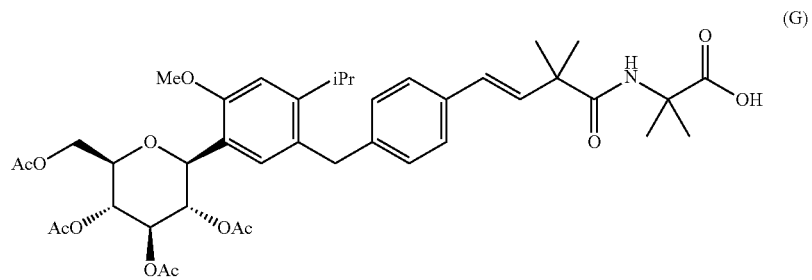

The same procedure as shown in Reference Example 5 was repeated to give intermediate (G) (854 mg, 60%) as a light-yellow amorphous substance, except that intermediate (A) was replaced by intermediate (C).

$^1$H NMR (300 MHz, CHLOROFORM-d) δ ppm 1.08 (d, J=6.84 Hz, 3H) 1.12 (d, J=6.84 Hz, 3H) 1.38 (s, 6H) 1.53 (s, 6H) 1.77 (s, 3H) 2.00 (s, 3H) 2.05 (s, 6H) 3.06 (sept, J=6.84 Hz, 1H) 3.78-3.83 (m, 1H) 3.84 (s, 3H) 3.97 (s, 2H) 4.07-4.18 (m, 1H) 4.17-4.27 (m, 1H) 4.87 (dd, J=6.76, 2.88 Hz, 1H) 5.16-5.25 (m, 1H) 5.27-5.40 (m, 2H) 6.18-6.33 (m, 2H) 6.54 (d, J=16.48 Hz, 1H) 6.77 (s, 1H) 7.03 (d, J=8.08 Hz, 2H) 7.10 (s, 1H) 7.29 (d, J=8.08 Hz, 2H).

MS ESI/APCI Dual posi: 768[M+H]$^+$, 790[M+Na]$^+$.
MS ESI/APCI Dual nega: 766[M−H]$^−$.

Reference Example 8

Preparation of Intermediate (H)

[Chem. 35]

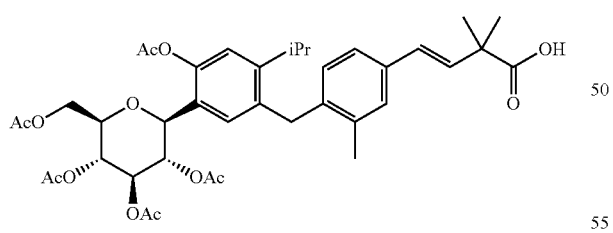

Under an argon atmosphere, a suspension of intermediate (A) (216 g, 0.312 mol), 2,2-dimethyl-3-butenoic acid (53.4 g, 0.467 mol), palladium(II) acetate (3.50 g, 15.6 mmol), tri-O-tolylphosphine (9.48 g, 31.2 mmol) and triethylamine (86.9 mL, 0.623 mol) in acetonitrile (623 mL) was heated under reflux for 3 hours. The reaction mixture was cooled to room temperature, diluted with chloroform (300 mL) and methanol (100 mL), and then filtered through celite. The filtrate was concentrated under reduced pressure and the resulting residue was dissolved in ethyl acetate (1.32 L). This solution was washed with 1 M aqueous hydrochloric acid (0.96 L) and 10% aqueous sodium chloride (1.2 L), and then dried over anhydrous magnesium sulfate. After filtering off the desiccant, the filtrate was further diluted with ethyl acetate (1.2 L), followed by addition of isopropylamine (28.2 mL, 0.327 mol). The mixture was stirred for 1 hour on ice bath. The resulting precipitate was filtered to give an isopropylamine salt of intermediate (H). This salt was dissolved in ethyl acetate (1.2 L) and 1 M aqueous hydrochloric acid (500 mL), and stirred for 30 minutes. The organic layer was separated and washed with 10% aqueous sodium chloride (500 mL), and then dried over anhydrous magnesium sulfate. After filtering off the desiccant, the solvent was distilled off under reduced pressure to give intermediate (H) (207 g, 88%) as a colorless amorphous substance.

$^1$H NMR (300 MHz, CHLOROFORM-d) δ ppm 1.13 (d, J=6.80 Hz, 3H) 1.14 (d, J=6.80 Hz, 3H) 1.43 (s, 6H) 1.76 (s, 3H) 1.99 (s, 3H) 2.03 (s, 3H) 2.05 (s, 3H) 2.28 (s, 3H) 2.37 (s, 3H) 2.98 (sept, J=6.80 Hz, 1H) 3.70-3.80 (m, 1H) 3.91 (s, 2H) 4.05 (dd, J=12.43, 2.18 Hz, 1H) 4.28 (dd, J=12.43, 4.35 Hz, 1H) 4.43-4.50 (m, 1H) 5.11-5.20 (m, 1H) 5.22-5.33 (m, 2H) 6.33-6.49 (m, 2H) 6.68 (d, J=7.93 Hz, 1H) 6.96 (s, 1H) 6.99 (s, 1H) 7.06-7.14 (m, 1H) 7.23 (d, J=1.40 Hz, 1H).

MS ESI/APCI Dual posi: 747[M+Na]$^+$.

Reference Example 9

Preparation of Intermediate (I)

[Chem. 36]

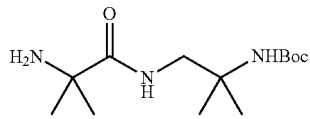

2-Aminoisobutyric acid (150 g, 1.45 mol) was dissolved in water (2.2 L), and sodium carbonate (465 g, 4.39 mol) was added thereto. The reaction mixture was cooled on ice, to which a solution of benzyl chloroformate (227 mL, 1.60 mol) in 1,4-dioxane (0.63 L) was then added dropwise over 45 minutes such that the internal temperature did not exceed 10°

C. After stirring overnight at room temperature, water (3.5 L) and toluene (1.0 L) were added to the reaction mixture. The aqueous layer was separated, to which concentrated hydrochloric acid (700 mL) was then added dropwise until the pH reached 1. Ethyl acetate (1.0 L) was added and stirred for 1 hour. The organic layer was separated and dried over anhydrous magnesium sulfate. After filtering off the desiccant, the solvent was distilled off under reduced pressure.

The resulting residue (338 g) was dissolved in chloroform (1.7 L). To this solution, N,N'-carbonyldiimidazole (CDI) (253 g, 1.56 mol) was added portionwise under ice cooling such that the internal temperature did not exceed 20° C. After stirring at room temperature for 30 minutes, the reaction mixture was cooled again on ice and 1,2-diamino-2-methylpropane (138 g, 1.56 mol) was added dropwise thereto over 25 minutes. After stirring overnight at room temperature, 10% aqueous potassium carbonate (1.7 L) was added. The organic layer was separated and dried over anhydrous magnesium sulfate. After filtering off the desiccant, the solvent was distilled off under reduced pressure.

The resulting residue (417 g) was dissolved in THF (2.0 L). To this solution, Boc$_2$O (355 g, 1.63 mol) was added and stirred at room temperature for 1.5 hours. Then, saturated aqueous sodium bicarbonate (1.0 L) was added to the reaction mixture, and the organic layer was separated and dried over anhydrous magnesium sulfate. After filtering off the desiccant, the solvent was distilled off under reduced pressure.

The resulting residue (549 g) was dissolved in methanol (2.75 L). To this solution, 10% palladium hydroxide (27.5 g) was added and stirred under a hydrogen atmosphere at room temperature for 4.5 hours. After the reaction mixture was filtered through celite, the solvent was distilled off under reduced pressure and the resulting residue was crystallized from a 2:1 heptane:ethyl acetate mixture (1.75 L). The resulting precipitate was filtered to give intermediate (I) (193 g, 53%; 4 steps) as a colorless powder.

$^1$H NMR (300 MHz, CHLOROFORM-d) δ ppm 1.27 (s, 6H) 1.37 (s, 6H) 1.43 (s, 9H) 1.53 (br. s, 2H) 3.39 (d, J=6.53 Hz, 2H) 4.78 (br. s, 1H) 8.04 (br. s, 1H).

MS ESI/APCI Dual posi: 274[M+H]$^+$, 296[M+Na]$^+$.

MS ESI/APCI Dual nega: 308[M+Cl]$^-$.

Example 1-1

[Chem. 37]

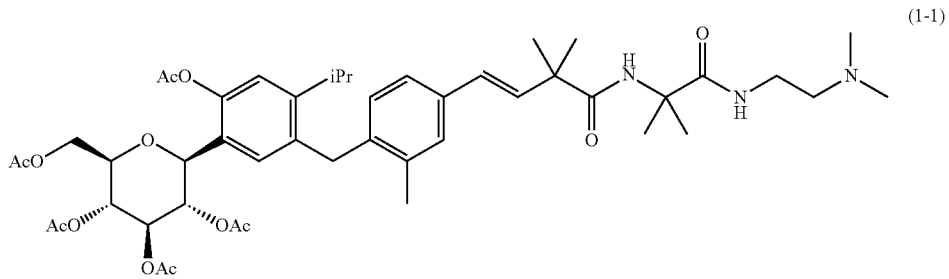

(1-1)

To a solution of intermediate (E) (200 mg, 0.25 mmol), 1-hydroxybenzotriazole monohydrate (HOBt.H$_2$O) (57 mg, 0.37 mmol) and N,N-dimethylethylenediamine (65 mg, 0.74 mmol) in N,N-dimethylformamide (3.0 mL), N-ethyl-N'-3-dimethylaminopropylcarbodiimide hydrochloride (EDC.HCl) (71 mg, 0.37 mmol) was added and stirred at room temperature for 8 hours. The reaction mixture was poured into water (50 mL) and extracted with ethyl acetate (50 mL) The organic layer was washed with brine (20 mL) and dried over anhydrous magnesium sulfate. After filtering off the desiccant, the solvent was distilled off under reduced pressure. The resulting residue was purified by silica gel column chromatography (chloroform→chloroform:methanol=9:1) to give compound (1-1) (132 mg, 61%) as a colorless amorphous substance.

$^1$H NMR (300 MHz, CHLOROFORM-d) δ ppm 1.13, 1.15 (each d, J=6.92 Hz, each 3H) 1.38 (s, 6H) 1.53 (s, 6H) 1.77 (s, 3H) 1.99 (s, 3H) 2.03 (s, 3H) 2.05 (s, 3H) 2.23 (s, 6H) 2.31 (s, 3H) 2.37 (s, 3H) 2.41 (t, J=5.67 Hz, 2H) 2.90-3.03 (m, 1H) 3.25-3.34 (m, 2H) 3.71-3.80 (m, 1H) 3.92 (s, 2H) 4.05 (dd, J=12.59, 2.18 Hz, 1H) 4.23-4.32 (m, 1H) 4.44-4.52 (m, 1H) 5.11-5.20 (m, 1H) 5.22-5.33 (m, 2H) 6.33 (d, J=16.63 Hz, 1H) 6.41 (br. s., 1H) 6.51 (d, J=16.63 Hz, 1H) 6.68 (d, J=7.77 Hz, 1H) 6.77 (br. s., 1H) 7.00 (s, 2H) 7.12 (d, J=7.77 Hz, 1H) 7.26 (s, 1H).

MS ESI/APCI Dual posi: 880[M+H]$^+$, 902[M+Na]$^+$.

MS ESI/APCI Dual nega: 914[M+Cl]$^-$.

Example 1-2

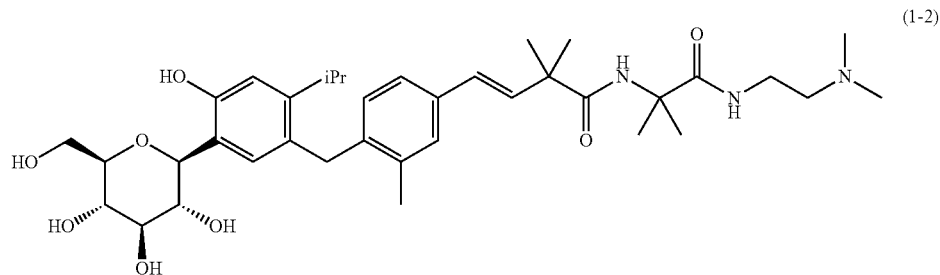

To a solution of compound (1-1) (127 mg, 0.14 mmol) in methanol (2.0 mL), sodium methoxide (4.88 M/MeOH, 10 µL) was added and stirred at room temperature for 1 hour. A small amount of dry ice was added to neutralize the reaction mixture, and the solvent was distilled off under reduced pressure.

The resulting residue was purified by NH-type silica gel column chromatography (chloroform:methanol=9:1→6:4) to give compound (1-2) (77 mg, 80%) as a colorless amorphous substance.

$^1$H NMR (600 MHz, METHANOL-$d_4$) δ ppm 1.10 (d, J=6.92 Hz, 6H) 1.36 (s, 6H) 1.45 (s, 6H) 2.23 (s, 6H) 2.31 (s, 3H) 2.40 (t, J=6.88 Hz, 2H) 2.87-2.96 (m, 1H) 3.28 (t, J=6.88 Hz, 2H) 3.34-3.41 (m, 2H) 3.43-3.50 (m, 1H) 3.51-3.57 (m, 1H) 3.67 (dd, J=12.15, 2.52 Hz, 1H) 3.84 (d, J=11.46 Hz, 1H) 3.89 (s, 2H) 4.47 (d, J=9.63 Hz, 1H) 6.39 (d, J=16.05 Hz, 1H) 6.50 (d, J=16.05 Hz, 1H) 6.75 (d, J=8.25 Hz, 1H) 6.80 (s, 1H) 6.97 (s, 1H) 7.11 (d, J=8.25 Hz, 1H) 7.25 (s, 1H).

MS ESI/APCI Dual posi: 670[M+H]$^+$.
MS ESI/APCI Dual nega: 668[M−H]$^−$, 704[M+Cl]$^−$.
Anal. Calcd for $C_{37}H_{55}N_3O_8 \cdot 1.4H_2O$: C, 63.94; H, 8.38; N, 6.05. Found: C, 64.13; H, 8.39; N, 5.88.

Example 2-1

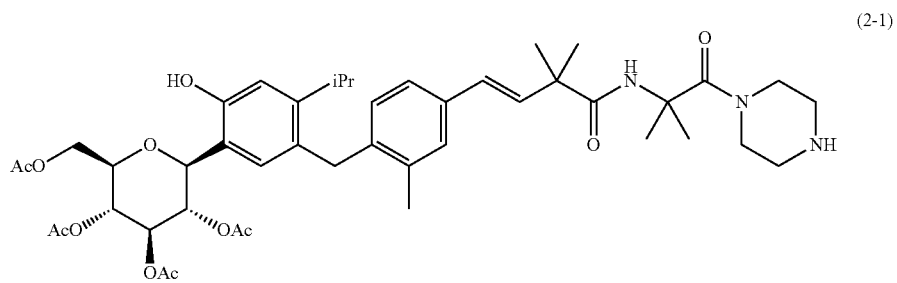

The same procedure as shown in Example 1-1 was repeated to give compound (2-1) (103 mg, 47%) as a colorless amorphous substance, except that N,N-dimethylethylenediamine was replaced by piperazine.

$^1$H NMR (300 MHz, CHLOROFORM-d) δ ppm 1.14, 1.16 (each d, J=6.99 Hz, each 3H) 1.38 (s, 6H) 1.61 (s, 6H) 1.71 (s, 3H) 1.99 (s, 3H) 2.05 (s, 3H) 2.12 (s, 3H) 2.27 (s, 3H) 2.79-2.87 (m, 4H) 2.87-2.99 (m, 1H) 3.56-3.66 (m, 4H) 3.75-3.94 (m, 3H) 4.12-4.20 (m, 1H) 4.25-4.34 (m, 1H) 4.44-4.52 (m, 1H) 5.23-5.32 (m, 3H) 6.30 (d, J=16.32 Hz, 1H) 6.48 (d, J=16.32 Hz, 1H) 6.53 (s, 1H) 6.68 (d, J=7.77 Hz, 1H) 6.88 (s, 1H) 6.97 (s, 1H) 7.05-7.12 (m, 1H) 7.22 (s, 1H).

MS ESI/APCI Dual posi: 836[M+H]$^+$, 858[M+Na]$^+$.
MS ESI/APCI Dual nega: 834[M−H]$^−$, 870[M+Cl]$^−$.

Example 2-2

[Chem. 40]

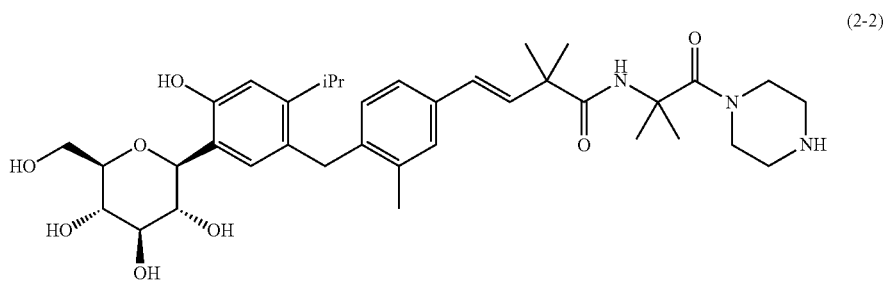

(2-2)

The same procedure as shown in Example 1-2 was repeated to give compound (2-2) (52 mg, 66%) as a colorless amorphous substance, except that compound (1-1) was replaced by compound (2-1).

$^1$H NMR (600 MHz, METHANOL-$d_4$) δ ppm 1.10 (d, J=6.42 Hz, 6H) 1.36 (s, 6H) 1.44 (s, 6H) 2.31 (s, 3H) 2.70 (br. s, 4H) 2.90-2.95 (m, 1H) 3.36-3.39 (m, 2H) 3.43-3.61 (m, 7H) 3.65-3.69 (m, 1H) 3.84 (d, J=11.92 Hz, 1H) 3.88 (s, 2H) 4.46 (d, J=9.63 Hz, 1H) 6.38 (d, J=16.05 Hz, 1H) 6.47 (d, J=16.05 Hz, 1H) 6.76 (d, J=7.79 Hz, 1H) 6.80 (s, 1H) 6.95 (s, 1H) 7.10 (d, J=7.79 Hz, 1H) 7.22 (s, 1H).

MS ESI/APCI Dual posi: 668[M+H]$^+$, 690[M+Na]$^+$.
MS ESI/APCI Dual nega: 666[M−H]$^-$, 702[M+Cl]$^-$.

Example 3-1

[Chem. 41]

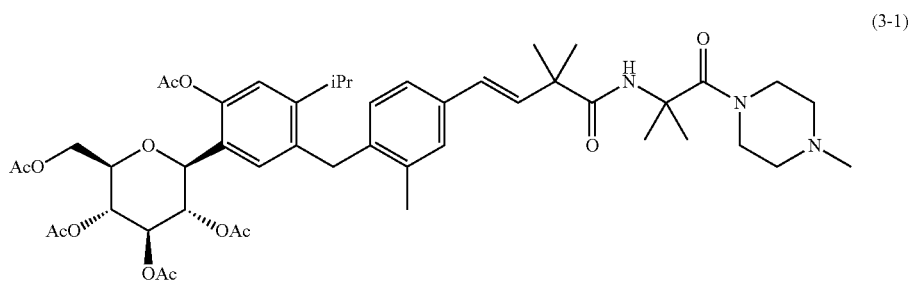

(3-1)

The same procedure as shown in Example 1-1 was repeated to give compound (3-1) (135 mg, 61%) as a colorless amorphous substance, except that N,N-dimethylethylenediamine was replaced by 1-methylpiperazine.

$^1$H NMR (300 MHz, CHLOROFORM-d) δ ppm 1.13, 1.15 (each d, J=6.84 Hz, each 3H) 1.37 (s, 6H) 1.60 (s, 6H) 1.77 (s, 3H) 1.99 (s, 3H) 2.03 (s, 3H) 2.05 (s, 3H) 2.27 (s, 3H) 2.30 (s, 3H) 2.33-2.41 (m, 7H) 2.88-3.04 (m, 1H) 3.60-3.70 (m, 4H) 3.72-3.80 (m, 1H) 3.92 (s, 2H) 4.05 (dd, J=12.59, 2.33 Hz, 1H) 4.27 (dd, J=12.59, 4.51 Hz, 1H) 4.43-4.54 (m, 1H) 5.10-5.20 (m, 1H) 5.22-5.32 (m, 2H) 6.31 (d, J=16.48 Hz, 1H) 6.49 (d, J=16.48 Hz, 1H) 6.68 (d, J=8.08 Hz, 1H) 6.86 (s, 1H) 7.00 (s, 2H) 7.08-7.14 (m, 1H) 7.24 (s, 1H).

MS ESI/APCI Dual posi: 892[M+H]$^+$, 914[M+Na]$^+$.
MS ESI/APCI Dual nega: 926[M+Cl]$^-$.

Example 3-2

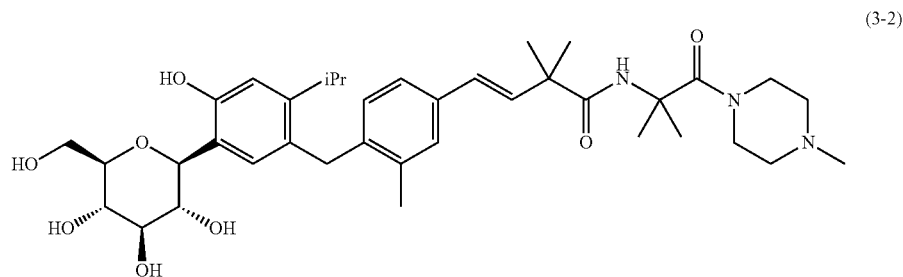

(3-2)

The same procedure as shown in Example 1-2 was repeated to give compound (3-2) (79 mg, 79%) as a colorless amorphous substance, except that compound (1-1) was replaced by compound (3-1).

$^1$H NMR (600 MHz, METHANOL-$d_4$) δ ppm 1.10 (d, J=6.88 Hz, 6H) 1.37 (s, 6H) 1.44 (s, 6H) 2.16 (s, 3H) 2.22-2.38 (m, 7H) 2.87-2.96 (m, 1H) 3.35-3.41 (m, 2H) 3.42-3.51 (m, 2H) 3.51-3.56 (m, 1H) 3.56-3.71 (m, 5H) 3.84 (d, J=12.38 Hz, 1H) 3.88 (s, 2H) 4.47 (d, J=9.63 Hz, 1H) 6.38 (d, J=16.51 Hz, 1H) 6.46 (d, J=16.51 Hz, 1H) 6.75 (d, J=8.25 Hz, 1H) 6.80 (s, 1H) 6.97 (s, 1H) 7.09 (d, J=8.25 Hz, 1H) 7.22 (s, 1H).

MS ESI/APCI Dual posi: 682[M+H]$^+$, 704[M+Na]$^+$.
MS ESI/APCI Dual nega: 680[M−H]$^−$, 716[M+Cl]$^−$.

Example 4-1

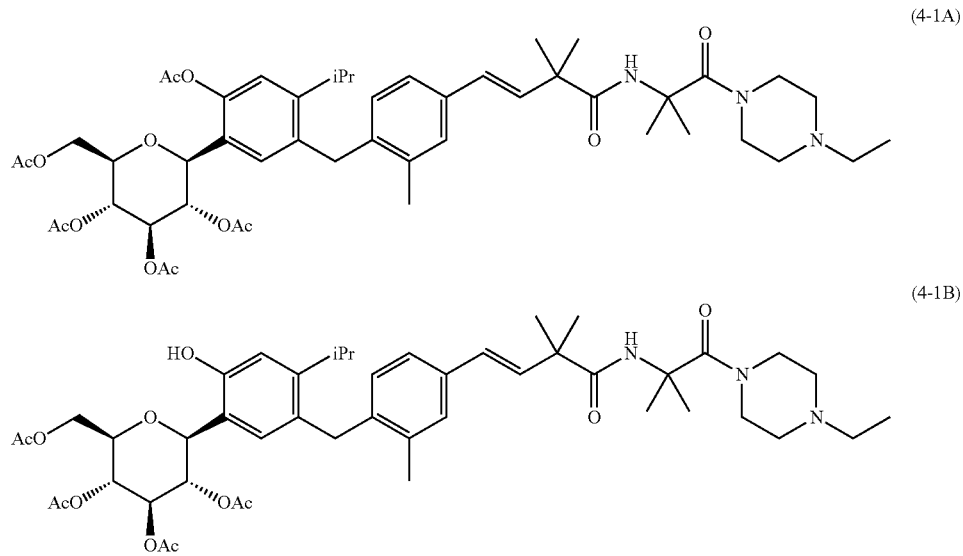

(4-1A)

(4-1B)

The same procedure as shown in Example 1-1 was repeated to give compound (4-1A) (87.9 mg, 38%) as a colorless gum and compound (4-1B) (42.9 mg, 19%) as a colorless gum, except that N,N-dimethylethylenediamine was replaced by 1-ethylpiperazine.

Compound (4-1A)

$^1$H NMR (300 MHz, CHLOROFORM-d) δ ppm 1.07 (t, J=7.23 Hz, 3H) 1.12-1.16 (m, 6H) 1.37 (s, 6H) 1.61 (s, 6H) 1.77 (s, 3H) 1.99 (s, 3H) 2.03 (s, 3H) 2.05 (s, 3H) 2.30 (s, 3H) 2.34-2.44 (m, 9H) 2.90-3.05 (m, 1H) 3.60-3.72 (m, 4H) 3.72-3.80 (m, 1H) 3.92 (s, 2H) 4.05 (dd, J=12.36, 1.94 Hz, 1H) 4.27 (dd, J=12.36, 4.43 Hz, 1H) 4.48 (d, J=9.79 Hz, 1H) 5.15 (t, J=9.79 Hz, 1H) 5.22-5.31 (m, 2H) 6.31 (d, J=16.2 Hz, 1H) 6.49 (d, J=16.2 Hz, 1H) 6.68 (d, J=8.08 Hz, 1H) 6.86-6.93 (m, 1H) 7.00 (s, 2H) 7.11 (d, J=8.08 Hz, 1H) 7.24 (s, 1H).

MS ESI/APCI Dual posi: 907[M+H]$^+$, 929[M+Na]$^+$.
MS ESI/APCI Dual nega: 941[M+Cl]$^−$.

Compound (4-1B)

$^1$H NMR (300 MHz, CHLOROFORM-d) δ ppm 1.03-1.19 (m, 9H) 1.37 (s, 6H) 1.62 (s, 6H) 1.71 (s, 3H) 1.99 (s, 3H) 2.05 (s, 3H) 2.12 (s, 3H) 2.27 (s, 3H) 2.33-2.46 (m, 6H) 2.93 (sept, J=6.76 Hz, 1H) 3.58-3.71 (m, 4H) 3.73-3.91 (m, 3H) 4.12-4.21 (m, 1H) 4.24-4.34 (m, 1H) 4.48 (d, J=9.17 Hz, 1H) 5.21-5.34 (m, 3H) 6.30 (d, J=16.1 Hz, 1H) 6.48 (d, J=16.1 Hz, 1H) 6.53 (s, 1H) 6.68 (d, J=7.93 Hz, 1H) 6.88 (s, 1H) 6.99 (s, 1H) 7.08 (d, J=7.93 Hz, 1H) 7.22 (s, 1H).

MS ESI/APCI Dual posi: 865[M+H]$^+$, 887[M+Na]$^+$.
MS ESI/APCI Dual nega: 899[M+Cl]$^-$.

Example 4-2

[Chem. 44]

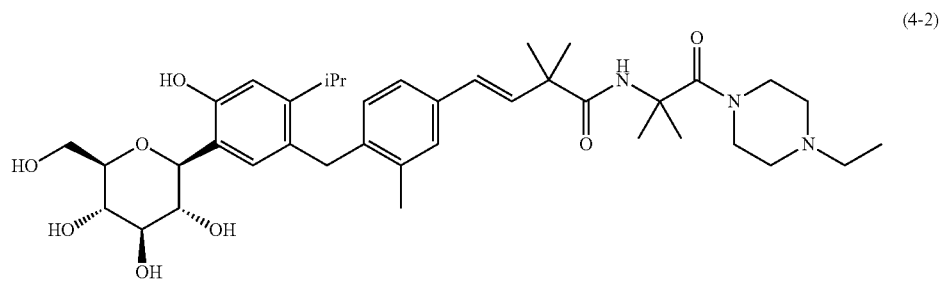

(4-2)

To compound (4-1A) (87.9 mg, 0.0973 mmol) and compound (4-1B) (42.9 mg, 0.0486 mmol), triethylamine/water/methanol (1/1/5, 5 mL) was added. The reaction mixture was stirred overnight at room temperature, and the solvent was distilled off under reduced pressure. The resulting residue was purified by silica gel column chromatography (chloroform→chloroform:methanol=8:2) to give compound (4-2) (79.2 mg, 78%) as a colorless amorphous substance.

$^1$H NMR (600 MHz, METHANOL-d$_4$) δ ppm 0.98 (t, J=7.23 Hz, 3H) 1.10 (d, J=6.88 Hz, 6H) 1.36 (s, 6H) 1.44 (s, 6H) 2.23-2.42 (m, 9H) 2.85-2.99 (m, 1H) 3.35-3.41 (m, 2H) 3.42-3.48 (m, 1H) 3.50-3.56 (m, 1H) 3.55-3.71 (m, 5H) 3.81-3.90 (m, 3H) 4.47 (d, J=9.63 Hz, 1H) 6.39 (d, J=16.1 Hz, 1H) 6.46 (d, J=16.1 Hz, 1H) 6.71-6.77 (m, 1H) 6.80 (s, 1H) 6.98 (s, 1H) 7.09 (d, J=7.79 Hz, 1H) 7.22 (s, 1H).

MS ESI/APCI Dual posi: 696[M+H]$^+$, 718[M+Na]$^+$.
MS ESI/APCI Dual nega: 694[M−H]$^-$.

Anal. Calcd for $C_{39}H_{57}N_3O_8 \cdot 1.2H_2O$: C, 65.3; H, 8.34; N, 5.86. Found: C, 65.3; H, 8.36; N, 5.68.

Example 5-1

[Chem. 45]

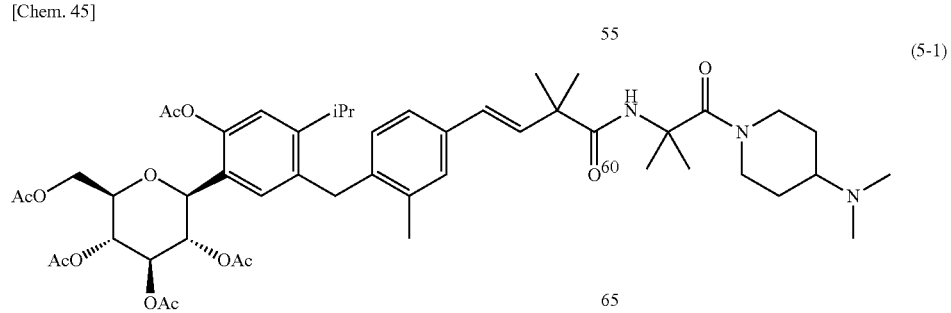 [SMILES: COc1cc(C(C)C)c(Cc2ccc(/C=C/C(C)(C)C(=O)NC(C)(C)C(=O)NCCN(C)C)cc2C)cc1[C@@H]1O[C@H](COC(C)=O)[C@@H](OC(C)=O)[C@H](OC(C)=O)[C@H]1OC(C)=O]

(5-1)

To a solution of intermediate (E) (205 mg, 0.253 mmol), HOBt.H₂O (68 mg, 0.506 mmol) and 4-dimethylaminopiperidine (65 mg, 0.506 mmol) in N,N-dimethylformamide (2.0 mL), EDC.HCl (97 mg, 0.506 mmol) was added and stirred at 70° C. for 2 hours. The reaction mixture was poured into water (50 mL) and extracted with ethyl acetate (50 mL). The organic layer was washed with brine (20 mL) and dried over anhydrous magnesium sulfate. After filtering off the desiccant, the solvent was distilled off under reduced pressure. The resulting residue was purified by silica gel column chromatography (chloroform→chloroform:methanol=3:1) to give compound (5-1) (80 mg, 34%) as a colorless amorphous substance.

¹H NMR (300 MHz, CHLOROFORM-d) δ ppm 1.13 (d, J=6.76 Hz, 3H) 1.15 (d, J=6.76 Hz, 3H) 1.30-1.49 (m, 2H) 1.38 (s, 6H) 1.61 (s, 6H) 1.77 (s, 3H) 1.84 (d, J=12.75 Hz, 2H) 1.99 (s, 3H) 2.03 (s, 3H) 2.05 (s, 3H) 2.27 (s, 6H) 2.30 (s, 3H) 2.37 (s, 3H) 2.81 (t, J=12.28 Hz, 2H) 2.97 (sept, J=6.76 Hz, 1H) 3.76 (ddd, J=10.03, 4.66, 2.25 Hz, 1H) 3.92 (s, 2H) 4.05 (dd, J=12.43, 2.25 Hz, 1H) 4.28 (dd, J=12.43, 4.66 Hz, 1H) 4.33-4.53 (m, 3H) 5.10-5.34 (m, 3H) 6.31 (d, J=15.00 Hz, 1H) 6.50 (d, J=15.00 Hz, 1H) 6.68 (d, J=8.08 Hz, 1H) 6.97-7.04 (m, 2H) 7.11 (d, J=8.08 Hz, 1H) 7.25 (s, 1H).

MS ESI/APCI Dual posi: 920[M+H]⁺.

MS ESI/APCI Dual nega: 954[M+Cl]⁻.

Example 5-2

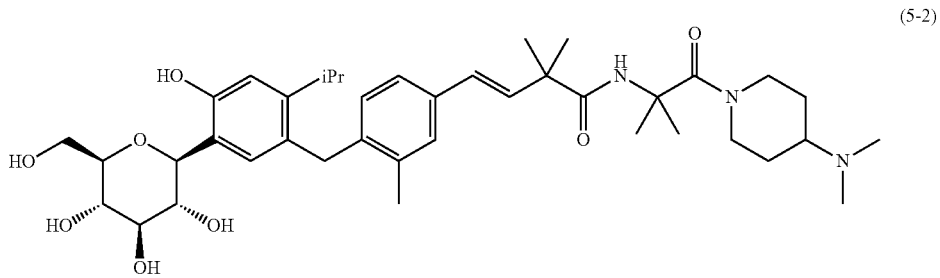

(5-2)

The same procedure as shown in Example 1-2 was repeated to give compound (5-2) (33 mg, 53%) as a colorless amorphous substance, except that compound (1-1) was replaced by compound (5-1).

¹H NMR (600 MHz, METHANOL-d₄) δ ppm 1.08 (d, J=6.42 Hz, 6H) 1.21-1.32 (m, 2H) 1.35 (s, 6H) 1.43 (s, 6H) 1.73 (br. s., 2H) 2.16 (s, 6H) 2.28 (s, 3H) 2.28-2.37 (m, 1H) 2.89 (sept, J=6.42 Hz, 1H) 3.31-3.33 (m, 2H) 3.44 (t, J=8.71 Hz, 1H) 3.48-3.56 (m, 1H) 3.66 (dd, J=11.92, 2.75 Hz, 1H) 3.83 (d, J=11.92 Hz, 1H) 3.86 (s, 2H) 4.45 (d, J=9.63 Hz, 1H) 6.35-6.41 (m, 1H) 6.43-6.47 (m, 1H) 6.72 (d, J=7.79 Hz, 1H) 6.78 (s, 1H) 6.96 (s, 1H) 7.08 (d, J=7.79 Hz, 1H) 7.21 (s, 1H).

MS ESI/APCI Dual posi: 710[M+H]⁺.

MS ESI/APCI Dual nega: 708[M−H]⁻.

Anal. Calcd for C₄₀H₅₉N₃O₈·1.5H₂O: C, 65.19; H, 8.50; N, 5.70. Found: C, 64.81; H, 8.46; N, 5.61.

Example 6-1

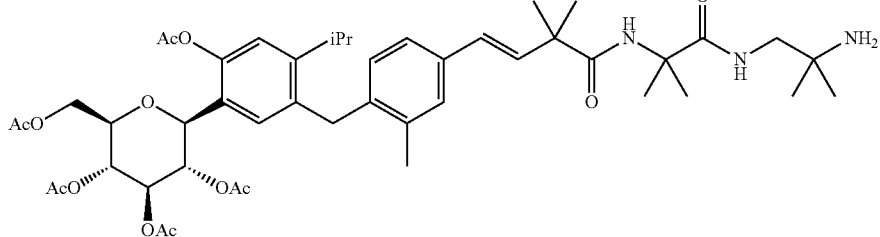

(6-1)

To a solution of intermediate (E) (680 mg, 0.746 mmol) in chloroform (5.0 mL), CDI (182 mg, 1.12 mmol) was added and stirred at room temperature for 1 hour. Then, 1,2-diamino-2-methylpropane (79 mg, 0.895 mmol) was added and stirred at room temperature for 18 hours. The reaction mixture was diluted with saturated aqueous sodium bicarbonate and extracted twice with chloroform. The combined organic layers were dried over anhydrous sodium sulfate. After filtering off the desiccant, the solvent was distilled off under reduced pressure. The resulting residue was purified by silica gel column chromatography (chloroform→chloroform:methanol=85:15) to give compound (6-1) (140 mg, 21%) as a colorless amorphous substance.

$^1$H NMR (300 MHz, CHLOROFORM-d) δ ppm 1.11-1.17 (m, 6H) 1.11 (s, 6H) 1.39 (s, 6H) 1.53 (s, 6H) 1.77 (s, 3H) 1.99 (s, 3H) 2.03 (s, 3H) 2.05 (s, 3H) 2.31 (s, 3H) 2.37 (s, 3H) 2.89-3.05 (m, 1H) 3.14 (d, J=5.91 Hz, 2H) 3.76 (ddd, J=9.71, 4.51, 2.10 Hz, 1H) 3.93 (s, 2H) 4.05 (dd, J=12.51, 2.10 Hz, 1H) 4.27 (dd, J=12.51, 4.51 Hz, 1H) 4.49 (d, J=7.46 Hz, 1H) 5.11-5.20 (m, 1H) 5.23-5.31 (m, 2H) 6.26 (s, 1H) 6.29-6.38 (m, 1H) 6.48-6.57 (m, 1H) 6.69 (d, J=7.93 Hz, 1H) 6.97-7.03 (m, 3H) 7.12 (d, J=7.93 Hz, 1H) 7.25 (s, 1H).

MS ESI/APCI Dual posi: 880[M+H]$^+$.

Example 6-2

[Chem. 48]

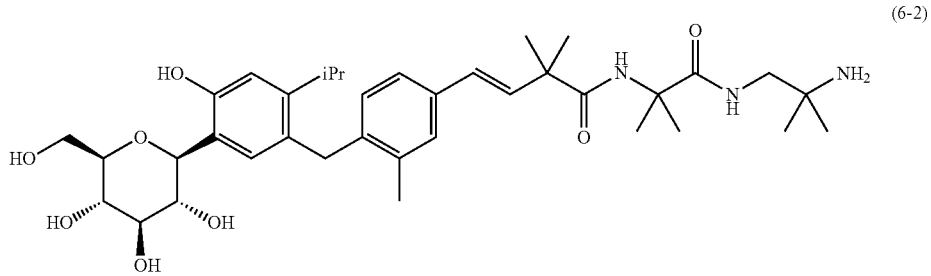

(6-2)

The same procedure as shown in Example 1-2 was repeated to give compound (6-2) (104 mg, 98%) as a colorless amorphous substance, except that compound (1-1) was replaced by compound (6-1).

$^1$H NMR (600 MHz, METHANOL-d$_4$) δ ppm 1.02 (s, 6H) 1.05-1.10 (m, 6H) 1.35 (s, 6H) 1.44 (s, 6H) 2.29 (s, 3H) 2.85-2.93 (m, 1H) 3.09 (s, 2H) 3.34-3.39 (m, 2H) 3.42-3.47 (m, 1H) 3.52 (t, J=9.40 Hz, 1H) 3.63-3.69 (m, 1H) 3.80-3.85 (m, 1H) 3.86 (s, 2H) 4.46 (d, J=9.63 Hz, 1H) 6.35-6.41 (m, 1H) 6.44-6.51 (m, 1H) 6.73 (d, J=7.79 Hz, 1H) 6.78 (s, 1H) 6.96 (s, 1H) 7.06-7.10 (m, 1H) 7.23 (s, 1H).

MS ESI/APCI Dual posi: 670[M+H]$^+$, 692[M+Na]$^+$.
MS ESI/APCI Dual nega: 668[M−H]$^−$, 704[M+Cl]$^−$.

Alternatively, compound (6-2) can also be synthesized as described in Examples 6-3 and 6-4 below.

Example 6-3

[Chem. 49]

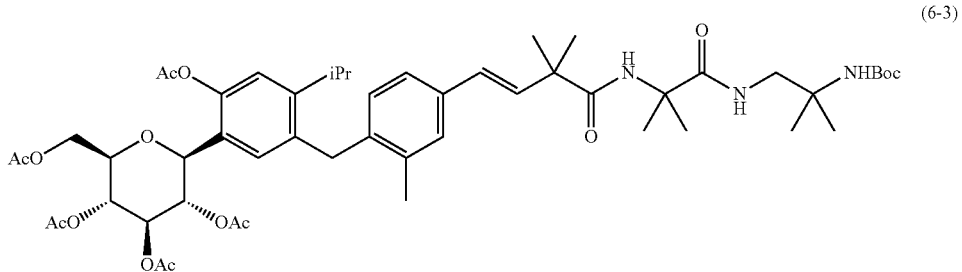

(6-3)

To a solution of intermediate (H) (205 g, 0.273 mol), intermediate (I) (97.0 g, 0.355 mol), HOBt.H$_2$O (62.7 g, 0.410 mol) and triethylamine (114 mL, 0.819 mol) in N,N-dimethylformamide (1.98 L), EDC.HCl (78.5 g, 0.410 mol) was added and stirred at room temperature for 11 hours. To the reaction mixture, toluene (1.0 L) and 10% aqueous sodium chloride (2.0 L) were added, and the organic layer was separated. The aqueous layer was extracted with toluene (1.0 L), and the combined organic layers were washed with 5% aqueous sodium chloride (1.0 L) and dried over anhydrous magnesium sulfate. After filtering off the desiccant, the solvent was distilled off under reduced pressure. The resulting residue was dissolved in 2-propanol (300 mL) at 50° C., and heptane (2.7 L) was added dropwise thereto. The mixture was stirred for 1 hour under ice cooling, and the resulting precipitate was filtered to give compound (6-3) (221 g, 83%) as a colorless powder.

$^1$H NMR (300 MHz, CHLOROFORM-d) δ ppm 1.13 (d, J=6.88 Hz, 3H) 1.14 (d, J=6.88 Hz, 3H) 1.26 (s, 6H) 1.39 (s, 6H) 1.44 (s, 9H) 1.55 (s, 6H) 1.77 (s, 3H) 1.99 (s, 3H) 2.03 (s, 3H) 2.05 (s, 3H) 2.30 (s, 3H) 2.37 (s, 3H) 2.97 (sept, J=6.88 Hz, 1H) 3.41 (d, J=5.60 Hz, 2H) 3.72-3.80 (m, 1H) 3.92 (s, 2H) 4.05 (dd, J=12.43, 2.02 Hz, 1H) 4.28 (dd, J=12.43, 4.51 Hz, 1H) 4.45-4.52 (m, 1H) 4.65 (s, 1H) 5.11-5.19 (m, 1H) 5.22-5.33 (m, 2H) 6.29-6.39 (m, 1H) 6.46-6.57 (m, 2H) 6.69 (d, J=8.00 Hz, 1H) 6.96-7.03 (m, 2H) 7.11 (dd, J=8.00, 1.63 Hz, 1H) 7.24-7.26 (m, 1H) 7.59 (br. s, 1H).

Example 6-4

To a solution of compound (6-3) (220 g, 0.225 mol) in chloroform (3.0 L), trifluoroacetic acid (297 mL, 3.88 mol) was added dropwise at room temperature over 10 minutes and stirred at the same temperature for 20 hours. The reaction mixture was diluted with toluene (3.0 L) and concentrated. The concentrated product was dissolved in ethyl acetate (3.0 L) and washed with 10% aqueous sodium carbonate (1.2 L) and brine (1.0 L), followed by distilling off the solvent under reduced pressure.

The resulting residue (240 g) was dissolved in methanol (1.5 L) and cooled on ice, followed by addition of triethylamine (0.3 L) and water (0.3 L). After stirring at room temperature for 13 hours, additional methanol (1.5 L), triethylamine (0.3 L) and water (0.3 L) were further added and stirred at room temperature for 20 hours. The reaction mixture was concentrated and co-evaporated with methanol. The resulting residue was purified by NH-type silica gel column chromatography (ethyl acetate:ethanol:water=15:2:1→10:2:1) to give compound (6-2) (129 g, 86%; 2 steps) as a colorless amorphous substance.

Example 7-1

[Chem. 50]

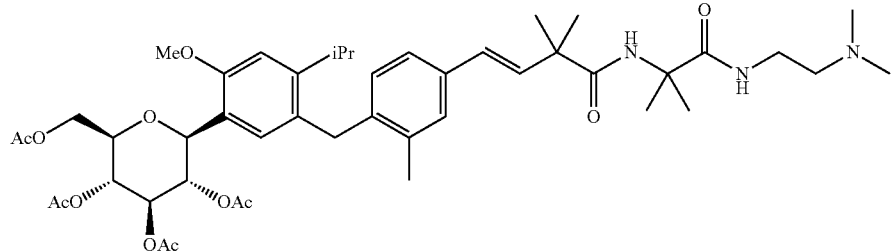

(7-1)

The same procedure as shown in Example 1-1 was repeated to give compound (7-1) (112 mg, 74%) as a colorless amorphous substance, except that intermediate (E) was replaced by intermediate (F).

$^1$H NMR (300 MHz, CHLOROFORM-d) δ ppm 1.12, 1.14 (each d, J=6.84 Hz, each 3H) 1.37 (s, 6H) 1.51 (s, 6H) 1.76 (s, 3H) 1.99 (s, 3H) 2.04 (s, 3H) 2.04 (s, 3H) 2.23 (s, 6H) 2.32 (s, 3H) 2.41 (t, J=6.22 Hz, 2H) 2.86-2.99 (m, 1H) 3.25-3.33 (m, 2H) 3.76-3.90 (m, 6H) 4.07-4.15 (m, 1H) 4.18-4.26 (m, 1H) 4.76-4.85 (m, 1H) 5.13-5.22 (m, 1H) 5.26-5.36 (m, 2H) 6.31 (d, J=16.48 Hz, 1H) 6.37 (s, 1H) 6.50 (d, J=16.48 Hz, 1H) 6.61-6.67 (m, 1H) 6.81 (s, 1H) 6.99 (s, 1H) 7.06-7.12 (m, 1H) 7.24 (s, 1H).

MS ESI/APCI Dual posi: 852[M+H]$^+$.
MS ESI/APCI Dual nega: 886[M+Cl]$^-$.

Example 7-2

[Chem. 51]

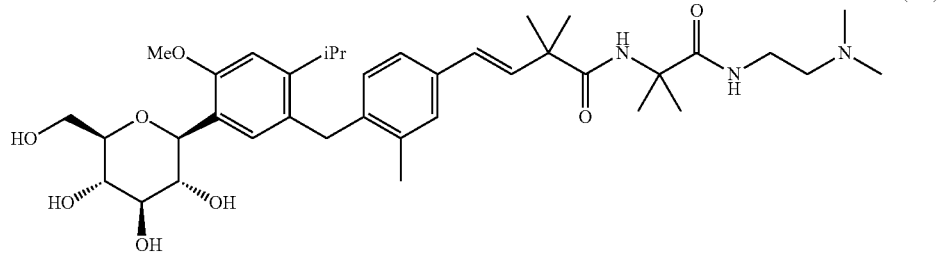

(7-2)

The same procedure as shown in Example 1-2 was repeated to give compound (7-2) (69 mg, 78%) as a colorless amorphous substance, except that compound (1-1) was replaced by compound (7-1).

$^1$H NMR (600 MHz, METHANOL-$d_4$) δ ppm 1.13, 1.15 (each d, J=6.84 Hz, each 3H) 1.36 (s, 6H) 1.45 (s, 6H) 2.21 (s, 6H) 2.32 (s, 3H) 2.39 (t, J=6.88 Hz, 2H) 2.93-3.02 (m, 1H) 3.24-3.39 (m, 4H) 3.42-3.48 (m, 1H) 3.49-3.54 (m, 1H) 3.58-3.65 (m, 1H) 3.80-3.87 (m, 4H) 3.91 (s, 2H) 4.61 (d, J=9.63 Hz, 1H) 6.39 (d, J=16.51 Hz, 1H) 6.50 (d, J=16.51 Hz, 1H) 6.73 (d, J=7.80 Hz, 1H) 6.92 (s, 1H) 7.08 (s, 1H) 7.10 (d, J=7.80 Hz, 1H) 7.25 (s, 1H).

MS ESI/APCI Dual posi: 684[M+H]$^+$.

MS ESI/APCI Dual nega: 682[M−H]$^−$, 718[M+Cl]$^−$.

Anal. Calcd for $C_{38}H_{57}N_3O_8 \cdot 1.7H_2O$: C, 63.88; H, 8.52; N, 5.88. Found: C, 63.84; H, 8.41; N, 5.75.

Example 8-1

[Chem. 52]

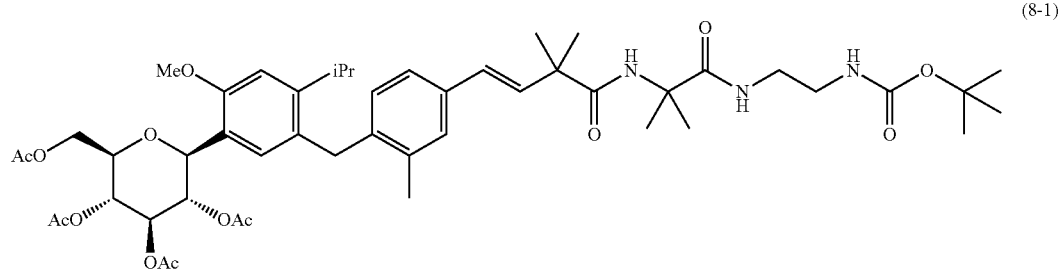

(8-1)

The same procedure as shown in Example 1-1 was repeated to give compound (8-1) (145 mg, 89%) as a colorless amorphous substance, except that intermediate (E) was replaced by intermediate (F), and N,N-dimethylethylenediamine was replaced by N-t-butoxycarbonylethylenediamine.

MS ESI/APCI Dual posi: 924[M+H]$^+$, 946[M+Na]$^+$.

MS ESI/APCI Dual nega: 958[M+Cl]$^−$.

Example 8-2

[Chem. 53]

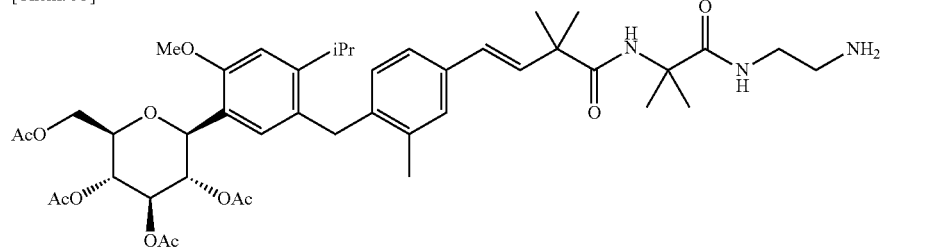

(8-2)

To a solution of compound (8-1) in chloroform (3.0 ml), trifluoroacetic acid (600 μL) was added and stirred at room temperature for 3 hours. The reaction mixture was concentrated under reduced pressure and then purified by silica gel column chromatography (chloroform:methanol=95:5→60:40) to give compound (8-2) (68 mg, 55%) as a colorless amorphous substance.

$^1$H NMR (300 MHz, CHLOROFORM-d) δ ppm 1.14, 1.16 (each d, J=6.37 Hz, each 3H) 1.32 (s, 6H) 1.42 (s, 6H) 1.77 (s, 3H) 1.98 (s, 3H) 2.03 (s, 3H) 2.04 (s, 3H) 2.32 (s, 3H) 2.90-3.02 (m, 1H) 3.22-3.34 (m, 2H) 3.48-3.57 (m, 2H) 3.76-

3.96 (m, 6H) 4.07-4.14 (m, 1H) 4.17-4.25 (m, 1H) 4.79-4.87 (m, 1H) 5.12-5.22 (m, 1H) 5.24-5.36 (m, 2H) 6.32 (s, 1H) 6.40 (d, J=16.63 Hz, 1H) 6.51 (d, J=16.63 Hz, 1H) 6.65 (d, J=8.55 Hz, 1H) 6.82 (s, 1H) 6.96 (s, 1H) 7.07-7.13 (m, 1H) 7.28-7.31 (m, 1H) 8.04 (br. s., 2H).

MS ESI/APCI Dual posi: 824[M+H]$^+$, 846[M+Na]$^+$.

MS ESI/APCI Dual nega: 858[M+Cl]$^-$.

Example 8-3

[Chem. 54]

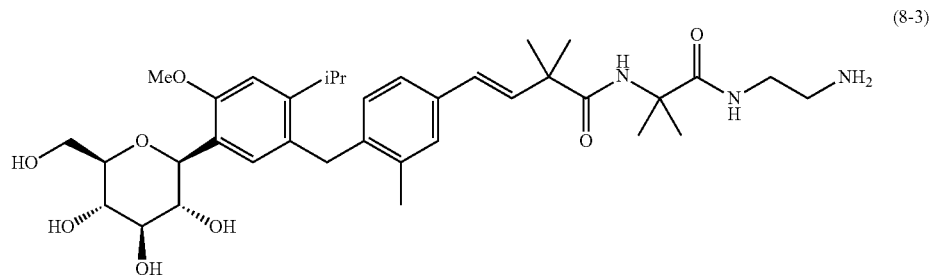

(8-3)

The same procedure as shown in Example 1-2 was repeated to give compound (8-3) (22 mg, 44%) as a colorless amorphous substance, except that compound (1-1) was replaced by compound (8-2).

$^1$H NMR (600 MHz, METHANOL-d$_4$) δ ppm 1.13, 1.15 (each d, J=6.84 Hz, each 3H) 1.36 (s, 6H) 1.45 (s, 6H) 2.32 (s, 3H) 2.63-2.71 (m, 2H) 2.94-3.03 (m, 1H) 3.23 (t, J=5.96 Hz, 2H) 3.28-3.39 (m, 4H) 3.43-3.48 (m, 1H) 3.48-3.54 (m, 1H) 3.62 (dd, J=12.15, 5.73 Hz, 1H) 3.79-3.88 (m, 2H) 3.92 (s, 2H) 4.61 (d, J=9.63 Hz, 1H) 6.40 (d, J=16.51 Hz, 1H) 6.50 (d, J=16.51 Hz, 1H) 6.74 (d, J=7.79 Hz, 1H) 6.92 (s, 1H) 7.07 (s, 1H) 7.11 (d, J=7.79 Hz, 1H) 7.26 (s, 1H).

MS ESI/APCI Dual posi: 656[M+H]$^+$.

MS ESI/APCI Dual nega: 654[M–H]$^-$, 690[M+Cl]$^-$.

Example 9-1

[Chem. 55]

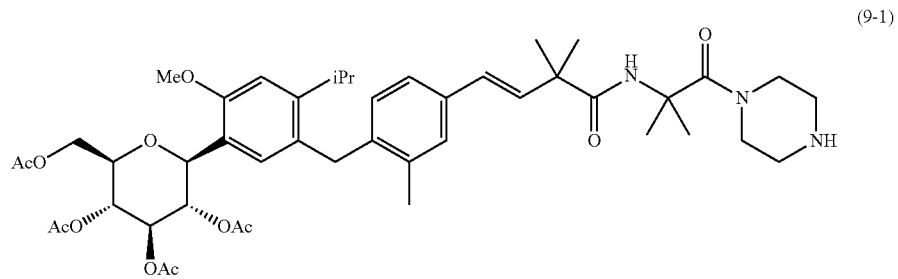

(9-1)

The same procedure as shown in Example 1-1 was repeated to give compound (9-1) (42 mg, 38%) as a colorless amorphous substance, except that intermediate (E) was replaced by intermediate (F), and N,N-dimethylethylenediamine was replaced by piperazine.

$^1$H NMR (300 MHz, CHLOROFORM-d) δ ppm 1.12, 1.14 (each d, J=6.99 Hz, each 3H) 1.37 (s, 6H) 1.58 (s, 6H) 1.76 (s, 3H) 1.99 (s, 3H) 2.04 (s, 3H) 2.04 (s, 3H) 2.32 (s, 3H)

2.79-2.86 (m, 4H) 2.88-2.99 (m, 1H) 3.57-3.64 (m, 4H) 3.76-3.95 (m, 6H) 4.07-4.14 (m, 1H) 4.18-4.26 (m, 1H) 4.77-4.84 (m, 1H) 5.13-5.22 (m, 1H) 5.26-5.37 (m, 2H) 6.29 (d, J=16.16 Hz, 1H) 6.49 (d, J=16.16 Hz, 1H) 6.64 (d, J=7.93 Hz, 1H) 6.77-6.83 (m, 2H) 6.99 (s, 1H) 7.05-7.11 (m, 1H) 7.22 (br. s., 1H).

MS ESI/APCI Dual posi: 850[M+H]$^+$, 872[M+Na]$^+$.
MS ESI/APCI Dual nega: 884[M+Cl]$^-$.

Example 9-2

[Chem. 56]

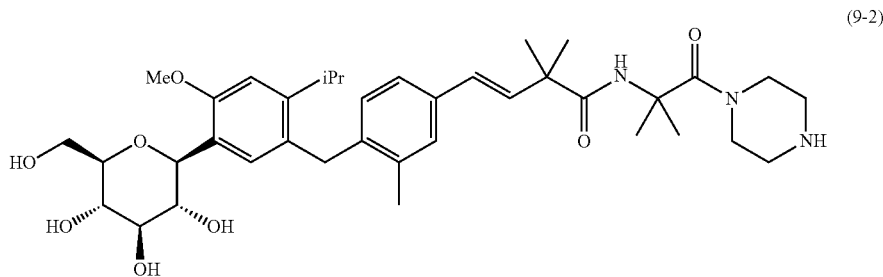

(9-2)

The same procedure as shown in Example 1-2 was repeated to give compound (9-2) (27 mg, 94%) as a colorless amorphous substance, except that compound (1-1) was replaced by compound (9-1).

$^1$H NMR (600 MHz, METHANOL-d$_4$) δ ppm 1.14, 1.16 (each d, J=6.42 Hz, each 3H) 1.36 (s, 6H) 1.44 (s, 6H) 2.32 (s, 3H) 2.69 (br. s., 4H) 2.95-3.03 (m, 1H) 3.28-3.38 (m, 2H) 3.42-3.52 (m, 2H) 3.53-3.65 (m, 5H) 3.80-3.84 (m, 1H) 3.84 (s, 3H) 3.92 (s, 2H) 4.61 (d, J=9.17 Hz, 1H) 6.39 (d, J=16.05 Hz, 1H) 6.47 (d, J=16.05 Hz, 1H) 6.74 (d, J=7.79 Hz, 1H) 6.92 (s, 1H) 7.06 (s, 1H) 7.10 (d, J=7.79 Hz, 1H) 7.22 (s, 1H).

MS ESI/APCI Dual posi: 682[M+H]$^+$.
MS ESI/APCI Dual nega: 680[M−H]$^-$, 716[M+Cl]$^-$.

Example 10-1

[Chem. 57]

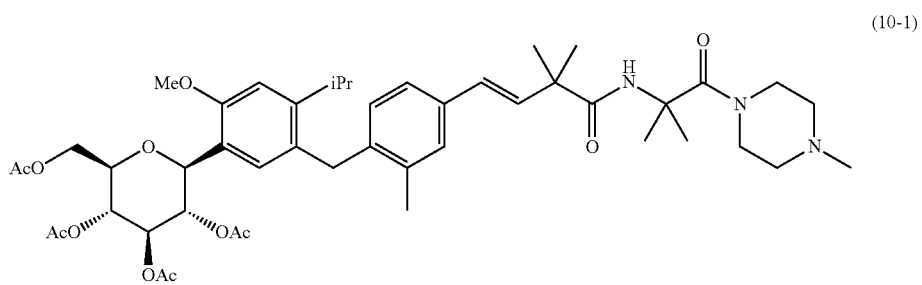

(10-1)

The same procedure as shown in Example 1-1 was repeated to give a crude product of compound (10-1) (100 mg) as a colorless amorphous substance, except that intermediate (E) was replaced by intermediate (F), and N,N-dimethylethylenediamine was replaced by N-methylpiperazine. This product was used for the next reaction without further purification.

$^1$H NMR (300 MHz, CHLOROFORM-d) δ ppm 1.12 (d, J=8.5 Hz, 3H) 1.15 (d, J=8.5 Hz, 3H) 1.36 (s, 6H) 1.56 (s, 6H) 1.77 (s, 3H) 1.99 (s, 3H) 2.04 (s, 6H) 2.30 (s, 3H) 2.32 (s, 3H) 2.38-2.50 (m, 4H) 2.85-3.02 (m, 1H) 3.61-3.74 (m, 4H) 3.76-3.84 (m, 1H) 3.81-3.96 (m, 1H) 3.86 (s, 3H) 4.07-4.15 (m, 1H) 4.18-4.27 (m, 1H) 4.75-4.88 (m, 1H) 5.11-5.24 (m, 1H) 5.26-5.37 (m, 2H) 6.22-6.38 (m, 1H) 6.43-6.54 (m, 1H) 6.59-6.70 (m, 2H) 6.81 (s, 1H) 6.96-7.02 (m, 1H) 7.04-7.12 (m, 1H) 7.20-7.26 (m, 1H).

Example 10-2

[Chem. 58]

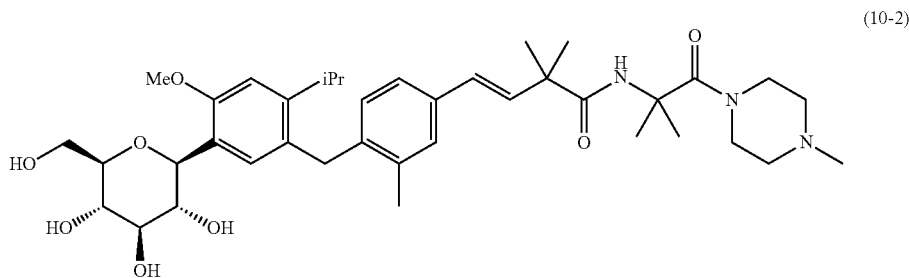

(10-2)

The same procedure as shown in Example 1-2 was repeated to give compound (10-2) (8.0 mg, 9%; 2 steps) as a colorless amorphous substance, except that compound (1-1) was replaced by compound (10-1).

$^1$H NMR (600 MHz, METHANOL-d$_4$) δ ppm 1.09-1.16 (m, 6H) 1.35 (s, 6H) 1.42 (s, 6H) 2.12-2.16 (m, 3H) 2.23-2.33 (br. s., 4H) 2.30 (s, 3H) 2.92-3.01 (m, 1H) 3.28 (s, 2H) 3.30-3.38 (m, 1H) 3.41-3.51 (m, 2H) 3.55-3.66 (m, 5H) 3.78-3.86 (m, 4H) 3.90 (s, 2H) 4.59 (d, J=9.17 Hz, 1H) 6.33-6.39 (m, 1H) 6.42-6.47 (m, 1H) 6.72 (d, J=7.79 Hz, 1H) 6.90 (s, 1H) 7.04-7.11 (m, 2H) 7.19-7.24 (m, 1H).

MS ESI/APCI Dual posi: 696[M+H]$^+$, 718[M+Na]$^+$.
MS ESI/APCI Dual nega: 694[M−H]$^−$, 730[M+Cl]$^−$.

Example 11-1

[Chem. 59]

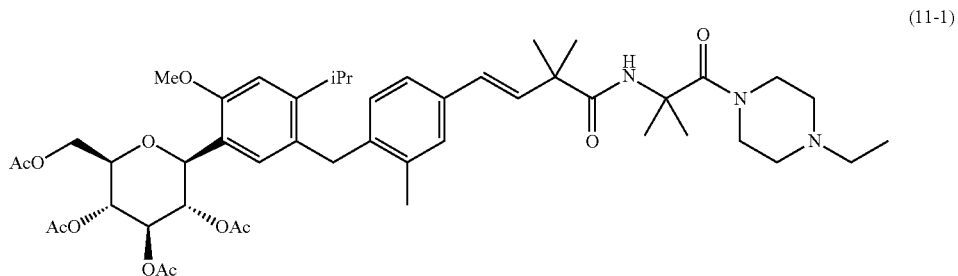

(11-1)

The same procedure as shown in Example 1-1 was repeated to give compound (11-1) (200 mg, 89%) as a light-yellow amorphous substance, except that intermediate (E) was replaced by intermediate (F), and N,N-dimethylethylenediamine was replaced by 1-ethylpiperazine.

$^1$H NMR (300 MHz, CHLOROFORM-d) δ ppm 1.07 (t, J=7.23 Hz, 3H) 1.11 (d, J=6.84 Hz, 3H) 1.14 (d, J=6.84 Hz, 3H) 1.36 (s, 6H) 1.59 (s, 6H) 1.76 (s, 3H) 1.99 (s, 3H) 2.04 (s, 3H) 2.04 (s, 3H) 2.32 (s, 3H) 2.36-2.44 (m, 6H) 2.93 (sept, J=6.84 Hz, 1H) 3.61-3.71 (m, 4H) 3.77-3.84 (m, 1H) 3.83-3.94 (m, 5H) 4.05-4.16 (m, 1H) 4.18-4.27 (m, 1H) 4.76-4.86 (m, 1H) 5.14-5.23 (m, 1H) 5.25-5.37 (m, 2H) 6.29 (d, J=16.1 Hz, 1H) 6.48 (d, J=16.1 Hz, 1H) 6.64 (d, J=7.62 Hz, 1H) 6.77-6.86 (m, 2H) 6.99 (s, 1H) 7.08 (d, J=7.62 Hz, 1H) 7.22 (s, 1H).

MS ESI/APCI Dual posi: 879[M+H]$^+$, 901[M+Na]$^+$.
MS ESI/APCI Dual nega: 913[M+Cl]$^-$.

Example 11-2

[Chem. 60]

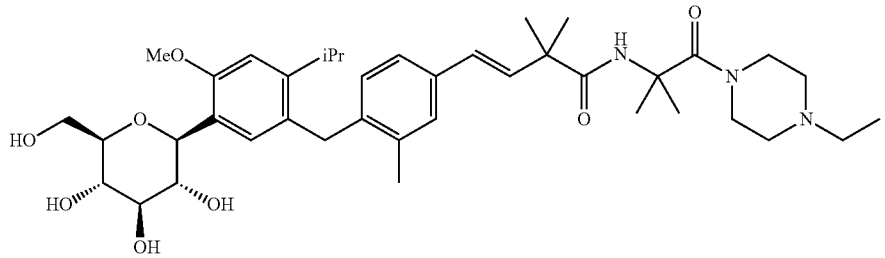

(11-2)

The same procedure as shown in Example 4-2 was repeated to give compound (11-2) (118 mg, 73%) as a colorless amorphous substance, except that compounds (4-1A) and (4-1B) were replaced by compound (11-1).

$^1$H NMR (600 MHz, METHANOL-d$_4$) δ ppm 0.97 (t, J=7.11 Hz, 3H) 1.10-1.19 (m, 6H) 1.37 (s, 6H) 1.45 (s, 6H) 2.26-2.42 (m, 9H) 2.97 (sept, J=6.76 Hz, 1H) 3.32-3.40 (m, 2H) 3.43-3.48 (m, 1H) 3.48-3.55 (m, 1H) 3.55-3.72 (m, 5H) 3.79-3.89 (m, 4H) 3.91 (s, 2H) 4.61 (d, J=9.17 Hz, 1H) 6.39 (d, J=16.5 Hz, 1H) 6.46 (d, J=16.5 Hz, 1H) 6.73 (d, J=7.79 Hz, 1H) 6.92 (s, 1H) 7.04-7.14 (m, 2H) 7.23 (s, 1H).

MS ESI/APCI Dual posi: 710[M+H]$^+$, 732[M+Na]$^+$.
MS ESI/APCI Dual nega: 744[M+Cl]$^-$.

Anal. Calcd for C$_{40}$H$_{59}$N$_3$O$_8$·1.5H$_2$O: C, 65.2; H, 8.48; N, 5.70. Found: C, 65.1; H, 8.38; N, 5.64.

Example 12-1

[Chem. 61]

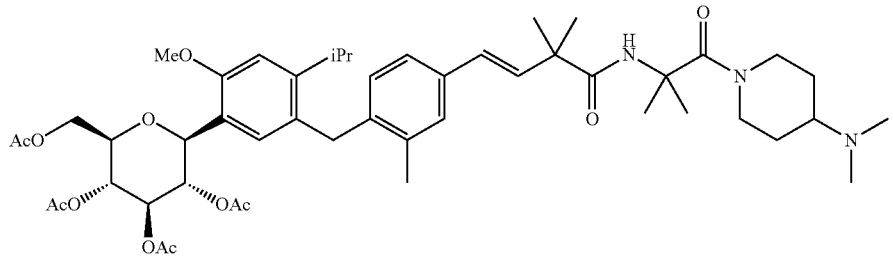

(12-1)

The same procedure as shown in Example 5-1 was repeated to give compound (12-1) (55 mg, 40%) as a colorless amorphous substance, except that intermediate (E) was replaced by intermediate (F).

$^1$H NMR (300 MHz, CHLOROFORM-d) δ ppm 1.12, 1.14 (each d, J=6.92 Hz, each 3H) 1.28-1.47 (m, 8H) 1.60 (s, 6H) 1.73-1.89 (m, 5H) 1.99 (s, 3H) 2.04 (s, 3H) 2.04 (s, 3H) 2.22-2.35 (m, 10H) 2.73-2.99 (m, 3H) 3.76-3.84 (m, 1H) 3.84-3.90 (m, 5H) 4.07-4.15 (m, 1H) 4.18-4.26 (m, 1H) 4.34-4.50 (m, 2H) 4.75-4.86 (m, 1H) 5.13-5.23 (m, 1H) 5.26-5.39 (m, 2H) 6.30 (d, J=16.48 Hz, 1H) 6.48 (d, J=16.48 Hz, 1H) 6.63 (d, J=8.39 Hz, 1H) 6.81 (s, 1H) 6.94-7.01 (m, 2H) 7.04-7.11 (m, 1H) 7.23 (s, 1H).

MS ESI/APCI Dual posi: 892[M+H]$^+$, 914[M+Na]$^+$.

Example 12-2

[Chem. 62]

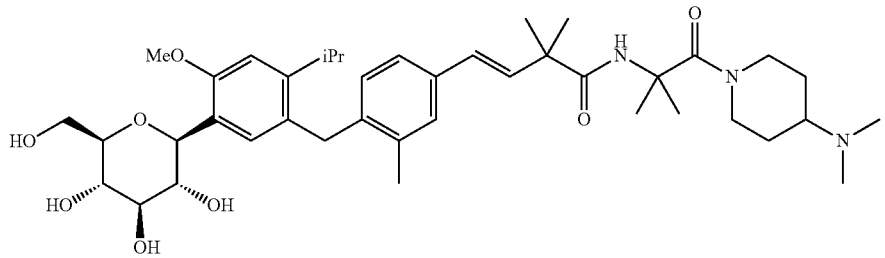

(12-2)

The same procedure as shown in Example 1-2 was repeated to give compound (12-2) (55 mg, 82%) as a colorless amorphous substance, except that compound (1-1) was replaced by compound (12-1).

$^1$H NMR (600 MHz, METHANOL-d$_4$) δ ppm 1.13, 1.15 (each d, J=6.84 Hz, each 3H) 1.24-1.33 (m, 2H) 1.37 (s, 6H) 1.44 (s, 6H) 1.75 (br. s, 2H) 2.17 (s, 6H) 2.30-2.39 (m, 4H) 2.93-3.01 (m, 1H) 3.28-3.38 (m, 5H) 3.43-3.47 (m, 1H) 3.47-3.53 (m, 1H) 3.62 (dd, J=12.15, 5.73 Hz, 1H) 3.80-3.86 (m, 3H) 3.91 (s, 2H) 4.48 (br. s., 2H) 4.61 (d, J=9.63 Hz, 1H) 6.40 (d, J=16.05 Hz, 1H) 6.47 (d, J=16.05 Hz, 1H) 6.73 (d, J=7.79 Hz, 1H) 6.92 (s, 1H) 7.06-7.11 (m, 2H) 7.23 (s, 1H).

MS ESI/APCI Dual posi: 724[M+H]$^+$, 746[M+Na]$^+$.
MS ESI/APCI Dual nega: 722[M−H]$^-$, 758[M+Cl]$^-$.

Anal. Calcd for $C_{41}H_{61}N_3O_8 \cdot 2.5H_2O$: C, 64.04; H, 8.65; N, 5.46. Found: C, 64.01; H, 8.38; N, 5.49.

Example 13-1

[Chem. 63]

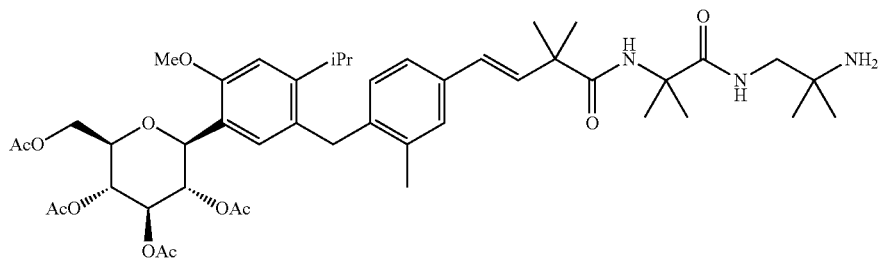

(13-1)

he same procedure as shown in Example 6-1 was repeated to give compound (13-1) (1.98 g, 99%) as a colorless amorphous substance, except that intermediate (E) was replaced by intermediate (F).

¹H NMR (300 MHz, CHLOROFORM-d) δ ppm 1.10 (s, 6H) 1.12 (d, J=6.84 Hz, 3H) 1.14 (d, J=6.84 Hz, 3H) 1.36 (s, 6H) 1.56 (s, 6H) 1.77 (s, 3H) 1.99 (s, 3H) 2.04 (s, 6H) 2.30 (s, 3H) 2.85-3.02 (m, 1H) 3.13 (d, J=5.91 Hz, 2H) 3.76-3.84 (m, 1H) 3.81-3.96 (m, 1H) 3.86 (s, 3H) 4.07-4.15 (m, 1H) 4.18-4.27 (m, 1H) 4.75-4.88 (m, 1H) 5.11-5.24 (m, 1H) 5.26-5.37 (m, 2H) 6.22-6.38 (m, 1H) 6.43-6.54 (m, 1H) 6.59-6.70 (m, 1H) 6.81 (s, 1H) 6.96-7.02 (m, 2H) 7.04-7.12 (m, 1H) 7.20-7.26 (m, 1H).

Example 13-2

[Chem. 64]

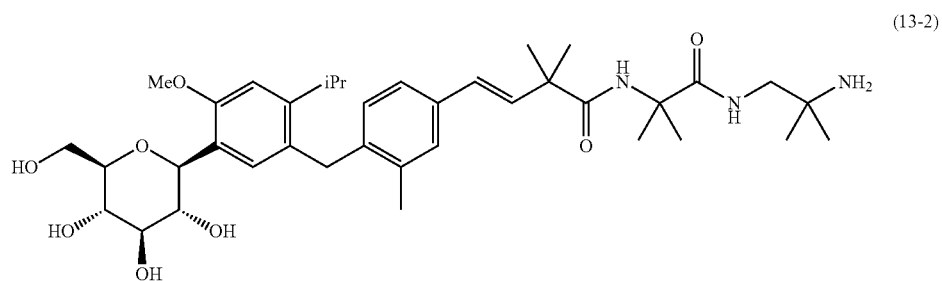

(13-2)

The same procedure as shown in Example 1-2 was repeated to give compound (13-2) (1.0 g, 65%) as a colorless amorphous substance, except that compound (1-1) was replaced by compound (13-1).
¹H NMR (600 MHz, METHANOL-d₄) δ ppm 1.01 (s, 6H) 1.09-1.15 (m, 6H) 1.35 (s, 6H) 1.43 (s, 6H) 2.31 (s, 3H) 2.91-3.00 (m, 1H) 3.08 (s, 2H) 3.27-3.36 (m, 5H) 3.41-3.46 (m, 1H) 3.47-3.52 (m, 1H) 3.60 (dd, J=11.92, 5.96 Hz, 1H) 3.80-3.84 (m, 4H) 3.90 (s, 2H) 4.59 (d, J=9.63 Hz, 1H) 6.36-6.41 (m, 1H) 6.45-6.50 (m, 1H) 6.71 (d, J=7.79 Hz, 1H) 6.90 (s, 1H) 7.06 (s, 1H) 7.07-7.10 (m, 1H) 7.20-7.25 (m, 1H).
MS ESI/APCI Dual posi: 684[M+H]⁺.
MS ESI/APCI Dual nega: 682[M−H]⁻, 718[M+Cl]⁻.

Example 14-1

[Chem. 65]

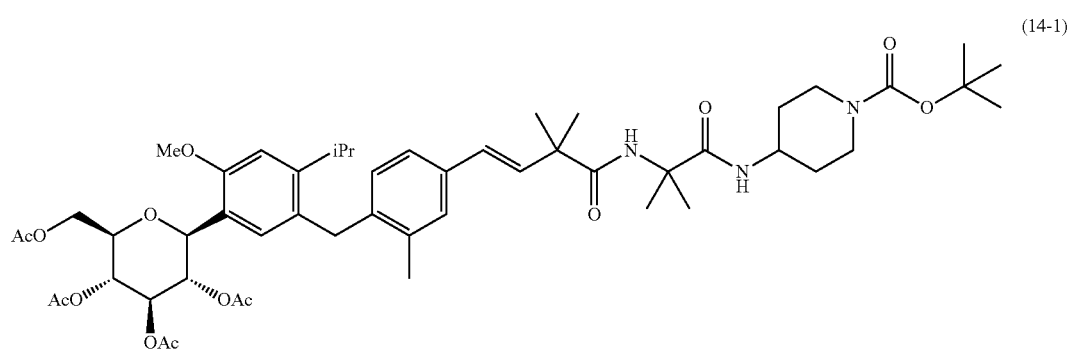

(14-1)

The same procedure as shown in Example 1-1 was repeated to give compound (14-1) (200 mg, quant.) as a light-yellow oil, except that intermediate (E) was replaced by intermediate (F), and N,N-dimethylethylenediamine was replaced by 4-amino-1-t-butoxycarbonylpiperidine.

$^1$H NMR (300 MHz, CHLOROFORM-d) δ ppm 1.11 (d, J=6.99 Hz, 3H) 1.14 (d, J=6.99 Hz, 3H) 1.25-1.33 (m, 2H) 1.36 (s, 6H) 1.45 (s, 9H) 1.48 (s, 6H) 1.77 (s, 3H) 1.79-1.93 (m, 2H) 1.99 (s, 3H) 2.04 (s, 3H) 2.04 (s, 3H) 2.32 (s, 3H) 2.90-2.98 (m, 3H) 3.75-4.00 (m, 9H) 4.07-4.15 (m, 1H) 4.18-4.27 (m, 1H) 4.79-4.86 (m, 1H) 5.19 (d, J=10.10 Hz, 1H) 5.26-5.35 (m, 2H) 6.09 (s, 1H) 6.26 (d, J=16.48 Hz, 1H) 6.50 (d, J=16.48 Hz, 1H) 6.65 (d, J=8.32 Hz, 1H) 6.74-6.83 (m, 2H) 6.99 (s, 1H) 7.08 (dd, J=8.32, 2.72 Hz, 1H) 7.22 (d, J=2.72 Hz, 1H).

MS ESI/APCI Dual posi: 965[M+H]$^+$, 987[M+Na]$^+$.
MS ESI/APCI Dual nega: 999[M+Cl]$^-$.

Example 14-2

[Chem. 66]

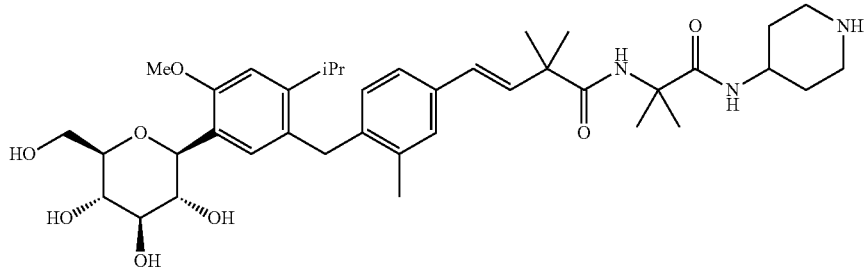

(14-2)

To a solution of compound (14-1) (185 mg, 0.192 mmol) in chloroform (2 mL), trifluoroacetic acid (450 μL) was added. The reaction mixture was stirred at room temperature for 2 hours, and the solvent was distilled off under reduced pressure. To the resulting residue, triethylamine/water/methanol (1/1/5, 4 mL) was added, and the reaction mixture was stirred overnight at room temperature. The solvent was distilled off under reduced pressure and the resulting residue was purified by silica gel column chromatography (chloroform→chloroform:methanol=8:2) to give compound (14-2) (103 mg, 77%) as a colorless amorphous substance.

$^1$H NMR (600 MHz, METHANOL-d$_4$) δ ppm 1.14 (d, J=5.50 Hz, 3H) 1.15 (d, J=5.50 Hz, 3H) 1.27-1.35 (m, 2H) 1.37 (s, 6H) 1.45 (s, 6H) 1.78 (d, J=11.46 Hz, 2H) 2.33 (s, 3H) 2.56-2.68 (m, 2H) 2.95-3.03 (m, 3H) 3.33-3.37 (m, 2H) 3.43-3.48 (m, 1H) 3.49-3.53 (m, 1H) 3.57-3.66 (m, 1H) 3.68-3.75 (m, 1H) 3.81-3.84 (m, 1H) 3.85 (s, 3H) 3.92 (s, 2H) 4.61 (d, J=9.17 Hz, 1H) 6.34-6.43 (m, 1H) 6.45-6.56 (m, 1H) 6.74 (d, J=7.79 Hz, 1H) 6.92 (s, 1H) 7.04-7.16 (m, 2H) 7.26 (s, 1H).

MS ESI/APCI Dual posi: 696[M+H]$^+$, 718[M+Na]$^+$.

Example 15-1

[Chem. 67]

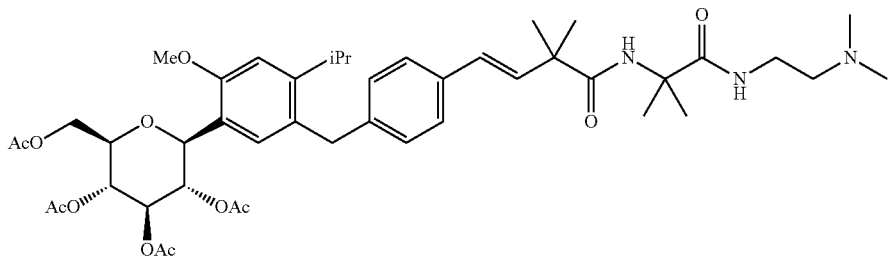

(15-1)

$^1$H NMR (300 MHz, CHLOROFORM-d) δ ppm 1.05 (d, J=6.84 Hz, 3H) 1.10 (d, J=6.84 Hz, 3H) 1.38 (s, 6H) 1.49 (s, 6H) 1.77 (s, 3H) 2.00 (s, 3H) 2.05 (s, 3H) 2.06 (s, 3H) 2.46 (s, 6H) 2.64-2.78 (m, 2H) 3.04 (sept, J=6.84 Hz, 1H) 3.38-3.49 (m, 2H) 3.78-3.83 (m, 1H) 3.85 (s, 3H) 3.87-4.04 (m, 2H) 4.08-4.18 (m, 1H) 4.18-4.30 (m, 1H) 4.87 (d, J=9.48 Hz, 1H) 5.16-5.27 (m, 1H) 5.28-5.44 (m, 2H) 6.35 (s, 1H) 6.40-6.57 (m, 2H) 6.77 (s, 1H) 7.01 (d, J=8.24 Hz, 2H) 7.13 (s, 1H) 7.32 (d, J=8.24 Hz, 2H) 7.40 (s, 1H).

MS ESI/APCI Dual posi: 839[M+H]$^+$.
MS ESI/APCI Dual nega: 873[M+Cl]$^-$.

Example 15-2

[Chem. 68]

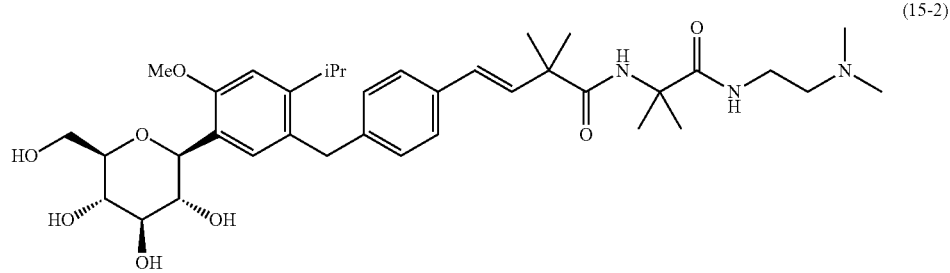

(15-2)

The same procedure as shown in Example 4-2 was repeated to give compound (15-2) (62.1 mg, 75%) as a colorless amorphous substance, except that compounds (4-1A) and (4-1B) were replaced by compound (15-1).

$^1$H NMR (600 MHz, METHANOL-d$_4$) δ ppm 1.07 (d, J=6.76 Hz, 3H) 1.09 (d, J=6.76 Hz, 3H) 1.36 (s, 6H) 1.44 (s, 6H) 2.23 (s, 6H) 2.41 (t, J=6.88 Hz, 2H) 3.10 (sept, J=6.76 Hz, 1H) 3.26-3.30 (m, 2H) 3.35-3.45 (m, 2H) 3.45-3.52 (m, 1H) 3.54-3.60 (m, 1H) 3.62-3.69 (m, 1H) 3.79-3.89 (m, 4H) 3.99 (s, 2H) 4.65 (d, J=9.63 Hz, 1H) 6.39 (d, J=16.51 Hz, 1H) 6.52 (d, J=16.51 Hz, 1H) 6.88 (s, 1H) 7.07 (d, J=8.25 Hz, 2H) 7.23 (s, 1H) 7.31 (d, J=8.25 Hz, 2H).

MS ESI/APCI Dual posi: 670[M+H]$^+$.
MS ESI/APCI Dual nega: 704[M+Cl]$^-$.
Anal. Calcd for C$_{37}$H$_{55}$N$_3$O$_8$·1.0H$_2$O: C, 64.6; H, 8.36; N, 6.11. Found: C, 64.5; H, 8.31; N, 6.02.

Example 16-1

[Chem. 69]

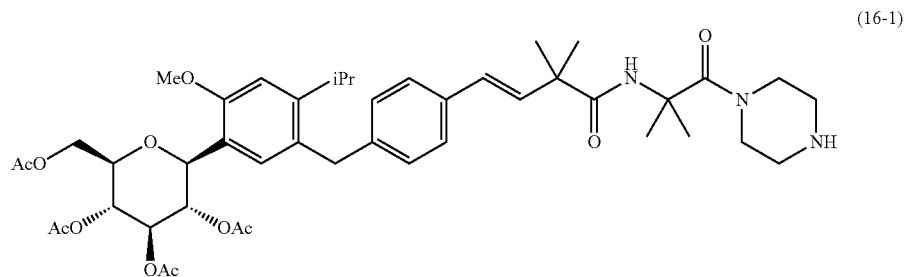

(16-1)

The same procedure as shown in Example 1-1 was repeated to give compound (16-1) (90 mg, 55%) as a colorless amorphous substance, except that intermediate (E) was replaced by intermediate (G), and N,N-dimethylethylenediamine was replaced by piperazine.

$^1$H NMR (300 MHz, CHLOROFORM-d) δ ppm 1.06 (d, J=6.6 Hz, 3H) 1.11 (d, J=6.6 Hz, 3H) 1.35 (s, 6H) 1.77 (s, 6H) 2.00 (s, 3H) 2.04 (s, 3H) 2.06 (s, 3H) 2.25 (br. s., 2H) 2.78-2.88 (m, 4H) 2.96-3.12 (m, 1H) 3.55-3.65 (m, 4H) 3.78-3.88 (m, 1H) 3.85 (s, 3H) 3.88-4.04 (m, 2H) 4.09-4.18 (m, 1H) 4.20-4.30 (m, 1H) 4.88 (d, J=9.48 Hz, 1H) 5.15-5.27 (m, 1H) 5.28-5.44 (m, 2H) 6.22-6.33 (m, 1H) 6.41-6.55 (m, 1H) 6.72-6.85 (m, 2H) 6.96-7.06 (m, 2H) 7.14 (s, 1H) 7.23-7.32 (m, 2H)

MS ESI/APCI Dual posi: 836[M+H]$^+$.

Example 16-2

[Chem. 70]

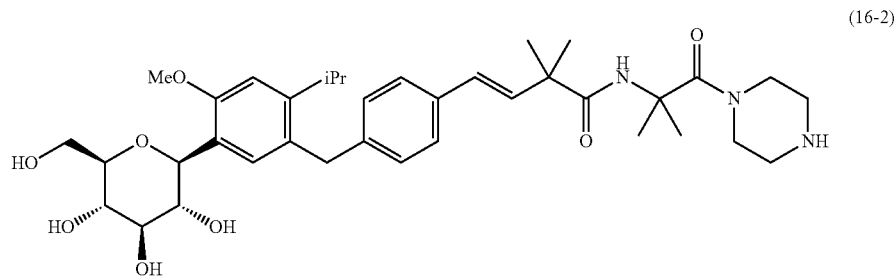

(16-2)

The same procedure as shown in Example 1-2 was repeated to give compound (16-2) (52 mg, 70%) as a colorless amorphous substance, except that compound (1-1) was replaced by compound (16-1).

$^1$H NMR (600 MHz, METHANOL-d$_4$) δ ppm 1.06 (d, J=6.80 Hz, 3H) 1.07 (d, J=6.80 Hz, 3H) 1.34 (s, 6H) 1.42 (s, 6H) 2.67 (br. s., 4H) 3.04-3.12 (m, 1H) 3.27-3.30 (m, 2H) 3.33-3.38 (m, 2H) 3.43-3.49 (m, 1H) 3.50-3.61 (m, 3H) 3.61-3.66 (m, 1H) 3.80 (s, 3H) 3.83 (d, J=11.92 Hz, 1H) 3.92-4.00 (m, 2H) 4.63 (d, J=9.63 Hz, 1H) 6.33-6.39 (m, 1H) 6.44-6.49 (m, 1H) 6.86 (s, 1H) 7.06 (d, J=8.25 Hz, 2H) 7.21 (s, 1H) 7.27 (d, J=8.25 Hz, 2H).

MS ESI/APCI Dual posi: 668[M+H]$^+$, 690[M+Na]$^+$.
MS ESI/APCI Dual nega: 666[M−H]$^-$, 702[M+Cl]$^-$.

Example 17-1

[Chem. 71]

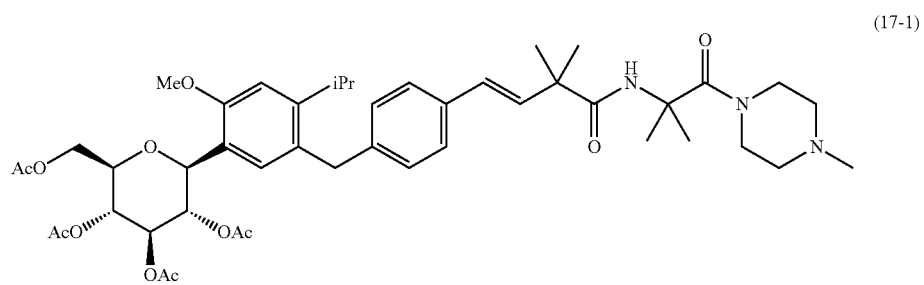

(17-1)

The same procedure as shown in Example 1-1 was repeated to give compound (17-1) (187 mg, 95%) as a colorless amorphous substance, except that intermediate (E) was replaced by intermediate (G), and N,N-dimethylethylenediamine was replaced by 1-methylpiperazine.

$^1$H NMR (300 MHz, CHLOROFORM-d) δ ppm 1.05 (d, J=6.84 Hz, 3H) 1.10 (d, J=6.84 Hz, 3H) 1.36 (s, 6H) 1.59 (s, 6H) 1.77 (s, 3H) 2.00 (s, 3H) 2.05 (s, 3H) 2.06 (s, 3H) 2.26 (s, 3H) 2.32-2.40 (m, 4H) 2.96-3.12 (m, 1H) 3.59-3.71 (m, 4H) 3.79-3.84 (m, 1H) 3.85 (s, 3H) 3.90-4.05 (m, 2H) 4.10-4.16 (m, 1H) 4.21-4.28 (m, 1H) 4.87 (d, J=9.64 Hz, 1H) 5.16-5.27 (m, 1H) 5.29-5.44 (m, 2H) 6.28 (d, J=16.4 Hz, 1H) 6.49 (d, J=16.4 Hz, 1H) 6.77 (s, 1H) 6.83 (s, 1H) 7.01 (d, J=8.08 Hz, 2H) 7.13 (s, 1H) 7.25-7.32 (m, 2H).

MS ESI/APCI Dual posi: 850[M+H]$^+$.
MS ESI/APCI Dual nega: 884[M+Cl]$^-$.

Example 17-2

[Chem. 72]

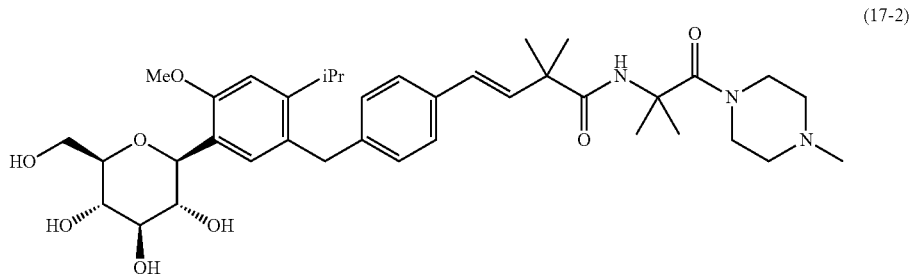

(17-2)

The same procedure as shown in Example 4-2 was repeated to give compound (17-2) (127 mg, 84%) as a colorless amorphous substance, except that compounds (4-1A) and (4-1B) were replaced by compound (17-1).

$^1$H NMR (600 MHz, METHANOL-$d_4$) δ ppm 1.05 (d, J=6.65 Hz, 3H) 1.07 (d, J=6.65 Hz, 3H) 1.36 (s, 6H) 1.45 (s, 6H) 2.14 (s, 3H) 2.23-2.40 (m, 4H) 3.06-3.16 (m, 1H) 3.34-3.42 (m, 2H) 3.46-3.52 (m, 1H) 3.51-3.73 (m, 6H) 3.79-3.91 (m, 4H) 3.98 (s, 2H) 4.65 (d, J=9.63 Hz, 1H) 6.38 (d, J=16.1 Hz, 1H) 6.48 (d, J=16.1 Hz, 1H) 6.88 (s, 1H) 7.08 (d, J=8.25 Hz, 2H) 7.23 (s, 1H) 7.29 (d, J=8.25 Hz, 2H).

MS ESI/APCI Dual posi: 682[M+H]$^+$, 704[M+Na]$^+$.
MS ESI/APCI Dual nega: 716[M+Cl]$^-$.

Anal. Calcd for $C_{38}H_{55}N_3O_8 \cdot 1.6H_2O$: C, 64.2; H, 8.25; N, 5.91. Found: C, 64.3; H, 8.08; N, 5.89.

Test Example 1

(1) Creation of CHO-K1 Cells Stably Expressing Human SGLT1

A plasmid vector expressing human SGLT1 protein was transfected into CHO-K1 cells using lipofectamine 2000 (Invitrogen). The cells were cultured in the presence of 500 µg/mL geneticin to select resistant strains, followed by screening in the system shown below using sugar uptake capacity as an indicator to obtain SGLT1-expressing cells.

(2) Creation of CHO-K1 Cells Stably Expressing Human SGLT2

Method A (described in WO2007/136116): A plasmid vector expressing human SGLT2 protein modified to have Leu-GluSerArgGlyProVal added to the carboxy-terminal final residue was transfected into CHO-K1 cells using lipofectamine 2000 (Invitrogen). The cells were cultured in the presence of 500 µg/mL hygromycin B to select resistant strains, followed by screening in the system shown below using sugar uptake capacity as an indicator to obtain SGLT2-expressing cells. The results calculated by using these stably expressing cells are shown in Table 1 as Method A.

Method B: A plasmid vector expressing human SGLT2 protein was transfected into CHO-K1 cells using lipofectamine LTX (Invitrogen). The cells were cultured in the presence of 1000 µg/mL geneticin to select resistant strains, followed by screening in the system shown below using sugar uptake capacity as an indicator to obtain SGLT2-expressing cells. The results calculated by using these stably expressing cells are shown in Table 1 as Method B.

(3) Inhibition Test for Sodium-Dependent Sugar Uptake in Stably Expressing Cells The stably expressing cells prepared above were used in the following test.

Pretreatment buffer (140 mM choline chloride, 2 mM KCl, 1 mM $CaCl_2$, 1 mM $MgCl_2$, 10 mM HEPES/5 mM Tris, pH 7.4) was added in a volume of 200 µL to the cells stably expressing SGLT1 or 2 mL for Method A and 200 µL for Method B to the cells stably expressing SGLT2, followed by incubation for 20 minutes. The pretreatment buffer was removed and replaced by uptake buffer containing a test compound (1 mM methyl α-D-glucopyranoside (containing [$^{14}$C]methyl α-D-glucopyranoside), 140 mM NaCl, 2 mM KCl, 1 mM $CaCl_2$, 1 mM $MgCl_2$, 10 mM HEPES/5 mM Tris, pH 7.4) in a volume of 75 µL for SGLT1 and SGLT2 in Method B or 200 µL for SGLT2 in Method A. Uptake reaction was performed at 37° C. for 30 minutes (SGLT1) or 60 minutes (SGLT2). After the reaction, the cells were washed twice with washing buffer (10 mM methyl α-D-glucopyranoside, 140 mM choline chloride, 2 mM KCl, 1 mM $CaCl_2$, 1 mM $MgCl_2$, 10 mM HEPES/5 mM Tris, pH 7.4) in a volume of 200 µL for SGLT1 and SGLT2 in Method B or 2 mL for SGLT2 in Method A, and then dissolved in a 0.25 M NaOH solution (75 µL for SGLT1 and SGLT2 in Method B or 400 µL for SGLT2 in Method A). A liquid scintillator (Perkin Elmer) was added and mixed well with each sample, followed by measurement of radioactivity using a β-ray analyzer. For the control group, uptake buffer containing no test compound was prepared. Moreover, another uptake buffer containing choline chloride instead of NaCl was also prepared for basal uptake.

For determination of $IC_{50}$ values, test compounds prepared at 6 appropriate concentrations were used and their concentrations required for 50% inhibition of the amount of sugar uptake ($IC_{50}$ values) were calculated relative to the amount of sugar uptake in the control group (100%). The test results obtained are shown in Table 1.

TABLE 1

| Example | $IC_{50}$ for hSGLT1 (nM) | $IC_{50}$ for hSGLT2 (nM) Method A | $IC_{50}$ for hSGLT2 (nM) Method B |
|---|---|---|---|
| 1-2 | 35 | 2688 | 74 |
| 2-2 | 30 | 971 | 28 |
| 3-2 | 35 | 1723 | 81 |
| 4-2 | 46 | 1643 | 76 |
| 5-2 | 42 | 802 | 30 |
| 6-2 | 27 | 3111 | 64 |
| 7-2 | 46 | 11099 | — |
| 8-3 | 50 | 15721 | 476 |
| 9-2 | 34 | 7234 | 200 |
| 10-2 | 55 | 14889 | 281 |
| 11-2 | 59 | 9754 | 546 |
| 12-2 | 70 | 4948 | 113 |
| 13-2 | 54 | 14781 | 322 |

TABLE 1-continued

| Example | IC$_{50}$ for hSGLT1 (nM) | IC$_{50}$ for hSGLT2 (nM) Method A | IC$_{50}$ for hSGLT2 (nM) Method B |
|---|---|---|---|
| 14-2 | 72 | 2387 | 82 |
| 15-2 | 29 | 1276 | 20 |
| 16-2 | 38 | 1020 | 17 |
| 17-2 | 42 | 979 | 26 |

Table 1 indicates that the compounds of the present invention have strong SGLT1 inhibitory activity and also have some, although weak, SGLT2 inhibitory activity.

Test Example 2

Confirmation Test for Hypoglycemic Effect in Streptozotocin-Induced Diabetic Model Rats (1) Preparation of Diabetic Model Rats SD/IGS rats at 7 weeks of age (male, Charles River Laboratories Japan Inc.) were fasted for about 16 hours and then injected with 50 mg/kg streptozotocin (STZ) via the tail vein under ether anesthesia to prepare diabetic model rats. Similarly, another group of SD/IGS rats at 7 weeks of age was injected with 1.25 mmol/L citric acid in physiological saline (1 mL/kg) via the tail vein under ether anesthesia to prepare normal control rats. At one week after injection of STZ or 1.25 mmol/L citric acid in physiological saline, the rats were provided for an oral glucose tolerance test.

(2) Oral Glucose Tolerance Test (OGTT)

After the diabetic model rats were fasted for about 16 hours, drug groups were each orally administered with a drug (1 mg/kg) dissolved in a 0.5% aqueous carboxymethylcellulose sodium (CMC) solution, while the control group was orally administered with a 0.5% aqueous CMC solution alone. The drugs used were compounds 10, 11 and 33 disclosed in WO07/136116, as well as compounds 1-2, 5-2, 6-2, 13-2 and 15-2 according to the present invention. Immediately after drug administration, a glucose solution (2 g/kg) was orally administered and blood was collected at 6 points in total: before drug administration (0 hour) and 0.25, 0.5, 1, 1.5 and 2 hours after oral administration.

Blood was collected from the tail vein of each rat without anesthesia using a heparin-coated blood collection tube, and centrifuged to separate plasma. Plasma glucose concentrations were quantified by measurement with a Glucose CII-Test Wako (Wako Pure Chemical Industries, Ltd., Japan). To determine the intensity of hypoglycemic effect, the blood glucose level before drug administration was subtracted from each blood glucose level measured until one hour after oral administration in each drug group, and the resulting values were analyzed by the trapezoidal method to calculate an increment in the area under the curve for glucose ($\Delta$AUC), which was expressed as a decrease relative to $\Delta$AUC of the control group.

The results obtained are shown in Tables 2 and 3.

Test Example 3

(1) Changes in Kidney Concentrations of Compounds Disclosed in WO07/136116 Until One Week After Oral Administration SD/IGS rats at 7 weeks of age (male, non-fasting, Charles River Laboratories Japan Inc.) were orally administered with compound 10 or 33 (1 mg/kg) or compound 11 (0.3 mg/kg) prepared in a 0.5% aqueous CMC solution. At 24, 72 and 168 hours after drug administration, the rats were exsanguinated via the postcaval vein under ether anesthesia, and their kidneys were excised after they were confirmed to be euthanized. After the tissue surface was washed with physiological saline, each tissue was measured for its weight and homogenized in 4 volumes of purified water under ice cooling. To each homogenate, an acetonitrile/methanol solution containing an internal standard substance was added to remove proteins, and the supernatant was then subjected to LC-MS/MS (Applied Biosystems API3000). Drug-derived ions generated by electrospray ionization in positive ion mode were detected by selective reaction monitoring. The peak area of the resulting extracted ion chromatogram was analyzed by the internal standard method to calculate the drug concentration in the homogenate.

The internal standard substance used for compounds 10 and 33 was (1S)-1,5-anhydro-1-[5-(4-ethoxybenzyl)-2-methoxy-4-methylphenyl]-1-thio-D-glucitol,ethyl-D$_5$, while the internal standard substance used for compound 11 was compound 11 (trishydroxymethyl-D$_6$; —C(CD$_2$OH)$_3$).

The experimental results obtained are shown in Table 2.

(2) Kidney Concentrations of Inventive Compounds After Repeated Oral Administration for 3 Days SD/IGS rats at 7 weeks of age (male, non-fasting, Charles River Laboratories Japan Inc.) were orally administered once a day for 3 consecutive days with compound 1-2, 5-2, 6-2, 13-2 or 15-2 according to the present invention (3 mg/kg) prepared in a 0.5% aqueous CMC solution. At 48 hours after the final drug administration, the rats were exsanguinated via the postcaval vein under isoflurane anesthesia, and their kidneys were excised after they were confirmed to be euthanized. After the tissue surface was washed with physiological saline, each tissue was measured for its weight and homogenized in 4 volumes of purified water under ice cooling. The drug concentration in each homogenate was determined in the same manner as shown in Test Example 3(1) by LC-MS/MS using compound 11 as an internal standard substance.

The experimental results obtained are shown in Table 3.

TABLE 2

Sugar tolerance test results and kidney concentrations of prior art compounds

| | STZ rats OGTT$ % inhibition | Concentration of compounds in kidney after single oral administration at a dose of 1 mg/kg to male Sprague-Dawley rats | | |
|---|---|---|---|---|
| Compound No. in WO07/136116 | $\Delta$AUC$_{0-1\,h}$ (mg/dl) @1 mg/kg/po | After 1 day (ng/g) | After 3 days (ng/g) | After 7 days (ng/g) |
| compound 10 | 69 | 167 ± 36.3 | 124 ± 21.2 | 53.8 ± 7.61 |
| compound 11 | 68 | 63.5 ± 20.1* | 67.3 ± 3.15* | 48.7 ± 18.3* |
| compound 33 | 81# | 29.8 ± 6.79 | 25.5 ± 8.68 | 16.2 ± 3.11 |

*The value represents mean ± S.D. when compound 11 was orally administered at 0.3 mg/kg.
$Suppression of glucose AUC$_{0-1\,h}$ in streptozotocin (STZ)-induced diabetic rats versus vehicle control, following an oral dose at 1 mg/kg.
OGTT using Sprague-Dawley rats.

Compounds 10, 11 and 33 disclosed in WO2007/136116 are as shown below.

[Chem. 73]

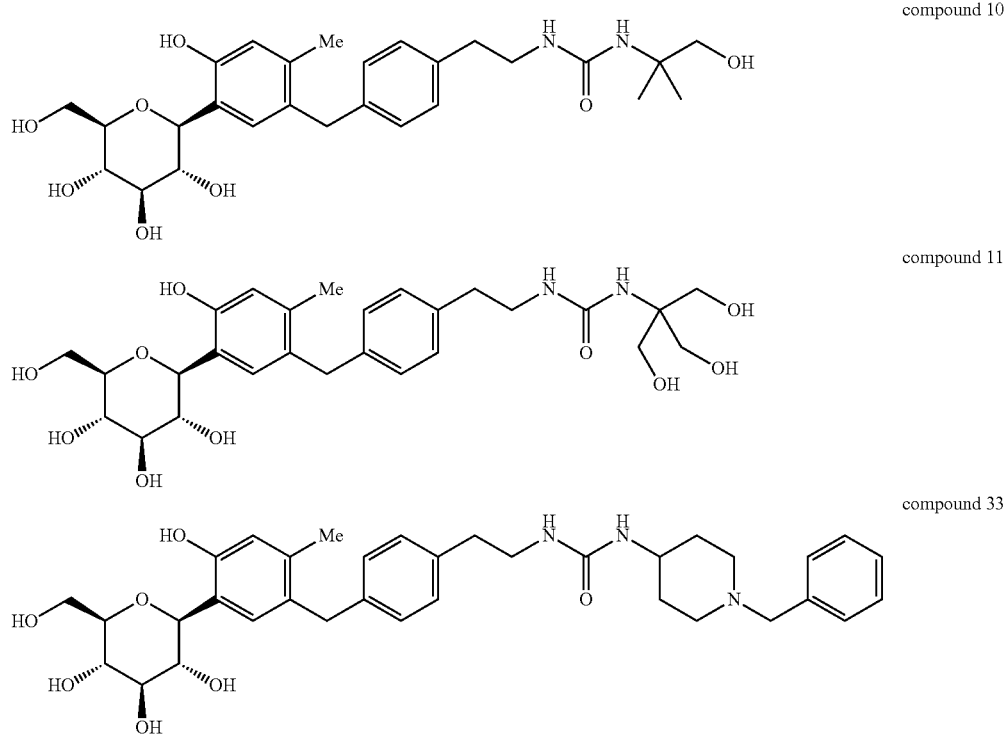

compound 10 compound 11 compound 33

TABLE 3

Sugar tolerance test results and kidney concentrations of inventive compounds

| Example No. | STZ rats OGTT* % inhibition $\Delta AUC_{0-1\,h}$ (mg/dl) @1 mg/kg/po | Concentration of compounds in kidney after 3 days continuous oral administration at a dose of 3 mg/kg to male Sprague-Dawley rats After 2 days (ng/g) |
|---|---|---|
| 1-2 | 74 | BLQ# |
| 5-2 | 66 | BLQ |
| 6-2 | 64 | BLQ |
| 13-2 | 54 | BLQ |
| 15-2 | 62 | BLQ |

*Suppression of glucose $AUC_{0-1\,h}$ in STZ-induced diabetic rats versus vehicle control, following an oral dose at 1 mg/kg.
BLQ means below lower limit of quantification(5 ng/g).

The compounds disclosed in WO2007/136116 showed a strong hypoglycemic effect in the sugar tolerance test after oral administration at 1 mg/kg. However, at 1, 3 and 7 days after 1 mg/kg oral administration, their concentrations in the kidney were not substantially reduced, and the compounds tended to remain in the kidney without being excreted even after 7 days (Table 2).

On the other hand, the compounds of the present invention were found to have a strong hypoglycemic effect, as in the case of the above prior art compounds. Moreover, the compounds of the present invention exhibited a characteristic feature in that even when they were administered for 3 consecutive days at a dose of 3 mg/kg, they unexpectedly did not remain in the kidney at subsequent day 2 (Table 3).

A possible cause of this difference is that the compounds of the present invention are less likely to be absorbed in the small intestine, and the absorbed compounds will also be excreted without remaining in the kidney.

Thus, the compounds of the present invention have no tendency to remain in the body and are less likely to cause side effects and toxicity due to continuous administration, and hence appear to have practically excellent properties as pharmaceutical preparations.

INDUSTRIAL APPLICABILITY

The present invention enables the provision of agents for improving postprandial hyperglycemia, which have strong SGLT1 inhibitory activity and have no tendency to accumulate in the body. The present invention also contributes to an improvement in human health and facilitates the wholesome development of the pharmaceutical industry through contribution to the treatment and prevention of postprandial hyperglycemia-induced diseases against which inhibition of SGLT1 activity is effective.

The invention claimed is:

1. A 4-isopropylphenyl glucitol compound represented by the following formula (I) or a pharmaceutically acceptable salt thereof:

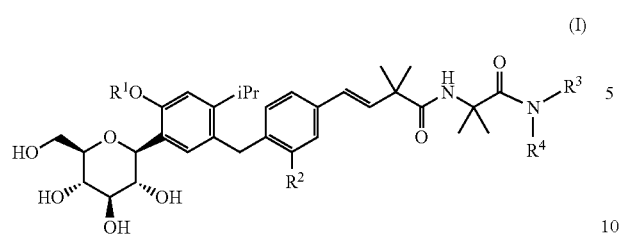

wherein
R$^1$ represents a hydrogen atom or a C$_{1-4}$ alkyl group,
R$^2$ represents a hydrogen atom or a methyl group,
R$^3$ represents a "C$_{1-4}$ alkyl group substituted with an amino group(s) or a di-C$_{1-4}$ alkylamino group(s)" or a piperidyl group, and
R$^4$ represents a hydrogen atom, or alternatively, R$^3$ and R$^4$ together with their adjacent nitrogen atom form a piperidino group or a piperazinyl group, which may be substituted with a C$_{1-4}$ alkyl group(s) or a dimethylamino group(s).

2. A 4-isopropylphenyl glucitol compound selected from the following group or a pharmaceutically acceptable salt thereof:

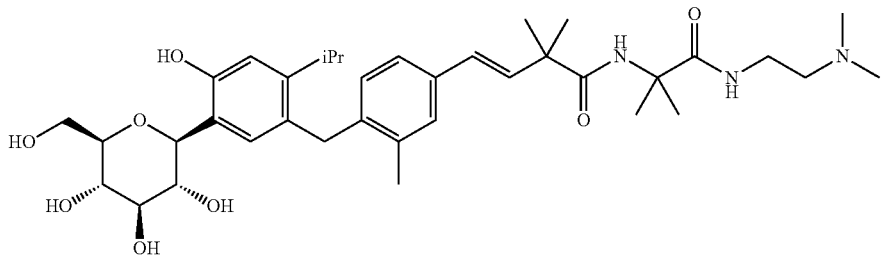

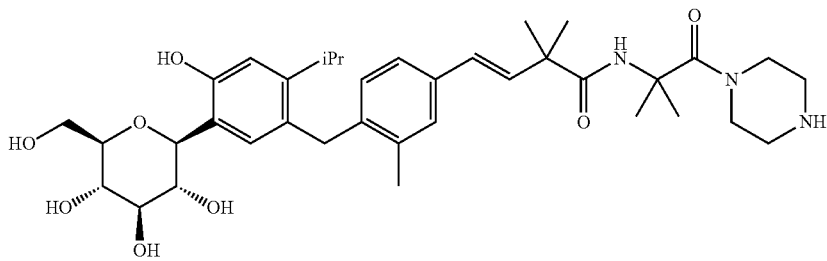

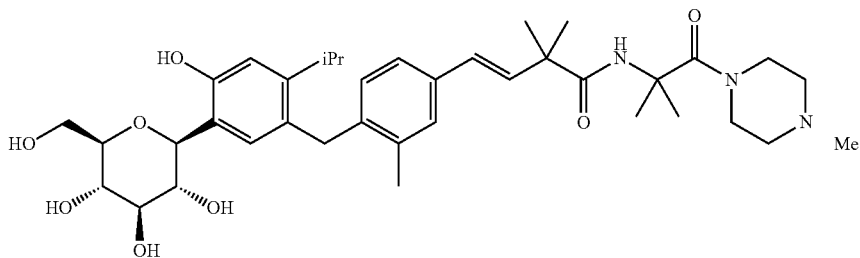

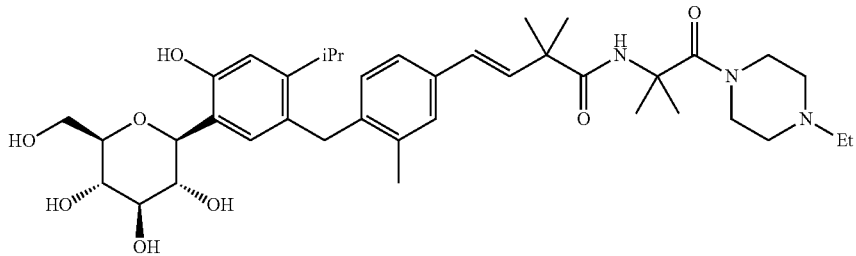

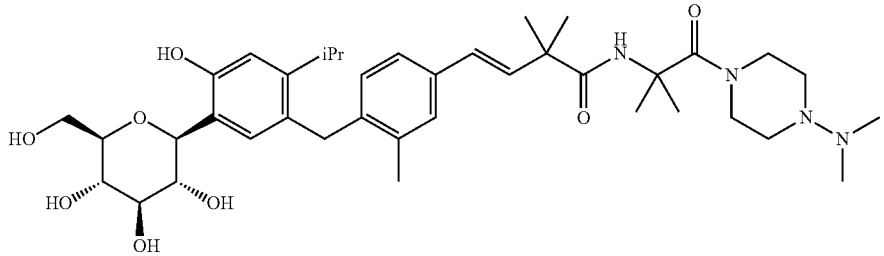

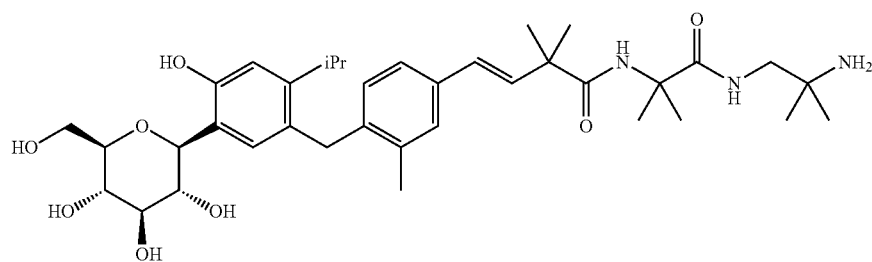
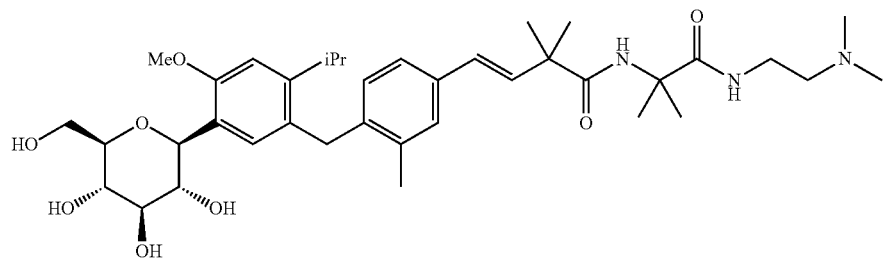
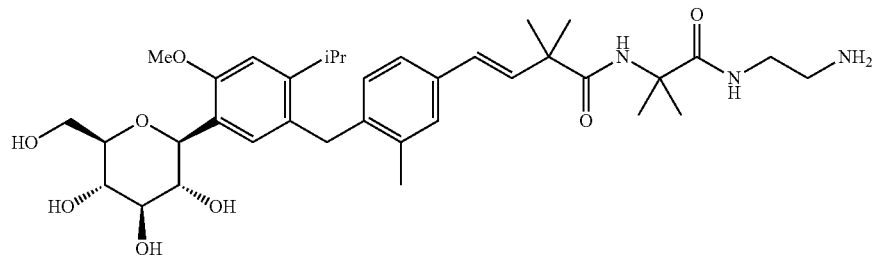
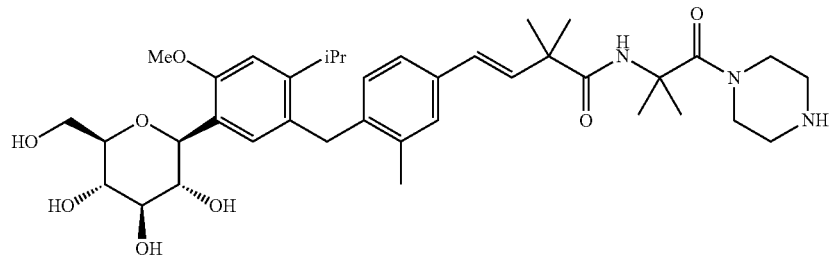
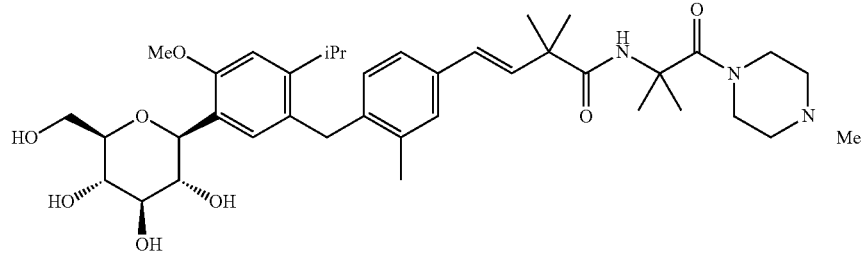
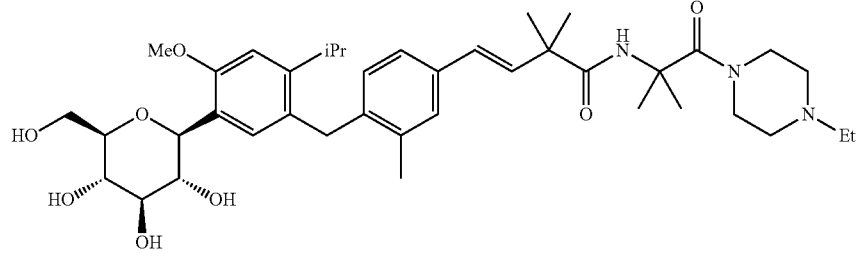

-continued
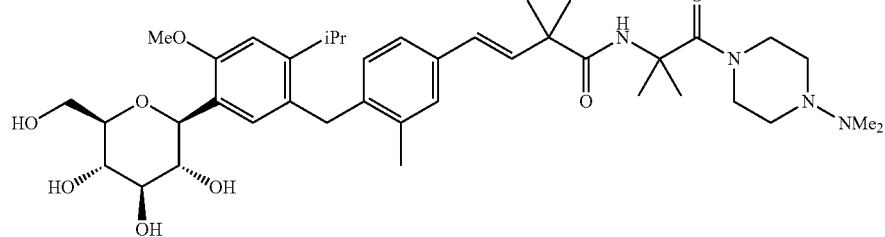
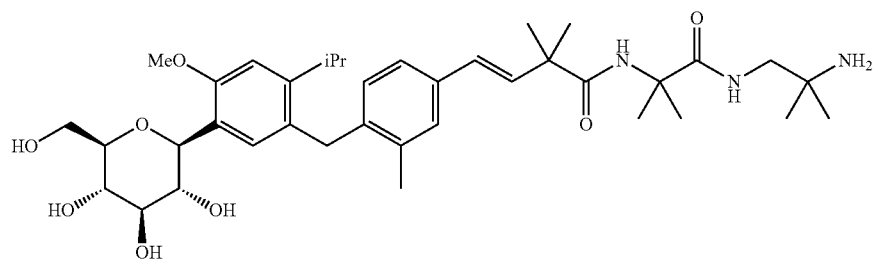
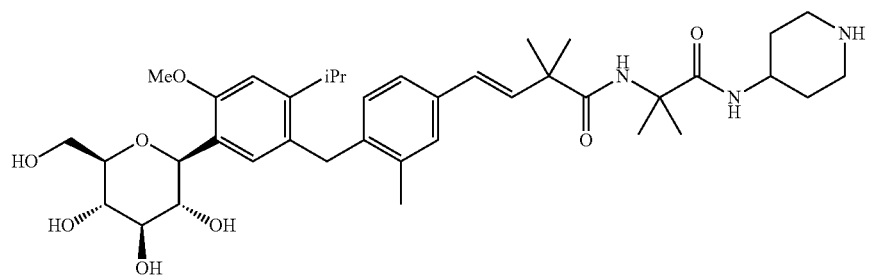
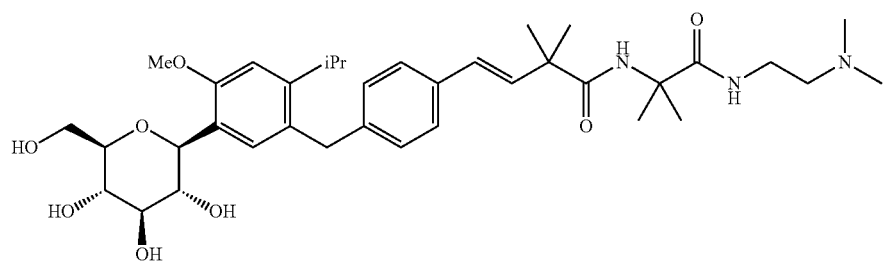
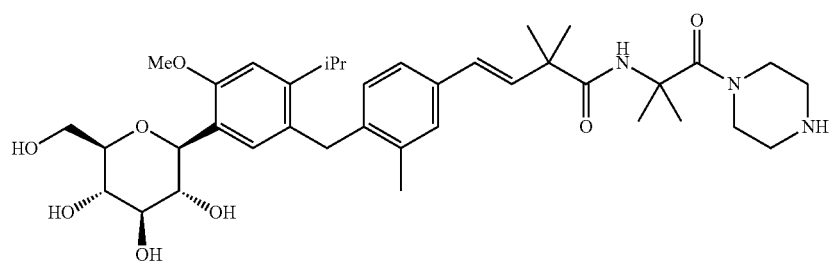
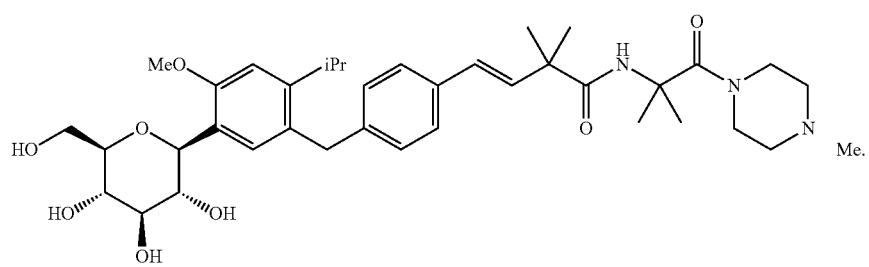

3. A 4-isopropylphenyl glucitol compound selected from the following group or a pharmaceutically acceptable salt thereof:

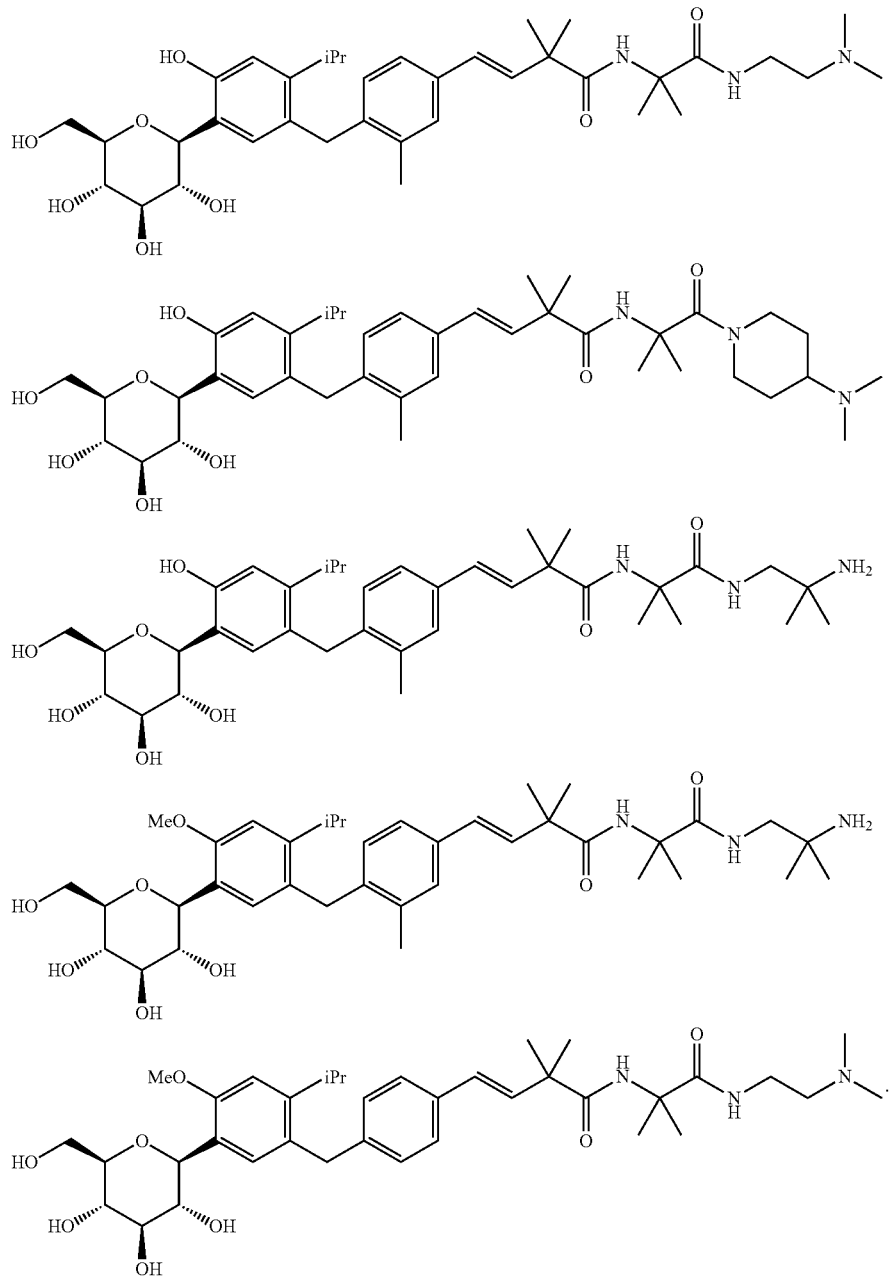

4. A pharmaceutical preparation, which comprises the 4-isopropylphenyl glucitol compound according to claim 1 or a pharmaceutically acceptable salt thereof as an active ingredient.

5. An inhibitor of sodium-dependent glucose transporter 1 (SGLT1) activity, which comprises the 4-isopropylphenyl glucitol compound according to claim 1 or a pharmaceutically acceptable salt thereof as an active ingredient.

6. An agent for improving postprandial hyperglycemia, which comprises the 4-isopropylphenyl glucitol compound according to claim 1 or a pharmaceutically acceptable salt thereof as an active ingredient.

7. A therapeutic agent for diabetes, which comprises the 4-isopropylphenyl glucitol compound according to claim 1 or a pharmaceutically acceptable salt thereof as an active ingredient.

* * * * *